(12) United States Patent
Baum

(10) Patent No.: US 7,695,937 B2
(45) Date of Patent: Apr. 13, 2010

(54) POLYNUCLEOTIDES ENCODING C-TYPE LECTIN POLYPEPTIDES AND METHODS OF USE THEREOF

(75) Inventor: Peter Robert Baum, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 12/079,183

(22) Filed: Mar. 25, 2008

(65) Prior Publication Data

US 2008/0182793 A1    Jul. 31, 2008

Related U.S. Application Data

(62) Division of application No. 10/499,184, filed as application No. PCT/US02/41158 on Dec. 19, 2002, now Pat. No. 7,396,662.

(60) Provisional application No. 60/342,001, filed on Dec. 19, 2001.

(51) Int. Cl.
*C12P 21/06*    (2006.01)

(52) U.S. Cl. .................. 435/69.1; 435/6; 435/325; 435/320.1; 536/23.1; 530/350

(58) Field of Classification Search .............. None
See application file for complete search history.

(56) References Cited

U.S. PATENT DOCUMENTS

| 5,593,882 | A | 1/1997 | Erbe et al. |
| 7,087,737 | B2 * | 8/2006 | Goddard et al. ............. 536/23.2 |
| 7,189,838 | B2 * | 3/2007 | Goddard et al. ............. 536/23.5 |
| 2004/0018555 | A1 | 1/2004 | Anderson et al. |

FOREIGN PATENT DOCUMENTS

WO    WO 0168848 A2    9/2001

OTHER PUBLICATIONS

Seffernick et al. (J. Bacteriology, vol. 183, pp. 2405-2410).*
Bowie et al., Deciphering the message in protein sequences: tolerance to amino acid subsitutions, *Science* 247:1306-1310, 1990.
Rudinger, J., Characteristics of the amino acids as components of a peptide hormone sequence, University Park Press, Baltimore, 1994, pp. 1-7.

* cited by examiner

*Primary Examiner*—Hope A Robinson
(74) *Attorney, Agent, or Firm*—Christine M. Bellas

(57) ABSTRACT

Provided herein are polypeptide and polynucleotide sequences for a molecule having homology to the C-type lectin family of polypeptides. Also provided are methods of making and using the polypeptide and polynucleotides.

7 Claims, 4 Drawing Sheets

FIGURE 1

Color code
Italicized = Transmembrane domain 1
Underlined = Transmembrane domain 2
Double Underlined = Transmembrane domain 3
Lectin domain is in bold
(SEQ ID NO:)

```
           10        20        30        40        50        60        70        80        90       100
 (8)  MSEEVTYATLTFQDSAGARNNRDGNNLRKRGHPAPSPIWRHAALGLVTLCLMLLIGLVTLGMMFLQISNDINSDSEKLSQLQKTIQQQQDNLSQQLGNSN
 (2)  MSEEVTYATLTFQDSAGARNNRDGNNLRKRGHPAPSPIWRHAALGLVTLCLMLLIGLVTLGMMFLQISNDINSDSEKLSQLQKTIQQQQDNLSQQLGNSN
(16)  MSEEVTYATLTFQDSAGARNNRDGNNLRKRGHPAPSPIWRHAALGLVTLCLMLLIGLVTLGMMFLQISNDINSDSEKLSQLQKTIQQQQDNLSQQLGNSN
(14)  MSEEVTYATLTFQDSAGARNNRDGNNLRKRGHPAPSPIWRHAALGLVTLCLMLLIGLVTLGMMFLQISNDINSDSEKLSQLQKTIQQQQDNLSQQLGNSN
(12)  MSEEVTYATLTFQDSAGARNNRDGNNLRKRGHPAPSPIWRHAALGLVTLCLMLLIGLVTLGMMFLQISNDINSDSEKLSQLQKTIQQQQDNLSQQLGNSN
(10)  MSEEVTYATLTFQDSAGARNNRDGNNLRKRGHPAPSPIWRHAALGLVTLCLMLLIGLVTLGMMFLQISNDINSDSEKLSQLQKTIQQQQDNLSQQLGNSN
 (6)  MSEEVTYATLTFQDSAGARNNRDGNNLRKRGHPAPSPIWRHAALGLVTLCLMLLIGLVTLGMMFLQISNDINSDSEKLSQLQKTIQQQQDNLSQQLGNSN
 (4)  MSEEVTYATLTFQDSAGARNNRDGNNLRKRGHPAPSPIWRHAALGLVTLCLMLLIGLVTLGMMFLQISNDINSDSEKLSQLQKTIQQQQDNLSQQLGNSN
      ****************************************************************************************************

110       120       130       140       150       160       170       180       190       200
 (8)  NLSMEEEFLKSQISSLLKRQEQMAIKLCQELIIHTSGFSYVTAITHVFVLLAGIIMGLLWQKLVLGRWLCSLSILC---------------------
 (2)  NLSMEEEFLKSQISSLLKRQEQMAIKLCQELIIHTSGFSYVTAITHVFVLLAGIIMGLLWQKLVLGRWLCSLSILHVVNVFLN---------------
(16)  NLSMEEEFLKSQISSLLKRQEQMAIKLCQELIIHTSGFSYVTAITHVFVLLAGIIMGLLWQKLVLGRWLCSLSILI---------------------
(14)  NLSMEEEFLKSQISSLLKRQEQMAIKLCQELIIHTSGFSYVTAITHVFVLLAGIIMGLLWQKLVLGRWLCSLSILVRL------------------
(12)  NLSMEEEFLKSQISSVLKRQEQMAIKLCQELIIHTSDHRCNPCPKMWQWYQNSCYYFTTNEEKTWANSRKDCIDKNSTLVKIDSLEEKDFLMSQPLLMFS
(10)  NLSMEEEFLKSQISSLLKRQEQMAIKLCQELIIYTSDHRCNPCPKMWQWYQNSCYYFTTNEEKTWANSRKDCIDKNSTLVKIDSLEEKDFLMSQPLLMFS
 (6)  NLSMEEEFLKSQISSLLKRQEQMAIKLCQELIIHTSDHRCNPCPKMWQWYQNSCYYFTTNEEKTWANSRKDCIDKNSTLVKIDSLEEKDFLMSQPLLMFS
 (4)  NLSMEEEFLKSQISSLLKRQEQMAIKLCQELIIHTSDHRCNPCPKMWQWYQNSCYYFTTNEEKTWANSRKDCIDKNSTLVKIDSLEEKDFLMSQPLLMFS
      *******************************  ..

210       220       230       240       250       260       270
 (8)  --------------------------------------------------------------------
 (2)  --------------------------------------------------------------------
(16)  --------------------------------------------------------------------
(14)  --------------------------------------------------------------------
(12)  FFWLGLSWDSSGRSWFWEDGSVPSPSLFSTKELDQINGSKGCAYFQKGNIYISRCSAEIFWICEKTAAPVKTEDLD
(10)  FFWLGLSWDSSGRSWFWEDGSVPSPSF------------------------AEIFWICEKTAAPVKTEDLD
 (6)  FFWLGLSWDSSGRSWFWEDGSVPSPSLYVSNY---------------------------------------
 (4)  FFWLGLSWDSSGRSWFWEDGSVPSPSFMLSTFS--------------------------------------
```

FIGURE 2-A

```
                                        1                                                  50
gi|126132|sp|P07306|LECH_HUMAN      ~~~~~~~~~~ ~~~~~~~~~~ ~~~~~~~~~~ ~~~~~~~~~~ ~~~~~~~~~~
gi|5453684|ref|NP_006335            ~~~~~~~~~~ ~~~~~~~~~~ ~~~~~~~~~~ ~~~~~~~~~~ ~~~~~~~~~~
gi|422857|pir||A46274               MSDSKEPRLQ QLGLLEEEQL RGLGFRQTRG YKSLAGCLGH GPLVLQLLSF
gi|182450|gb|AAA52435               ~~~~~~~~~~ ~~~~~~~~~~ ~~~~~~~~~~ ~~~~~~~~~~ ~~~~~~~~~~
gi|4505501|ref|NP_002534            ~~~~~~~~~~ ~~~~~~~~~~ ~~~~~~~~~~ ~~~~~~~~~~ ~~~~~~~~~~
gi|13358173|gb|AAG33923             ~~~~~~~~~~ ~~~~~~~~~~ ~~~~~~~~~~ ~~~~~~~~~~ ~~~~~~~~~~
SEQ ID NO:12                        ~~~~~~~~~~ ~~~~~~~~~~ ~~~~~~~~~~ ~~~~~~~~~~ ~~~~~~~~~~
gsp|AAW40215                        ~~~~~~~~~~ ~~~~~~~~~~ ~~~~~~~~~~ ~~~~~~~~~~ ~~~~~~~~~~
gi|7110216|gb|AAF36830              ~~~~~~~~~~ ~~~~~~~~~~ ~~~~~~~~~~ ~~~~~~~~~~ ~~~~~~~~~~
gi|7109731|gb|AAF36777              ~~~~~~~~~~ ~~~~~~~~~~ ~~~~~~~~~~ ~~~~~~~~~~ ~~~~~~~~~~
gi|4502681|ref|NP_001772            ~~~~~~~~~~ ~~~~~~~~~~ ~~~~~~~~~~ ~~~~~~~~~~ ~~~~~~~~~~
gi|88231|pir||PT0372                ~~~~~~~~~~ ~~~~~~~~~~ ~~~~~~~~~~ ~~~~~~~~~~ ~~~~~~~~~~

51                                                 100
gi|126132|sp|P07306|LECH_HUMAN      ~~~~~~~~~~ ~~~~~~~~~~ ~~~~~~~~~~ ~~~~~~~~~~ ~~~~~~MTKE
gi|5453684|ref|NP_006335            ~~~~~~~~~~ ~~~~~~~~~~ ~~~~~~~~~~ ~~~~~~~~~~ ~~~~~~MTRT
gi|422857|pir||A46274               TLLAGLLVQV SKVPSSISQE QSRQDAIYQN LTQLKAAVGE LSEKSKLQEI
gi|182450|gb|AAA52435               ~~~~~~~~~~ ~~~~~~~~~~ ~~~~~~~~~~ ~~~~~~~~~~ ~~~~~~~~~~
gi|4505501|ref|NP_002534            ~~~~~~~~~~ ~~~~~~~~~~ ~~~~~~~~~~ ~~~~~~~~~~ ~~~~~~~~~~
gi|13358173|gb|AAG33923             ~~~~~~~~~~ ~~~~~~~~~~ ~~~~~~~~~~ ~~~~~~~~~~ ~~~~~~~~~~
SEQ ID NO:12                        ~~~~~~~~~~ ~~~~~~~~~~ ~~~~~~~~~~ ~~~~~~~~~~ ~~~~~~~~~~
gsp|AAW40215                        ~~~~~~~~~~ ~~~~~~~~~~ ~~~~~~~~~~ ~~~~~~~~~~ ~~~~~~~~~~
gi|7110216|gb|AAF36830              ~~~~~~~~~~ ~~~~~~~~~~ ~~~~~~~~~~ ~~~~~~~~~~ ~~~~~~~~~~
gi|7109731|gb|AAF36777              ~~~~~~~~~~ ~~~~~~~~~~ ~~~~~~~~~~ ~~~~~~~~~~ ~~~~~~~~~~
gi|4502681|ref|NP_001772            ~~~~~~~~~~ ~~~~~~~~~~ ~~~~~~~~~~ ~~~~~~~~~~ ~~~~~~~~~~
gi|88231|pir||PT0372                ~~~~~~~~~~ ~~~~~~~~~~ ~~~~~~~~~~ ~~~~~~~~~~ ~~~~~~~~~~

101                                                150
gi|126132|sp|P07306|LECH_HUMAN      YQDLQHLDNE ESDHHQLRKG PPPPQPLLQR ...LCSGPRL LLLSLGLSLL
gi|5453684|ref|NP_006335            YENFQYLENK VK.VQGFKNG PLPLQSLLQR ...LRSGPCH LLLSLGLGLL
gi|422857|pir||A46274               YQELTQLKAA VGELPEKSKL QEIYQE.LTR ...LKAAVGE LPEKSKLQEI
gi|182450|gb|AAA52435               ~~~~~~~~~~ ~~~~~~MEEG QYSEIEELPR RRCCRRGTQI VLLGLVTAAL
gi|4505501|ref|NP_002534            ~~~~~~~~~~ ~~~~~~~~~~ ~~~MTFDDLK IQTVKDQPDE KSNGKKAKGL
gi|13358173|gb|AAG33923             ~~~~~~~~~~ ~~~~~~~~~~ ~~~~~~~~~~ ~~~~~~~~~~ ~~~~~~~~~~
SEQ ID NO:12                        ~~~~~~~~~~ ~~~~~~~~~M SEEVTYATLT FQDSAGARNN RDGNNLRKRG
gsp|AAW40215                        ~~~~~~~~~~ ~~~~~~~~~M SEEVTYADLQ FQNSSEMEKI PEIGKFGEKA
gi|7110216|gb|AAF36830              ~~~~~~~~~M QAKYSSTRDM LDDDGDTTMS LHSQASA..T TRHPEPRRTE
gi|7109731|gb|AAF36777              ~~~~~~~~~~ ~~~~~~~~~M QDEDGYITLN IKTRKPA..L V.......SV
gi|4502681|ref|NP_001772            ~~~~~~~~~~ ~~~~~~~~~~ ~~~~~~~~~~ ~~~~~~~~~~ ~~~~~~~~~~
gi|88231|pir||PT0372                ~~~~~~~~~~ ~~~~~~~~~~ ~~~~~~~~~~ ~~~~~~~~~~ ~~~~~~~~~~

151                                                200
gi|126132|sp|P07306|LECH_HUMAN      ...LLVVVCV IGS..QNS.. QLQEELRGLR ETFSNFTAST EAQVKGLSTQ
gi|5453684|ref|NP_006335            ...LLVIICV VGF..QNS.. KFQRDLVTLR TDFSNFTSNT VAEIQALTSQ
gi|422857|pir||A46274               YQELTWLKAA VGELPEKS.. KMQE....IY QELTRLKA.A VGELPEKSKQ
gi|182450|gb|AAA52435               WAGLLTLLLL WHWDTTQSLK QLEERAARNV SQVSKNLESH HGDQMAQKSQ
gi|4505501|ref|NP_002534            QFLYSPWWCL AAATLGVLCL GLVVTIMVLG MQLSQVSDLL TQEQANLTHQ
gi|13358173|gb|AAG33923             ~~~~~~~~~~ ~~~~~~~~~~ ~~~~~~~~~~ ~~~~~~~~~~ ~~~~~~~~~~
SEQ ID NO:12                        HPAPSPIWRH AALGLVTLCL MLLIGLVTLG MMFLQISNDI NSDSEKLSQL
gsp|AAW40215                        PPAPSHVWRP AAFLTLLCL LLLIGLGVLA SMF.HVT..L KIEMKKMNKL
gi|7110216|gb|AAF36830              HRAPSSTWRP VALTLLTLCL VLLIGLAAWG LLFFQY.... ...YQLSNTG
gi|7109731|gb|AAF36777              GSASSSWWRV MALILLILYV GMVVGLVALG I..WSV.... ...MQ.RNYL
gi|4502681|ref|NP_001772            ~~~~~~~~~~ ~~~~~~~~~~ ~~~~~~~~~~ ~~~~~~~~~~ ~~MSSENCFV
gi|88231|pir||PT0372                ~~~~~~~~~M DNQGVIYSDL NLPPNPKRQQ RKPKGNKSSI LATEQEITYA 201                                                250
gi|126132|sp|P07306|LECH_HUMAN      GGNVGRKMKS LESQL.EKQQ KDLS...... ......EDHS SLLLHVKQFV
gi|5453684|ref|NP_006335            GSSLEETIAS LKAEV.EGFK QERQ...... ......AVHS EMLLRVQQLV
gi|422857|pir||A46274               QEIYQELTR LKAAVGELPE KSKQ...... ......QEIY QELTRLKAAV
gi|182450|gb|AAA52435               STQISQELEE LRAEQQRLKS QDLELSWNLN GLQADLSSFK SQELNERNEA
gi|4505501|ref|NP_002534            KKKLEGQISA RQQAEEASQ. ...E..SENE .LKEMIETLA RKLNEKSKEQ
```

FIGURE 2-B

```
gi|13358173|gb|AAG33923        ---MEYHPDL ENLDEDGYT. ...QLHFDSQ .SNTRIAVVS EKGSCAASPP
SEQ ID NO:12                   QKTIQ..... .QQQDNLSQ. ...QLGNSNN .LSMEEEFLK SQISSVLKRQ
gsp|AAW40215                   QNISE..... .ELQRNISL. ...QLMSNMN .IS....... NKIRNLSTTL
gi|7110216|gb|AAF36830         QDTIS..... .QMEERLG.. .........N .TSQELQSLQ VQNIKLAGSL
gi|7109731|gb|AAF36777         QD........ .ENENRTG.. .......... .TLQQLAK.. .......RFC
gi|4502681|ref|NP_001772       AENSSLHPES GQENDAT..S PHFSTRHEGS .FQ..VPVLC AVMNVVFITI
gi|88231|pir||PT0372           ELNLQKASQD FQGNDKTYHC KDLPSAPEKL .IVGILGIIC LILMASVVTI 251                                                     300
gi|126132|sp|P07306|LECH_HUMAN SDLRSLSCQM A..ALQG.NG ....SERTC. .CPVNWVEHE RSCYWF.SRS
gi|5453684|ref|NP_006335       QDLKKLTCQV A..TLNN.NG EEASTEGTC. . PVN VEHQ DS YWF.SHS
gi|422857|pir||A46274          GELPEKSKQQ E..IYQELTQ LKAAVERLCH P PWE TFFQ GN YFM.SNS
gi|182450|gb|AAA52435          SDLLERLREE V..TKLRME. LQVSSGFVCN T PEK INFQ RK YYF.GKG
gi|4505501|ref|NP_002534       MELHHQNLN. ........LQE TLKRVANCSA P PQD IWHG EN YLF.SSG
gi|13358173|gb|AAG33923        WRLIAVILGI LCLVILVIAV VLGTMGVLSS P PPN IIYE KS YLF.SMS
SEQ ID NO:12                   EQMAIKLCQE LII....... ..HTSDHRCN P PKM QWYQ NS YYFTTNE
gsp|AAW40215                   QTIATKLCRE LYS....... ..KEQEHKCK P PRR IWHK DS .YFLSDD
gi|7110216|gb|AAF36830         QHVAEKLCRE LYN....... ..KAGAHRCS P TEQ KWHG DN YQFYKDS
gi|7109731|gb|AAF36777         QYVVKQ..SE LKG....... ..TFKGHKCS P DTN RYYG DS YGFFRHN
gi|4502681|ref|NP_001772       LIIALIALSV GQYNCPGQYT FSMPSDSHVS S SED VGYQ RK Y.FISTV
gi|88231|pir||PT0372           VVIP..STLI QRHNNSSLNT RTQKA.RHCG H PEE ITYS NS Y.YIGKE
                                                                      *        *       *

301                                                     350
gi|126132|sp|P07306|LECH_HUMAN GKAWADADNY CRLEDAHLVV VTSWEEQKFV QHHIGPVN.. T.WMGLHD..
gi|5453684|ref|NP_006335       GMS AEAEKY  QLKNAHLVV INSREEQNFV QKYLGSAY.. T. M LSD..
gi|422857|pir||A46274          QRN HDSITA  KEVGAQLVV IKSAEEQNFL QLQSSRSNRF T. M LSDLN
gi|182450|gb|AAA52435          TKQ VHARYA  DDMEGQLVS IHSPEEQDFL TKHAS..HTG S.  I LRNLD
gi|4505501|ref|NP_002534       SFN EKSQEK  LSLDAKLLK INSTADLDFI .QQAISYSSF PF M LSRRN
gi|13358173|gb|AAG33923        LNS DGSKRQ  WQLGSNLLK IDSSNELGFI VKQVSSQPDN SF I LSRPQ
SEQ ID NO:12                   EKT ANSRKD  IDKNSTLVK IDSLEEKDFL MSQPLLMFSF .F L LSWDS
gsp|AAW40215                   VQT QESKMA  AAQNASLLK INNKNALEFI KSQSR...SY DY L LSPEE
gi|7110216|gb|AAF36830         .KS EDCKYF  LSENSTMLK INKQEDLEFA ASQSYSEFFY SY T LLRPD
gi|7109731|gb|AAF36777         .LT EESKQY  TDMNATLLK IDNRNIVEYI KARTH....L IR V LSRQK
gi|4502681|ref|NP_001772       KRS TSAQNA  SEHGATLAV IDSEKDMNFL KRYAGREEH. ... V L.KKE
gi|88231|pir||PT0372           RRT EESLLA  TSKNSSLLS IDNEEEMKFL SIIS..PSS. ... I VFRNS
                                    *          *                                      * *

351                                                     400
gi|126132|sp|P07306|LECH_HUMAN QNGPWKWVDG TDYETGFKN. WRPEQPDDWY GHGLGGGEDC AHFTDDGRWN
gi|5453684|ref|NP_006335       PEGAWKWVDG TDYATGFQN. WKPGQPDDWQ GHGLGGGED  AHFHPDGRWN
gi|422857|pir||A46274          QEGTWQWVDG SPLLPSFKQY WNRGEPNN.. ....VGEED  AEFSGNG.WN
gi|182450|gb|AAA52435          LKGEFIWVDG SHV..DYSN. WAPGEPTS.. ...RSQGED  VMMRGSGRWN
gi|4505501|ref|NP_002534       PSYPWLWEDG SPLMPHLFRV .......RGA VSQTYPSGT  AYIQ.RGAVY
gi|13358173|gb|AAG33923        TEVPWLWEDG STFSSNLFQI .......RTT ATQENPSPN  VWIH.VSVIY
SEQ ID NO:12                   SGRSWFWEDG SVPSPSLFST .......K.E LDQINGSKG  AYFQ.KGNIY
gsp|AAW40215                   DSTRGMRVDN IINS.SAWVI .......R.N APDLN.NMY  GYIN.RLYVQ
gi|7110216|gb|AAF36830         SGKAWLWMDG TPFTSELFHI .......I.I DVTSPRSRD  VAIL.NGMIF
gi|7109731|gb|AAF36777         SNEVWKWEDG SVISENMFEF .......L.E D..GKGNMN  AYFH.NGKMH
gi|4502681|ref|NP_001772       PGHPWKWSNG KEFN.NWFNV .......TGS D.......K  VFLK.NTEVS
gi|88231|pir||PT0372           SHHPWVTMNG LAFK.H..EI .......KDS D...NAELN  AVLQ.VNRLK
                                                                             *

401                                                     450
gi|126132|sp|P07306|LECH_HUMAN DDVCQRPY.R WVCETELDKA SQEPPLL~~~ ~~~~~~~~~~ ~~~~~~~~~~
gi|5453684|ref|NP_006335       DDV QRPY.H WV EAGLGQT SQESH~~~~~ ~~~~~~~~~~ ~~~~~~~~~~
gi|422857|pir||A46274          DDK NLAK.F  WI KKSAASC SRDEEQFLSP APATPNPPPA ~~~~~~~~~~
gi|182450|gb|AAA52435          DAF DRKLGA  WV DRLATCT PPASEGSAES MGPDSRPDPD GRLPTPSAPL
gi|4505501|ref|NP_002534       AEN ILA.AF  SI QKKANLR AQ~~~~~~~~ ~~~~~~~~~~ ~~~~~~~~~~
gi|13358173|gb|AAG33923        DQL SVP.SY  SI EKKFSM~ ~~~~~~~~~~ ~~~~~~~~~~ ~~~~~~~~~~
SEQ ID NO:12                   ISR SAE.IF  WI EKTAAPV KTEDLD~~~~ ~~~~~~~~~~ ~~~~~~~~~~
gsp|AAW40215                   YYH TYK.KR  MI EKMANPV QLV.LHILGR HEASIKYI~~ ~~~~~~~~~~
gi|7110216|gb|AAF36830         SKD KEL.KR  CV ERRAGMV KPESLHVPPE TLGEGD~~~~ ~~~~~~~~~~
gi|7109731|gb|AAF36777         PTF ENK.HY  LM ERKAGMT KVDQLP~~~~ ~~~~~~~~~~ ~~~~~~~~~~
gi|4502681|ref|NP_001772       SME EKN.LY  WI NKPYK~~ ~~~~~~~~~~ ~~~~~~~~~~ ~~~~~~~~~~
```

FIGURE 2-C

```
gi|88231|pir||PT0372              SAQ GSS.II YH KHKL~~~ ~~~~~~~~~~ ~~~~~~~~~~ ~~~~~~~~~~
                                      *          *
                                                451
gi|126132|sp|P07306|LECH_HUMAN    ~~
gi|5453684|ref|NP_006335          ~~
gi|422857|pir||A46274             ~~
gi|182450|gb|AAA52435             HS
gi|4505501|ref|NP_002534          ~~
gi|13358173|gb|AAG33923           ~~
SEQ ID NO:12                      ~~
gsp|AAW40215                      ~~
gi|7110216|gb|AAF36830            ~~
gi|7109731|gb|AAF36777            ~~
gi|4502681|ref|NP_001772          ~~
gi|88231|pir||PT0372              ~~
```

KEY:                                                              Ligand
AAA52435= CD23                                                    sugars
A46274=   CD209(DC ICAM3 Grabbing)                                sugars
NP_006335= macrophage lectin 2                                    sugars
P07306=   Asialoglycoprotein receptor                             sugars
AAW40215= Macrophage antigen                                      unknown
AAF36830= CLEC1 (loc51267)                                        unknown
AAF36777= CLEC2 (loc51266)                                        unknown
AAG33923= dectin1                                                 unknown
NP_002534= OLR1                                                   oxLDL
NP_001772= CD69                                                   unknown
PT0372=   KLRC1 (NKG2A/B)                                         protein

*ITIM motif*
<u>Residues important for oxLDL binding</u>
Residues important for sugar binding

SEQUENCE LISTING

<160> NUMBER OF SEQ ID NOS: 34

<210> SEQ ID NO 1
<211> LENGTH: 628
<212> TYPE: DNA
<213> ORGANISM: Homo sapiens
<220> FEATURE:
<221> NAME/KEY: CDS
<222> LOCATION: (1)..(552)
<223> OTHER INFORMATION:

<400> SEQUENCE: 1

```
atg tct gaa gaa gtg acc tac gcg aca ctc aca ttt cag gat tct gct      48
Met Ser Glu Glu Val Thr Tyr Ala Thr Leu Thr Phe Gln Asp Ser Ala
1               5                   10                  15 gga gca agg aat aac cga gat gga aat aac cta aga aaa aga ggg cat      96
Gly Ala Arg Asn Asn Arg Asp Gly Asn Asn Leu Arg Lys Arg Gly His
                20                  25                  30 cca gct cca tct ccc att tgg cgt cat gct gct ctg ggt ctg gta act     144
Pro Ala Pro Ser Pro Ile Trp Arg His Ala Ala Leu Gly Leu Val Thr
            35                  40                  45 ctt tgc ctg atg ttg ctg att ggg ctg gtg acg ttg ggg atg atg ttt     192
Leu Cys Leu Met Leu Leu Ile Gly Leu Val Thr Leu Gly Met Met Phe
        50                  55                  60 ttg cag ata tct aat gac att aac tca gat tca gag aaa ttg agt caa     240
Leu Gln Ile Ser Asn Asp Ile Asn Ser Asp Ser Glu Lys Leu Ser Gln
65                  70                  75                  80 ctt cag aaa acc atc caa cag cag cag gat aac tta tcc cag caa ctg     288
Leu Gln Lys Thr Ile Gln Gln Gln Gln Asp Asn Leu Ser Gln Gln Leu
                85                  90                  95 ggc aac tcc aac aac ttg tcc atg gag gag gaa ttt ctc aag tca cag     336
Gly Asn Ser Asn Asn Leu Ser Met Glu Glu Glu Phe Leu Lys Ser Gln
                100                 105                 110 atc tcc agt cta ctg aag agg cag gaa caa atg gcc atc aaa ctg tgc     384
Ile Ser Ser Leu Leu Lys Arg Gln Glu Gln Met Ala Ile Lys Leu Cys
            115                 120                 125 caa gag cta atc att cat act tca gga ttt tct tat gtc aca gcc att     432
Gln Glu Leu Ile Ile His Thr Ser Gly Phe Ser Tyr Val Thr Ala Ile
        130                 135                 140 act cat gtt ttc gtt ctt ttg gct ggg att atc atg gga ctc ctc tgg     480
Thr His Val Phe Val Leu Leu Ala Gly Ile Ile Met Gly Leu Leu Trp
145                 150                 155                 160 cag aag ttg gtt ctg gga aga tgg ctc tgt tcc ctc tcc atc ctt cat     528
Gln Lys Leu Val Leu Gly Arg Trp Leu Cys Ser Leu Ser Ile Leu His
                165                 170                 175 gtt gtc aac gtt ttc tta aac tga ataataatca ctcatcttct gtcaaagatg    582
Val Val Asn Val Phe Leu Asn
                180 ccatgcttca gctgtgactc agcagttcct taaatcacaa acaatg                   628
```

<210> SEQ ID NO 2
<211> LENGTH: 183
<212> TYPE: PRT
<213> ORGANISM: Homo sapiens

<400> SEQUENCE: 2

Met Ser Glu Glu Val Thr Tyr Ala Thr Leu Thr Phe Gln Asp Ser Ala

```
                1               5                      10                      15
Gly Ala Arg Asn Asn Arg Asp Gly Asn Asn Leu Arg Lys Arg Gly His
                20                      25                      30

Pro Ala Pro Ser Pro Ile Trp Arg His Ala Ala Leu Gly Leu Val Thr
                35                      40                      45

Leu Cys Leu Met Leu Leu Ile Gly Leu Val Thr Leu Gly Met Met Phe
            50                      55                      60

Leu Gln Ile Ser Asn Asp Ile Asn Ser Asp Ser Glu Lys Leu Ser Gln
65                      70                      75                      80

Leu Gln Lys Thr Ile Gln Gln Gln Asp Asn Leu Ser Gln Gln Leu
                85                      90                      95

Gly Asn Ser Asn Asn Leu Ser Met Glu Glu Glu Phe Leu Lys Ser Gln
                100                     105                     110

Ile Ser Ser Leu Leu Lys Arg Gln Glu Gln Met Ala Ile Lys Leu Cys
                115                     120                     125

Gln Glu Leu Ile Ile His Thr Ser Gly Phe Ser Tyr Val Thr Ala Ile
                130                     135                     140

Thr His Val Phe Val Leu Leu Ala Gly Ile Ile Met Gly Leu Leu Trp
145                     150                     155                     160

Gln Lys Leu Val Leu Gly Arg Trp Leu Cys Ser Leu Ser Ile Leu His
                165                     170                     175

Val Val Asn Val Phe Leu Asn
                180

<210> SEQ ID NO 3
<211> LENGTH: 1266
<212> TYPE: DNA
<213> ORGANISM: Homo sapiens
<220> FEATURE:
<221> NAME/KEY: CDS
<222> LOCATION: (1)..(702)
<223> OTHER INFORMATION:

<400> SEQUENCE: 3 atg tct gaa gaa gtg acc tac gcg aca ctc aca ttt cag gat tct gct    48
Met Ser Glu Glu Val Thr Tyr Ala Thr Leu Thr Phe Gln Asp Ser Ala
1               5                       10                      15 gga gca agg aat aac cga gat gga aat aac cta aga aaa aga ggg cat    96
Gly Ala Arg Asn Asn Arg Asp Gly Asn Asn Leu Arg Lys Arg Gly His
                20                      25                      30 cca gct cca tct ccc att tgg cgt cat gct gct ctg ggt ctg gta act   144
Pro Ala Pro Ser Pro Ile Trp Arg His Ala Ala Leu Gly Leu Val Thr
                35                      40                      45 ctt tgc ctg atg ttg ctg att ggg ctg gtg acg ttg ggg atg atg ttt   192
Leu Cys Leu Met Leu Leu Ile Gly Leu Val Thr Leu Gly Met Met Phe
            50                      55                      60 ttg cag ata tct aat gac att aac tca gat tca gag aaa ttg agt caa   240
Leu Gln Ile Ser Asn Asp Ile Asn Ser Asp Ser Glu Lys Leu Ser Gln
65                      70                      75                      80 ctt cag aaa acc atc caa cag cag cag gat aac tta tcc cag caa ctg   288
Leu Gln Lys Thr Ile Gln Gln Gln Gln Asp Asn Leu Ser Gln Gln Leu
                85                      90                      95 ggc aac tcc aac aac ttg tcc atg gag gag gaa ttt ctc aag tca cag   336
Gly Asn Ser Asn Asn Leu Ser Met Glu Glu Glu Phe Leu Lys Ser Gln
                100                     105                     110 atc tcc agt cta ctg aag agg cag gaa caa atg gcc atc aaa ctg tgc   384
Ile Ser Ser Leu Leu Lys Arg Gln Glu Gln Met Ala Ile Lys Leu Cys
                115                     120                     125
```

```
caa gag cta atc att cat act tca gac cac aga tgt aat cca tgt cct    432
Gln Glu Leu Ile Ile His Thr Ser Asp His Arg Cys Asn Pro Cys Pro
            130                 135                 140 aag atg tgg caa tgg tac caa aat agt tgc tac tat ttt aca aca aat    480
Lys Met Trp Gln Trp Tyr Gln Asn Ser Cys Tyr Tyr Phe Thr Thr Asn
145                 150                 155                 160 gag gag aaa acc tgg gct aac agt aga aag gac tgc ata gac aag aac    528
Glu Glu Lys Thr Trp Ala Asn Ser Arg Lys Asp Cys Ile Asp Lys Asn
            165                 170                 175 tcc acc cta gtg aag ata gac agt ttg gaa gaa aag gat ttt ctt atg    576
Ser Thr Leu Val Lys Ile Asp Ser Leu Glu Glu Lys Asp Phe Leu Met
        180                 185                 190 tca cag cca tta ctc atg ttt tcg ttc ttt tgg ctg gga tta tca tgg    624
Ser Gln Pro Leu Leu Met Phe Ser Phe Phe Trp Leu Gly Leu Ser Trp
        195                 200                 205 gac tcc tct ggc aga agt tgg ttc tgg gaa gat ggc tct gtt ccc tct    672
Asp Ser Ser Gly Arg Ser Trp Phe Trp Glu Asp Gly Ser Val Pro Ser
        210                 215                 220 cca tcc ttc atg ttg tca acg ttt tct taa actgaataat aatcactcat     722
Pro Ser Phe Met Leu Ser Thr Phe Ser
225                 230 cttctgtcaa agatgccatg cttcagctgt gactcagcag ttccttaaat cacaaacaat    782
gatttagtac taaagaactt gaccagatca atggatccaa aggatgtgct tatttttcaaa   842 aaggaaatat ttatatttct cgctgtagtg ctgaaatttt ttggatttgc gagaagacag    902
ctgccccagt gaagactgag gatttggatt agtatgcttc ttccaaattc tccaagaagt    962
aagagacttg tgagtaagct catatgagga aagaggaaac tacggtacca gagccaaacc   1022
agcttttaaa atgactgtgt atttacatta tcagacaaat gaacttgttt aacagaacat   1082
tctccagttc cttgtctgac gtcttctgat ttgatgttat tattcggtct taaaattata   1142
cctggggaca aaggggaata gccatactat ggccctatga ttgtctcaga atcatttcac   1202
tgaatttctt tgctttctca aataaagact cctttctttc attattaaaa aaaaaaaaaa   1262
aaaa                                                                1266

<210> SEQ ID NO 4
<211> LENGTH: 233
<212> TYPE: PRT
<213> ORGANISM: Homo sapiens

<400> SEQUENCE: 4

Met Ser Glu Glu Val Thr Tyr Ala Thr Leu Thr Phe Gln Asp Ser Ala
1               5                   10                  15

Gly Ala Arg Asn Asn Arg Asp Gly Asn Asn Leu Arg Lys Arg Gly His
            20                  25                  30

Pro Ala Pro Ser Pro Ile Trp Arg His Ala Ala Leu Gly Leu Val Thr
        35                  40                  45

Leu Cys Leu Met Leu Leu Ile Gly Leu Val Thr Leu Gly Met Met Phe
    50                  55                  60

Leu Gln Ile Ser Asn Asp Ile Asn Ser Asp Ser Glu Lys Leu Ser Gln
65                  70                  75                  80

Leu Gln Lys Thr Ile Gln Gln Gln Asp Asn Leu Ser Gln Gln Leu
                85                  90                  95

Gly Asn Ser Asn Asn Leu Ser Met Glu Glu Glu Phe Leu Lys Ser Gln
            100                 105                 110

Ile Ser Ser Leu Leu Lys Arg Gln Glu Gln Met Ala Ile Lys Leu Cys
        115                 120                 125
```

-continued

```
Gln Glu Leu Ile Ile His Thr Ser Asp His Arg Cys Asn Pro Cys Pro
        130                 135                 140
Lys Met Trp Gln Trp Tyr Gln Asn Ser Cys Tyr Tyr Phe Thr Thr Asn
145                 150                 155                 160
Glu Glu Lys Thr Trp Ala Asn Ser Arg Lys Asp Cys Ile Asp Lys Asn
                165                 170                 175
Ser Thr Leu Val Lys Ile Asp Ser Leu Glu Glu Lys Asp Phe Leu Met
            180                 185                 190
Ser Gln Pro Leu Leu Met Phe Ser Phe Phe Trp Leu Gly Leu Ser Trp
        195                 200                 205
Asp Ser Ser Gly Arg Ser Trp Phe Trp Glu Asp Gly Ser Val Pro Ser
    210                 215                 220
Pro Ser Phe Met Leu Ser Thr Phe Ser
225                 230
```

<210> SEQ ID NO 5
<211> LENGTH: 1220
<212> TYPE: DNA
<213> ORGANISM: Homo sapiens
<220> FEATURE:
<221> NAME/KEY: CDS
<222> LOCATION: (37)..(735)
<223> OTHER INFORMATION:

<400> SEQUENCE: 5

```
ttaattagat aatttaaagt agcgttttct tctaca atg tct gaa gaa gtg acc       54
                                        Met Ser Glu Glu Val Thr
                                         1               5 tac gcg aca ctc aca ttt cag gat tct gct gga gca agg aat aac cga     102
Tyr Ala Thr Leu Thr Phe Gln Asp Ser Ala Gly Ala Arg Asn Asn Arg
         10                  15                  20 gat gga aat aac cta aga aaa aga ggg cat cca gct cca tct ccc att     150
Asp Gly Asn Asn Leu Arg Lys Arg Gly His Pro Ala Pro Ser Pro Ile
     25                  30                  35 tgg cgt cat gct gct ctg ggt ctg gta act ctt tgc ctg atg ttg ctg     198
Trp Arg His Ala Ala Leu Gly Leu Val Thr Leu Cys Leu Met Leu Leu
 40                  45                  50 att ggg ctg gtg acg ttg ggg atg atg ttt ttg cag ata tct aat gac     246
Ile Gly Leu Val Thr Leu Gly Met Met Phe Leu Gln Ile Ser Asn Asp
 55                  60                  65                  70 att aac tca gat tca gag aaa ttg agt caa ctt cag aaa acc atc caa     294
Ile Asn Ser Asp Ser Glu Lys Leu Ser Gln Leu Gln Lys Thr Ile Gln
                 75                  80                  85 cag cag cag gat aac tta tcc cag caa ctg ggc aac tcc aac aac ttg     342
Gln Gln Gln Asp Asn Leu Ser Gln Gln Leu Gly Asn Ser Asn Asn Leu
             90                  95                 100 tcc atg gag gag gaa ttt ctc aag tca cag atc tcc agt cta ctg aag     390
Ser Met Glu Glu Glu Phe Leu Lys Ser Gln Ile Ser Ser Leu Leu Lys
        105                 110                 115 agg cag gaa caa atg gcc atc aaa ctg tgc caa gag cta atc att cat     438
Arg Gln Glu Gln Met Ala Ile Lys Leu Cys Gln Glu Leu Ile Ile His
    120                 125                 130 act tca gac cac aga tgt aat cca tgt cct aag atg tgg caa tgg tac     486
Thr Ser Asp His Arg Cys Asn Pro Cys Pro Lys Met Trp Gln Trp Tyr
135                 140                 145                 150 caa aat agt tgc tac tat ttt aca aca aat gag gag aaa acc tgg gct     534
Gln Asn Ser Cys Tyr Tyr Phe Thr Thr Asn Glu Glu Lys Thr Trp Ala
                155                 160                 165 aac agt aga aag gac tgc ata gac aag aac tcc acc cta gtg aag ata     582
```

```
Asn Ser Arg Lys Asp Cys Ile Asp Lys Asn Ser Thr Leu Val Lys Ile
            170                 175                 180 gac agt ttg gaa gaa aag gat ttt ctt atg tca cag cca tta ctc atg      630
Asp Ser Leu Glu Glu Lys Asp Phe Leu Met Ser Gln Pro Leu Leu Met
        185                 190                 195 ttt tcg ttc ttt tgg ctg gga tta tca tgg gac tcc tct ggc aga agt      678
Phe Ser Phe Phe Trp Leu Gly Leu Ser Trp Asp Ser Ser Gly Arg Ser
200                 205                 210 tgg ttc tgg gaa gat ggc tct gtt ccc tct cca tcc ttg tac gtc tct      726
Trp Phe Trp Glu Asp Gly Ser Val Pro Ser Pro Ser Leu Tyr Val Ser
215                 220                 225                 230 aac tat tga ggatttagta ctaaagaact tgaccagatc aatggatcca              775
Asn Tyr aaggatgtgc ttattttcaa aaaggaaata tttatatttc tcgctgtagt gctgaaattt    835
tttggatttg cgagaagaca gctgccccag tgaagactga ggatttggat tagtatgctt    895
cttccaaatt ctccaagaag taagagactt gtgagtaagc tcatatgagg aaagaggaaa    955
ctacggtacc agagccaaac cagcttttaa aatgactgtg tatttacatt atcagacaaa    1015
tgaacttgtt taacagaaca ttctccagtt ccttgtctga cgtcttctga tttgatgtta    1075
ttattcggtc ttaaaattat acctggggac aaaggggaat agccatacta tggccctatg    1135
attgtctcag aatcatttca ctgaatttct ttgctttctc aaataaagac tccttctttt    1195
cattattaaa aaaaaaaaaa aaaaa                                          1220

<210> SEQ ID NO 6
<211> LENGTH: 232
<212> TYPE: PRT
<213> ORGANISM: Homo sapiens

<400> SEQUENCE: 6

Met Ser Glu Glu Val Thr Tyr Ala Thr Leu Thr Phe Gln Asp Ser Ala
1               5                   10                  15

Gly Ala Arg Asn Asn Arg Asp Gly Asn Asn Leu Arg Lys Arg Gly His
            20                  25                  30

Pro Ala Pro Ser Pro Ile Trp Arg His Ala Ala Leu Gly Leu Val Thr
        35                  40                  45

Leu Cys Leu Met Leu Leu Ile Gly Leu Val Thr Leu Gly Met Met Phe
    50                  55                  60

Leu Gln Ile Ser Asn Asp Ile Asn Ser Asp Ser Glu Lys Leu Ser Gln
65                  70                  75                  80

Leu Gln Lys Thr Ile Gln Gln Gln Asp Asn Leu Ser Gln Gln Leu
                85                  90                  95

Gly Asn Ser Asn Asn Leu Ser Met Glu Glu Phe Leu Lys Ser Gln
            100                 105                 110

Ile Ser Ser Leu Leu Lys Arg Gln Glu Gln Met Ala Ile Lys Leu Cys
        115                 120                 125

Gln Glu Leu Ile Ile His Thr Ser Asp His Arg Cys Asn Pro Cys Pro
    130                 135                 140

Lys Met Trp Gln Trp Tyr Gln Asn Ser Cys Tyr Tyr Phe Thr Thr Asn
145                 150                 155                 160

Glu Glu Lys Thr Trp Ala Asn Ser Arg Lys Asp Cys Ile Asp Lys Asn
                165                 170                 175

Ser Thr Leu Val Lys Ile Asp Ser Leu Glu Glu Lys Asp Phe Leu Met
            180                 185                 190

Ser Gln Pro Leu Leu Met Phe Ser Phe Phe Trp Leu Gly Leu Ser Trp
```

```
            195                 200                 205
Asp Ser Ser Gly Arg Ser Trp Phe Trp Glu Asp Gly Ser Val Pro Ser
    210                 215                 220

Pro Ser Leu Tyr Val Ser Asn Tyr
225                 230

<210> SEQ ID NO 7
<211> LENGTH: 771
<212> TYPE: DNA
<213> ORGANISM: Homo sapiens
<220> FEATURE:
<221> NAME/KEY: CDS
<222> LOCATION: (49)..(579)
<223> OTHER INFORMATION:

<400> SEQUENCE: 7
cactataggg cgaattgaat ttagcggccg cgaattcgcc cttctaca atg tct gaa         57
                                                     Met Ser Glu
                                                       1 gaa gtg acc tac gcg aca ctc aca ttt cag gat tct gct gga gca agg        105
Glu Val Thr Tyr Ala Thr Leu Thr Phe Gln Asp Ser Ala Gly Ala Arg
  5                  10                  15 aat aac cga gat gga aat aac cta aga aaa aga ggg cat cca gct cca        153
Asn Asn Arg Asp Gly Asn Asn Leu Arg Lys Arg Gly His Pro Ala Pro
 20                  25                  30                  35 tct ccc att tgg cgt cat gct gct ctg ggt ctg gta act ctt tgc ctg        201
Ser Pro Ile Trp Arg His Ala Ala Leu Gly Leu Val Thr Leu Cys Leu
                 40                  45                  50 atg ttg ctg att ggg ctg gtg acg ttg ggg atg atg ttt ttg cag ata        249
Met Leu Leu Ile Gly Leu Val Thr Leu Gly Met Met Phe Leu Gln Ile
             55                  60                  65 tct aat gac att aac tca gat tca gag aaa ttg agt caa ctt cag aaa        297
Ser Asn Asp Ile Asn Ser Asp Ser Glu Lys Leu Ser Gln Leu Gln Lys
         70                  75                  80 acc atc caa cag cag cag gat aac tta tcc cag caa ctg ggc aac tcc        345
Thr Ile Gln Gln Gln Gln Asp Asn Leu Ser Gln Gln Leu Gly Asn Ser
     85                  90                  95 aac aac ttg tcc atg gag gag gaa ttt ctc aag tca cag atc tcc agt        393
Asn Asn Leu Ser Met Glu Glu Glu Phe Leu Lys Ser Gln Ile Ser Ser
100                 105                 110                 115 cta ctg aag agg cag gaa caa atg gcc atc aaa ctg tgc caa gag cta        441
Leu Leu Lys Arg Gln Glu Gln Met Ala Ile Lys Leu Cys Gln Glu Leu
                120                 125                 130 atc att cat act tca gga ttt tct tat gtc aca gcc att act cat gtt        489
Ile Ile His Thr Ser Gly Phe Ser Tyr Val Thr Ala Ile Thr His Val
            135                 140                 145 ttc gtt ctt ttg gct ggg att atc atg gga ctc ctc tgg cag aag ttg        537
Phe Val Leu Leu Ala Gly Ile Ile Met Gly Leu Leu Trp Gln Lys Leu
        150                 155                 160 gtt ctg gga aga tgg ctc tgt tcc ctc tcc atc ctt tgc tga              579
Val Leu Gly Arg Trp Leu Cys Ser Leu Ser Ile Leu Cys
    165                 170                 175 aatttttttgg atttgcgaga agacagctgc cccagtgaag actgaggatt tggattagta    639
tgcttcttcc aaattctcca agaagtaaga gacttgtgag taagctcata tgaggaaaga    699
ggaaactacg gtaccagagc caaaccagca agggcgaatt cgtttaaacc tgcaggacta    759 gtcccttag tg                                                          771

<210> SEQ ID NO 8
<211> LENGTH: 176
```

<210> SEQ ID NO 9
<211> LENGTH: 1021
<212> TYPE: DNA
<213> ORGANISM: Homo sapiens
<220> FEATURE:
<221> NAME/KEY: CDS
<222> LOCATION: (101)..(844)
<223> OTHER INFORMATION:

<400> SEQUENCE: 9

```
ttttcccagt cacgacgttg taaaacgacg gccagtgaat tgtaatacga ctcactatag     60
ggcgaattga atttagcggc cgcgaattcg cccttctaca atg tct gaa gaa gtg    115
                                              Met Ser Glu Glu Val
                                              1               5 acc tac gcg aca ctc aca ttt cag gat tct gct gga gca agg aat aac    163
Thr Tyr Ala Thr Leu Thr Phe Gln Asp Ser Ala Gly Ala Arg Asn Asn
             10                  15                  20 cga gat gga aat aac cta aga aaa aga ggg cat cca gct cca tct ccc    211
Arg Asp Gly Asn Asn Leu Arg Lys Arg Gly His Pro Ala Pro Ser Pro
         25                  30                  35 att tgg cgt cat gct gct ctg ggt ctg gta act ctt tgc ctg atg ttg    259
Ile Trp Arg His Ala Ala Leu Gly Leu Val Thr Leu Cys Leu Met Leu
 40                  45                  50 ctg att ggg ctg gtg acg ttg ggg atg atg ttt ttg cag ata tct aat    307
Leu Ile Gly Leu Val Thr Leu Gly Met Met Phe Leu Gln Ile Ser Asn
     55                  60                  65 gac att aac tca gat tca gag aaa ttg agt caa ctt cag aaa acc atc    355
Asp Ile Asn Ser Asp Ser Glu Lys Leu Ser Gln Leu Gln Lys Thr Ile
 70                  75                  80                  85 caa cag cag cag gat aac tta tcc cag caa ctg ggc aac tcc aac aac    403
Gln Gln Gln Gln Asp Asn Leu Ser Gln Gln Leu Gly Asn Ser Asn Asn
             90                  95                 100
```

```
ttg tcc atg gag gag gaa ttt ctc aag tca cag atc tcc agt cta ctg       451
Leu Ser Met Glu Glu Glu Phe Leu Lys Ser Gln Ile Ser Ser Leu Leu
            105                 110                 115 aag agg cag gaa caa atg gcc atc aaa ctg tgc caa gag cta atc att       499
Lys Arg Gln Glu Gln Met Ala Ile Lys Leu Cys Gln Glu Leu Ile Ile
        120                 125                 130 tat act tca gac cac aga tgt aat cca tgt cct aag atg tgg caa tgg       547
Tyr Thr Ser Asp His Arg Cys Asn Pro Cys Pro Lys Met Trp Gln Trp
    135                 140                 145 tac caa aat agt tgc tac tat ttt aca aca aat gag gag aaa acc tgg       595
Tyr Gln Asn Ser Cys Tyr Tyr Phe Thr Thr Asn Glu Glu Lys Thr Trp
150                 155                 160                 165 gct aac agt aga aag gac tgc ata gac aag aac tcc acc cta gtg aag       643
Ala Asn Ser Arg Lys Asp Cys Ile Asp Lys Asn Ser Thr Leu Val Lys
                170                 175                 180 ata gac agt ttg gaa gaa aag gat ttt ctt atg tca cag cca tta ctc       691
Ile Asp Ser Leu Glu Glu Lys Asp Phe Leu Met Ser Gln Pro Leu Leu
            185                 190                 195 atg ttt tcg ttc ttt tgg ctg gga tta tca tgg gac tcc tct ggc aga       739
Met Phe Ser Phe Phe Trp Leu Gly Leu Ser Trp Asp Ser Ser Gly Arg
        200                 205                 210 agt tgg ttc tgg gaa gat ggc tct gtt ccc tct cca tcc ttt gct gaa       787
Ser Trp Phe Trp Glu Asp Gly Ser Val Pro Ser Pro Ser Phe Ala Glu
    215                 220                 225 att ttt tgg att tgc gag aag aca gct gcc cca gtg aag act gag gat       835
Ile Phe Trp Ile Cys Glu Lys Thr Ala Ala Pro Val Lys Thr Glu Asp
230                 235                 240                 245 ttg gat tag tatgcttctt ccaaattctc caagaagtaa gagacttgtg              884
Leu Asp agtaagctca tatgaggaaa gaggaaacta cggtaccaga gccaaaccag caagggcgaa    944
ttcgtttaaa cctgcaggac tagtcccttt agtgagggtt aattctgagc ttggcgtaat   1004
catggtcata gctgttt                                                  1021

<210> SEQ ID NO 10
<211> LENGTH: 247
<212> TYPE: PRT
<213> ORGANISM: Homo sapiens

<400> SEQUENCE: 10

Met Ser Glu Glu Val Thr Tyr Ala Thr Leu Thr Phe Gln Asp Ser Ala
1               5                   10                  15

Gly Ala Arg Asn Asn Arg Asp Gly Asn Asn Leu Arg Lys Arg Gly His
            20                  25                  30

Pro Ala Pro Ser Pro Ile Trp Arg His Ala Ala Leu Gly Leu Val Thr
        35                  40                  45

Leu Cys Leu Met Leu Leu Ile Gly Leu Val Thr Leu Gly Met Met Phe
    50                  55                  60

Leu Gln Ile Ser Asn Asp Ile Asn Ser Asp Ser Glu Lys Leu Ser Gln
65                  70                  75                  80

Leu Gln Lys Thr Ile Gln Gln Gln Asp Asn Leu Ser Gln Gln Leu
                85                  90                  95

Gly Asn Ser Asn Asn Leu Ser Met Glu Glu Glu Phe Leu Lys Ser Gln
            100                 105                 110

Ile Ser Ser Leu Leu Lys Arg Gln Glu Gln Met Ala Ile Lys Leu Cys
        115                 120                 125

Gln Glu Leu Ile Ile Tyr Thr Ser Asp His Arg Cys Asn Pro Cys Pro
```

```
            130                 135                 140
Lys Met Trp Gln Trp Tyr Gln Asn Ser Cys Tyr Tyr Phe Thr Thr Asn
145                 150                 155                 160

Glu Glu Lys Thr Trp Ala Asn Ser Arg Lys Asp Cys Ile Asp Lys Asn
                165                 170                 175

Ser Thr Leu Val Lys Ile Asp Ser Leu Glu Glu Lys Asp Phe Leu Met
            180                 185                 190

Ser Gln Pro Leu Leu Met Phe Ser Phe Phe Trp Leu Gly Leu Ser Trp
        195                 200                 205

Asp Ser Ser Gly Arg Ser Trp Phe Trp Glu Asp Gly Ser Val Pro Ser
    210                 215                 220

Pro Ser Phe Ala Glu Ile Phe Trp Ile Cys Glu Lys Thr Ala Ala Pro
225                 230                 235                 240

Val Lys Thr Glu Asp Leu Asp
                245

<210> SEQ ID NO 11
<211> LENGTH: 1012
<212> TYPE: DNA
<213> ORGANISM: Homo sapiens
<220> FEATURE:
<221> NAME/KEY: CDS
<222> LOCATION: (49)..(879)
<223> OTHER INFORMATION:

<400> SEQUENCE: 11
cactataggg cgaattgaat ttagcggccg cgaattcgcc cttctaca atg tct gaa        57
                                                    Met Ser Glu
                                                      1 gaa gtg acc tac gcg aca ctc aca ttt cag gat tct gct gga gca agg       105
Glu Val Thr Tyr Ala Thr Leu Thr Phe Gln Asp Ser Ala Gly Ala Arg
      5                  10                  15 aat aac cga gat gga aat aac cta aga aaa aga ggg cat cca gct cca       153
Asn Asn Arg Asp Gly Asn Asn Leu Arg Lys Arg Gly His Pro Ala Pro
 20                  25                  30                  35 tct ccc att tgg cgt cat gct gct ctg ggt ctg gta act ctt tgc ctg       201
Ser Pro Ile Trp Arg His Ala Ala Leu Gly Leu Val Thr Leu Cys Leu
                 40                  45                  50 atg ttg ctg att ggg ctg gtg aca ttg ggg atg atg ttt ttg cag ata       249
Met Leu Leu Ile Gly Leu Val Thr Leu Gly Met Met Phe Leu Gln Ile
             55                  60                  65 tct aat gac att aac tca gat tca gag aaa ttg agt caa ctt cag aaa       297
Ser Asn Asp Ile Asn Ser Asp Ser Glu Lys Leu Ser Gln Leu Gln Lys
         70                  75                  80 acc atc caa cag cag cag gat aac tta tcc cag caa ctg ggc aac tcc       345
Thr Ile Gln Gln Gln Gln Asp Asn Leu Ser Gln Gln Leu Gly Asn Ser
     85                  90                  95 aac aac ttg tcc atg gag gag gaa ttt ctc aag tca cag atc tcc agt       393
Asn Asn Leu Ser Met Glu Glu Glu Phe Leu Lys Ser Gln Ile Ser Ser
100                 105                 110                 115 gta ctg aag agg cag gaa caa atg gcc atc aaa ctg tgc caa gag cta       441
Val Leu Lys Arg Gln Glu Gln Met Ala Ile Lys Leu Cys Gln Glu Leu
                120                 125                 130 atc att cat act tca gac cac aga tgt aat cca tgt cct aag atg tgg       489
Ile Ile His Thr Ser Asp His Arg Cys Asn Pro Cys Pro Lys Met Trp
            135                 140                 145 caa tgg tac caa aat agt tgc tac tat ttt aca aca aat gag gag aaa       537
Gln Trp Tyr Gln Asn Ser Cys Tyr Tyr Phe Thr Thr Asn Glu Glu Lys
        150                 155                 160
```

```
acc tgg gct aac agt aga aag gac tgc ata gac aag aac tcc acc cta    585
Thr Trp Ala Asn Ser Arg Lys Asp Cys Ile Asp Lys Asn Ser Thr Leu
    165                 170                 175 gtg aag ata gac agt ttg gaa gaa aag gat ttt ctt atg tca cag cca    633
Val Lys Ile Asp Ser Leu Glu Glu Lys Asp Phe Leu Met Ser Gln Pro
180                 185                 190                 195 tta ctc atg ttt tcg ttc ttt tgg ctg gga tta tca tgg gac tcc tct    681
Leu Leu Met Phe Ser Phe Phe Trp Leu Gly Leu Ser Trp Asp Ser Ser
                200                 205                 210 ggc aga agt tgg ttc tgg gaa gat ggc tct gtt ccc tct cca tcc tta    729
Gly Arg Ser Trp Phe Trp Glu Asp Gly Ser Val Pro Ser Pro Ser Leu
            215                 220                 225 ttt agt act aaa gaa ctt gac cag atc aat gga tcc aaa gga tgt gct    777
Phe Ser Thr Lys Glu Leu Asp Gln Ile Asn Gly Ser Lys Gly Cys Ala
        230                 235                 240 tat ttt caa aaa gga aat att tat att tct cgc tgt agt gct gaa att    825
Tyr Phe Gln Lys Gly Asn Ile Tyr Ile Ser Arg Cys Ser Ala Glu Ile
    245                 250                 255 ttt tgg att tgc gag aag aca gcc gcc cca gtg aag act gag gat ttg    873
Phe Trp Ile Cys Glu Lys Thr Ala Ala Pro Val Lys Thr Glu Asp Leu
260                 265                 270                 275 gat tag tatgcttctt ccaaattctc caagaagtaa gagacttgtg agtaagctca      929
Asp tatgaggaaa gaggaaacta cggtaccaga gccaaaccag caagggcgaa ttcgtttaaa    989
cctgcaggac tagtcccttt agt                                          1012

<210> SEQ ID NO 12
<211> LENGTH: 276
<212> TYPE: PRT
<213> ORGANISM: Homo sapiens

<400> SEQUENCE: 12

Met Ser Glu Glu Val Thr Tyr Ala Thr Leu Thr Phe Gln Asp Ser Ala
1               5                   10                  15

Gly Ala Arg Asn Asn Arg Asp Gly Asn Asn Leu Arg Lys Arg Gly His
            20                  25                  30

Pro Ala Pro Ser Pro Ile Trp Arg His Ala Ala Leu Gly Leu Val Thr
        35                  40                  45

Leu Cys Leu Met Leu Leu Ile Gly Leu Val Thr Leu Gly Met Met Phe
    50                  55                  60

Leu Gln Ile Ser Asn Asp Ile Asn Ser Asp Ser Glu Lys Leu Ser Gln
65                  70                  75                  80

Leu Gln Lys Thr Ile Gln Gln Gln Asp Asn Leu Ser Gln Gln Leu
                85                  90                  95

Gly Asn Ser Asn Asn Leu Ser Met Glu Glu Phe Leu Lys Ser Gln
            100                 105                 110

Ile Ser Ser Val Leu Lys Arg Gln Glu Gln Met Ala Ile Lys Leu Cys
        115                 120                 125

Gln Glu Leu Ile Ile His Thr Ser Asp His Arg Cys Asn Pro Cys Pro
    130                 135                 140

Lys Met Trp Gln Trp Tyr Gln Asn Ser Cys Tyr Tyr Phe Thr Thr Asn
145                 150                 155                 160

Glu Glu Lys Thr Trp Ala Asn Ser Arg Lys Asp Cys Ile Asp Lys Asn
                165                 170                 175

Ser Thr Leu Val Lys Ile Asp Ser Leu Glu Glu Lys Asp Phe Leu Met
            180                 185                 190
```

```
Ser Gln Pro Leu Leu Met Phe Ser Phe Phe Trp Leu Gly Leu Ser Trp
        195                 200                 205

Asp Ser Ser Gly Arg Ser Trp Phe Trp Glu Asp Gly Ser Val Pro Ser
        210                 215                 220

Pro Ser Leu Phe Ser Thr Lys Glu Leu Asp Gln Ile Asn Gly Ser Lys
225                 230                 235                 240

Gly Cys Ala Tyr Phe Gln Lys Gly Asn Ile Tyr Ile Ser Arg Cys Ser
                245                 250                 255

Ala Glu Ile Phe Trp Ile Cys Glu Lys Thr Ala Ala Pro Val Lys Thr
            260                 265                 270

Glu Asp Leu Asp
        275

<210> SEQ ID NO 13
<211> LENGTH: 546
<212> TYPE: DNA
<213> ORGANISM: Homo sapiens
<220> FEATURE:
<221> NAME/KEY: CDS
<222> LOCATION: (1)..(537)
<223> OTHER INFORMATION:

<400> SEQUENCE: 13 atg tct gaa gaa gtg acc tac gcg aca ctc aca ttt cag gat tct gct    48
Met Ser Glu Glu Val Thr Tyr Ala Thr Leu Thr Phe Gln Asp Ser Ala
1               5                   10                  15 gga gca agg aat aac cga gat gga aat aac cta aga aaa aga ggg cat    96
Gly Ala Arg Asn Asn Arg Asp Gly Asn Asn Leu Arg Lys Arg Gly His
            20                  25                  30 cca gct cca tct ccc att tgg cgt cat gct gct ctg ggt ctg gta act   144
Pro Ala Pro Ser Pro Ile Trp Arg His Ala Ala Leu Gly Leu Val Thr
        35                  40                  45 ctt tgc ctg atg ttg ctg att ggg ctg gtg acg ttg ggg atg atg ttt   192
Leu Cys Leu Met Leu Leu Ile Gly Leu Val Thr Leu Gly Met Met Phe
    50                  55                  60 ttg cag ata tct aat gac att aac tca gat tca gag aaa ttg agt caa   240
Leu Gln Ile Ser Asn Asp Ile Asn Ser Asp Ser Glu Lys Leu Ser Gln
65                  70                  75                  80 ctt cag aaa acc atc caa cag cag cag gat aac tta tcc cag caa ctg   288
Leu Gln Lys Thr Ile Gln Gln Gln Gln Asp Asn Leu Ser Gln Gln Leu
                85                  90                  95 ggc aac tcc aac aac ttg tcc atg gag gag gaa ttt ctc aag tca cag   336
Gly Asn Ser Asn Asn Leu Ser Met Glu Glu Glu Phe Leu Lys Ser Gln
            100                 105                 110 atc tcc agt cta ctg aag agg cag gaa caa atg gcc atc aaa ctg tgc   384
Ile Ser Ser Leu Leu Lys Arg Gln Glu Gln Met Ala Ile Lys Leu Cys
        115                 120                 125 caa gag cta att att cat act tca gga ttt tct tat gtc aca gcc att   432
Gln Glu Leu Ile Ile His Thr Ser Gly Phe Ser Tyr Val Thr Ala Ile
    130                 135                 140 act cat gtt ttc gtt ctt ttg gct ggg att atc atg gga ctc ctc tgg   480
Thr His Val Phe Val Leu Leu Ala Gly Ile Ile Met Gly Leu Leu Trp
145                 150                 155                 160 cag aag ttg gtt ctg gga aga tgg ctc tgt ccc ctc tcc atc ctt gta   528
Gln Lys Leu Val Leu Gly Arg Trp Leu Cys Ser Leu Ser Ile Leu Val
                165                 170                 175 cgt ctc taa ctattgagg                                             546
Arg Leu

<210> SEQ ID NO 14
```

<211> LENGTH: 178
<212> TYPE: PRT
<213> ORGANISM: Homo sapiens

<400> SEQUENCE: 14

```
Met Ser Glu Glu Val Thr Tyr Ala Thr Leu Thr Phe Gln Asp Ser Ala
1               5                   10                  15

Gly Ala Arg Asn Asn Arg Asp Gly Asn Asn Leu Arg Lys Arg Gly His
                20                  25                  30

Pro Ala Pro Ser Pro Ile Trp Arg His Ala Ala Leu Gly Leu Val Thr
            35                  40                  45

Leu Cys Leu Met Leu Leu Ile Gly Leu Val Thr Leu Gly Met Met Phe
        50                  55                  60

Leu Gln Ile Ser Asn Asp Ile Asn Ser Asp Ser Glu Lys Leu Ser Gln
65                  70                  75                  80

Leu Gln Lys Thr Ile Gln Gln Gln Asp Asn Leu Ser Gln Gln Leu
                85                  90                  95

Gly Asn Ser Asn Asn Leu Ser Met Glu Glu Phe Leu Lys Ser Gln
                100                 105                 110

Ile Ser Ser Leu Leu Lys Arg Gln Glu Gln Met Ala Ile Lys Leu Cys
                115                 120                 125

Gln Glu Leu Ile Ile His Thr Ser Gly Phe Ser Tyr Val Thr Ala Ile
        130                 135                 140

Thr His Val Phe Val Leu Leu Ala Gly Ile Ile Met Gly Leu Leu Trp
145                 150                 155                 160

Gln Lys Leu Val Leu Gly Arg Trp Leu Cys Ser Leu Ser Ile Leu Val
                165                 170                 175

Arg Leu
```

<210> SEQ ID NO 15
<211> LENGTH: 973
<212> TYPE: DNA
<213> ORGANISM: Homo sapiens
<220> FEATURE:
<221> NAME/KEY: CDS
<222> LOCATION: (164)..(694)
<223> OTHER INFORMATION:

<400> SEQUENCE: 15

```
cactaaaggg actagtcctg caggtttaaa cgaattcgcc cttgtgtctg ggtcagctga      60
gtgactacat caaagctccc agccttgaaa aacacatgct gttcccaggc ctcaagatat     120
tgaaacatta attagataat ttaaagtagc gttttcttct aca atg tct gaa gaa       175
                                                Met Ser Glu Glu
                                                1 gtg acc tac gcg aca ctc aca ttt cag gat tct gct gga gca agg aat       223
Val Thr Tyr Ala Thr Leu Thr Phe Gln Asp Ser Ala Gly Ala Arg Asn
5                   10                  15                  20 aac cga gat gga aat aac cta aga aaa aga ggg cat cca gct cca tct       271
Asn Arg Asp Gly Asn Asn Leu Arg Lys Arg Gly His Pro Ala Pro Ser
                25                  30                  35 ccc att tgg cgt cat gct gct ctg ggt ctg gta act ctt tgc ctg atg       319
Pro Ile Trp Arg His Ala Ala Leu Gly Leu Val Thr Leu Cys Leu Met
            40                  45                  50 ttg ctg att ggg ctg gtg acg ttg ggg atg atg ttt ttg cag ata tct       367
Leu Leu Ile Gly Leu Val Thr Leu Gly Met Met Phe Leu Gln Ile Ser
        55                  60                  65 aat gac att aac tca gat tca gag aaa ttg agt caa ctt cag aaa acc       415
Asn Asp Ile Asn Ser Asp Ser Glu Lys Leu Ser Gln Leu Gln Lys Thr
```

-continued

```
                    70                  75                  80
atc caa cag cag cag gat aac tta tcc cag caa ctg ggc aac tcc aac     463
Ile Gln Gln Gln Gln Asp Asn Leu Ser Gln Gln Leu Gly Asn Ser Asn
 85                  90                  95                 100 aac ttg tcc atg gag gag gaa ttt ctc aag tca cag atc tcc agt cta     511
Asn Leu Ser Met Glu Glu Glu Phe Leu Lys Ser Gln Ile Ser Ser Leu
                105                 110                 115 ctg aag agg cag gaa caa atg gcc atc aaa ctg tgc caa gag cta atc     559
Leu Lys Arg Gln Glu Gln Met Ala Ile Lys Leu Cys Gln Glu Leu Ile
            120                 125                 130 att cat act tca gga ttt tct tat gtc aca gcc att act cat gtt ttc     607
Ile His Thr Ser Gly Phe Ser Tyr Val Thr Ala Ile Thr His Val Phe
        135                 140                 145 gtt ctt ttg gct ggg atc atc atg gga ctc ctc tgg cag aag ttg gtt     655
Val Leu Leu Ala Gly Ile Ile Met Gly Leu Leu Trp Gln Lys Leu Val
    150                 155                 160 ctg gga aga tgg ctc tgt tcc ctc tcc atc ctt att tag tactaaagaa     704
Leu Gly Arg Trp Leu Cys Ser Leu Ser Ile Leu Ile
165                 170                 175 cttgaccaga tcaatggatc caaaggatgt gcttattttc aaaaaggaaa tatttatatt     764
tctcgctgta gtgctgaaat tttttggatt tgcgagaaga cagctgcccc agtgaagact     824
gaggatttgg attagtatgc ttcttccaaa ttctccaaga agtaagagac ttgtgagtaa     884
gctcatatga ggaaagagga aactacggta ccagagccaa accagcaagg gcgaattcgc     944
ggccgctaaa ttcaattcgc cctatagtg                                       973

<210> SEQ ID NO 16
<211> LENGTH: 176
<212> TYPE: PRT
<213> ORGANISM: Homo sapiens

<400> SEQUENCE: 16

Met Ser Glu Glu Val Thr Tyr Ala Thr Leu Thr Phe Gln Asp Ser Ala
  1               5                  10                  15

Gly Ala Arg Asn Asn Arg Asp Gly Asn Asn Leu Arg Lys Arg Gly His
             20                  25                  30

Pro Ala Pro Ser Pro Ile Trp Arg His Ala Ala Leu Gly Leu Val Thr
         35                  40                  45

Leu Cys Leu Met Leu Leu Ile Gly Leu Val Thr Leu Gly Met Met Phe
     50                  55                  60

Leu Gln Ile Ser Asn Asp Ile Asn Ser Asp Ser Glu Lys Leu Ser Gln
 65                  70                  75                  80

Leu Gln Lys Thr Ile Gln Gln Gln Asp Asn Leu Ser Gln Gln Leu
                 85                  90                  95

Gly Asn Ser Asn Asn Leu Ser Met Glu Glu Glu Phe Leu Lys Ser Gln
            100                 105                 110

Ile Ser Ser Leu Leu Lys Arg Gln Glu Gln Met Ala Ile Lys Leu Cys
        115                 120                 125

Gln Glu Leu Ile Ile His Thr Ser Gly Phe Ser Tyr Val Thr Ala Ile
    130                 135                 140

Thr His Val Phe Val Leu Leu Ala Gly Ile Ile Met Gly Leu Leu Trp
145                 150                 155                 160

Gln Lys Leu Val Leu Gly Arg Trp Leu Cys Ser Leu Ser Ile Leu Ile
                165                 170                 175

<210> SEQ ID NO 17
```

```
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(6)
<223> OTHER INFORMATION: Xaa at position 1 is I or V;  Xaa at position
      2,4, and 5 is any amino acid;  Xaa at position 6 is L or V

<400> SEQUENCE: 17

Xaa Xaa Tyr Xaa Xaa Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: Peptide Linker Sequence

<400> SEQUENCE: 18

Gly Gly Gly Gly Ser
1               5

<210> SEQ ID NO 19
<211> LENGTH: 12
<212> TYPE: PRT
<213> ORGANISM: Artificial Sequence
<220> FEATURE:
<223> OTHER INFORMATION: Peptide Linker Sequence

<400> SEQUENCE: 19

Gly Lys Ser Ser Gly Ser Gly Ser Glu Ser Lys Ser
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Peptide Linker Sequence

<400> SEQUENCE: 20

Gly Ser Thr Ser Gly Ser Gly Lys Ser Ser Glu Gly Ser Gly Ser Thr
1               5                   10                  15

Lys Gly

<210> SEQ ID NO 21
<211> LENGTH: 18
<212> TYPE: PRT
<213> ORGANISM: Artificial Sequence
<220> FEATURE:
<223> OTHER INFORMATION: Peptide Linker Sequence

<400> SEQUENCE: 21

Gly Ser Thr Ser Gly Ser Gly Lys Ser Ser Glu Gly Ser Gly Ser Thr
1               5                   10                  15

Lys Gly

<210> SEQ ID NO 22
<211> LENGTH: 18
<212> TYPE: PRT
<213> ORGANISM: Artificial Sequence
<220> FEATURE:
<223> OTHER INFORMATION: Peptide Linker Sequence
```

<400> SEQUENCE: 22

Gly Ser Thr Ser Gly Ser Gly Lys Pro Gly Ser Gly Glu Gly Ser Thr
1               5                   10                  15

Lys Gly

<210> SEQ ID NO 23
<211> LENGTH: 14
<212> TYPE: PRT
<213> ORGANISM: Artificial Sequence
<220> FEATURE:
<223> OTHER INFORMATION: Peptide Linker Sequence

<400> SEQUENCE: 23

Glu Gly Lys Ser Ser Gly Ser Gly Ser Glu Ser Lys Glu Phe
1               5                   10

<210> SEQ ID NO 24
<211> LENGTH: 5
<212> TYPE: PRT
<213> ORGANISM: Artificial Sequence
<220> FEATURE:
<223> OTHER INFORMATION: Localization Sequence

<400> SEQUENCE: 24

Lys Lys Lys Arg Lys
1               5

<210> SEQ ID NO 25
<211> LENGTH: 26
<212> TYPE: PRT
<213> ORGANISM: Artificial Sequence
<220> FEATURE:
<223> OTHER INFORMATION: Localization Sequence

<400> SEQUENCE: 25

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 26
<211> LENGTH: 4
<212> TYPE: PRT
<213> ORGANISM: Artificial Sequence
<220> FEATURE:
<223> OTHER INFORMATION: Localization Sequence

<400> SEQUENCE: 26

Lys Asp Glu Leu
1

<210> SEQ ID NO 27
<211> LENGTH: 4
<212> TYPE: PRT
<213> ORGANISM: Artificial Sequence
<220> FEATURE:
<223> OTHER INFORMATION: Localization Sequence
<220> FEATURE:
<221> NAME/KEY: MISC_FEATURE
<222> LOCATION: (4)..(4)
<223> OTHER INFORMATION: Xaa at position 4 is any amino acid

<400> SEQUENCE: 27

Cys Ala Ala Xaa
1

```
<210> SEQ ID NO 28
<211> LENGTH: 4
<212> TYPE: PRT
<213> ORGANISM: Artificial Sequence
<220> FEATURE:
<223> OTHER INFORMATION: Localization Sequence
<220> FEATURE:
<221> NAME/KEY: MISC_FEATURE
<222> LOCATION: (3)..(4)
<223> OTHER INFORMATION: Xaa at positions 3 and 4 can be any amino acid

<400> SEQUENCE: 28

Cys Cys Xaa Xaa
1

<210> SEQ ID NO 29
<211> LENGTH: 21
<212> TYPE: DNA
<213> ORGANISM: Artificial sequence
<220> FEATURE:
<223> OTHER INFORMATION: Primer

<400> SEQUENCE: 29
gggaatcggg atggaaataa c                                              21

<210> SEQ ID NO 30
<211> LENGTH: 16
<212> TYPE: DNA
<213> ORGANISM: Artificial Sequence
<220> FEATURE:
<223> OTHER INFORMATION: Primer

<400> SEQUENCE: 30
gcgcctcgcc aaagtg                                                    16

<210> SEQ ID NO 31
<211> LENGTH: 18
<212> TYPE: DNA
<213> ORGANISM: Artificial Sequence
<220> FEATURE:
<223> OTHER INFORMATION: Probe

<400> SEQUENCE: 31
aagaaggaca cccagctc                                                  18

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
agtgtactga agaggcagga acaa                                           24

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
gacatggatt acatctgtgg tctga                                          25
```

```
<210> SEQ ID NO 34
<211> LENGTH: 24
<212> TYPE: DNA
<213> ORGANISM: Artificial Sequence
<220> FEATURE:
<223> OTHER INFORMATION: Probe

<400> SEQUENCE: 34
tggccatcaa actgtgccaa gagc                                              24
```

POLYNUCLEOTIDES ENCODING C-TYPE LECTIN POLYPEPTIDES AND METHODS OF USE THEREOF

CROSS-REFERENCE TO RELATED APPLICATIONS

This application is a divisional application of U.S. application Ser. No. 10/499,184, flied Jun. 17, 2004, now U.S. Pat. No. 7.396.662, which is a national stage filing under 35 U.S.C. §371 of international application PCT/US02/41158, flied Dec. 19, 2002, which claims the benefit of U.S. provisional application Ser. No. 60/342,001, filed Dec. 19, 2001, the entire disclosure of which is relied upon and incorporated by reference herein.

FIELD OF THE INVENTION

The invention is directed to novel substantially purified polypeptides of the C-type lectin family of polypeptides and soluble fragments thereof, polynucleotides encoding such polypeptides and fragments, processes for production of recombinant forms of such polypeptides and fragments, antibodies generated against these polypeptides or fragments, and assays and methods employing these polypeptides, antibodies, and polynucleotides.

BACKGROUND

Calcium-dependent lectins (C-type lectins) are expressed in a large number of cell types including macrophages, B- and T-lymphocytes, mast cells, and natural killer (NK) cells. Macrophage lectin proteins perform a variety of functions in the recognition and destruction of foreign cells and pathogens. Gram positive and Gram negative bacteria have been shown to interact with C-type lectins (Athamna et al., Infect Immun 59:1673, 1991; Shimaoka et al., J. Immunol. 166(8):5108, 2001). A human macrophage C-type lectin has been found to recognize Tn Ag, a well-known human carcinoma-associated epitope (Suzuki et al., J Immunol 156:128, 1996). Furthermore, the recombinant cytosolic carbohydrate binding domain of the mouse macrophage C-type lectin also served as an inhibitor of cytotoxic activity, indicating that the lectin was a direct mediator of the macrophage tumoricidal response (Imai et al., J Immunol Methods 171:23, 1994). Unique macrophage lectins may specifically interact with surface antigens expressed by certain abnormal or diseased cells. The lectins may direct the macrophages to abnormal or diseased cells.

Conserved features of C-type lectins include an extracellular carbohydrate recognition domain (Spiess, M Biochem 29:10009, 1990). Receptor proteins of the C-type lectin superfamily do not generally share significant sequence homology beyond that of the carbohydrate recognition domain. C-type lectins are typically Type II membrane proteins. Type II membrane proteins include an extracellular C-terminus that has the carbohydrate binding domain, an amino terminal cytoplasmic domain, and a membrane-spanning domain of approximately 20 residues. Several prolines generally precede the cytoplasmic domain of the transmembrane domain. The prolines are thought to prevent steric interference of the amino-terminal domain with the transmembrane domain during membrane insertion. The N-terminal cytosolic domains of the C-type lectins are very diverse in both length and sequence. Phosphorylation of tyrosine in the cytosolic domain of the asialoglycoprotein receptor, a C-type lectin, has been demonstrated (Fallon, J Biol Chem 265:3401, 1990). The extracellular carbohydrate binding domains can be separated from membrane-bound C-type lectin molecules by protease treatment. These isolated, soluble domains retain structural integrity and carbohydrate binding activity, owing in part to the three-intrachain disulfide bonds present in the binding domains of this class of lectin.

C-type lectins play a role in the recognition and destruction of diseased and non-self cells. The selective modulation of the expression and specificity of novel C-type lectins may allow the successful management of diseases related to macrophage function, such as graft rejection or pathogen colonization, or the exploitation of the natural cytolytic capabilities of macrophages, such as specific targeting to tumors or infected host cells.

A number of groups have identified several new C-type lectins unique to macrophages and DC, such as the murine macrophage-restricted C-type lectin (mMCL) (Balch, S., et al., *J. Biol. Chem.* 273:18656-64, 1998); Langerin, the Langerhans cell-specific C-type lectin (Valladeau, J., *Immunity* 12:71-81, 2000); Mincle, a macrophage-inducible C-type lectin that is a transcriptional target of NF-IL6 in murine peritoneal macrophages (Matsumoto, M., et al., J. Immunol. 163:5039-48, 1999); DCIR, the human dendritic cell immumoreceptor, a type II glycoprotein with homology to the macrophage lectin and hepatic asialoglycoprotein receptors (Bates, E., et al., J. Immunol. 163:1973-83, 1999 and U.S. Pat. No. 6,277,959, both of which are incorporated herein by reference); and, murine Dectin-1 and Dectin-2 (DC-associated C-type lectins; Ariizumi, K., et al., *J. Biol. Chem.*, 275:20157-167, 2000 and Ariizumi, K., et al., *J. Biol. Chem.*, 275:11957-963, 2000, respectively), which are thought to be involved in delivering T-cell costimulatory signals.

The present invention identifies additional, novel C-type lectin polypeptides.

SUMMARY OF THE INVENTION

The present invention relates to a novel human C-type lectin, referred to herein as a C-type lectin-like (CtLL) polypeptide or polynucleotide.

The invention provides a substantially purified polypeptide comprising a sequence that is at least 80% identical to a sequence as set forth in SEQ ID NO: 2, 4, 6, 8, 10, 12, 14, and/or 16 and having oxidized lipid and/or carbohydrate binding activity; a polypeptide comprising a soluble fragment of any one of these having carbohydrate binding activity; a polypeptide comprising a soluble fragment of any one of these having oxidized lipid binding activity; and a polypeptide comprising a fragment of any of one these having a lectin domain amino acid sequence.

The invention further provides a substantially purified soluble polypeptide comprising a sequence that is at least 80% identical to a sequence selected from the group consisting of: from about residue 1 to about 41 of SEQ ID NO:2, 4, 6, 8, 10, 12, 14, or 16; from about residue 66 to about 136 of SEQ ID NO:2, 8, 14, or 16; from about residue $x_1$ to about $x_2$ of SEQ ID NO:4, wherein $x_1$ is a residue between and including residues 66 and 143 and $x_2$ is a residue between and including residue 226 and 233; from about residue $x_1$ to about $x_2$ of SEQ ID NO:6, wherein $x_1$ is a residue between and including residues 66 and 143 and $x_2$ is a residue between and including residue 227 and 232; from about residue $x_1$ to about 247 of SEQ ID NO:10, wherein $x_1$ is a residue between and including about residues 66 and 142; and from about residue $x_1$ to about 276 of SEQ ID NO:12, wherein $x_1$ is a residue between and including residues 66 and 142, wherein the soluble fragment comprises oxidized lipid and/or carbohydrate binding activity.

The invention also provides a fusion polypeptide comprising a polypeptide of the invention operably linked to a leucine zipper polypeptide, an Fc polypeptide, or a peptide linker.

The invention provides polynucleotides encoding the polypeptides and fusion polypeptides of the invention. In one embodiment, the polynucleotide is selected from the group consisting of: a polynucleotide comprising a sequence that is at least 80% identical to a sequence selected from the group consisting of: SEQ ID Nos:1, 3, 5, 7, 9, 11, 13, and 15; a polynucleotide comprising a sequence that is at least 80% identical to a sequence selected from the group consisting of: from about nucleotide 1 to about nucleotide 123 of SEQ ID NO:1, 3, or 13; from about nucleotide 196 to about nucleotide 408 of SEQ ID NO:1 or 13; from about nucleotide 478 to about nucleotide 489 of SEQ ID NO:1; from about nucleotide $x_3$ to about nucleotide $x_4$ of SEQ ID NO:3, wherein $x_3$ is a nucleotide between about 196 to about nucleotide 427 and $x_4$ is a nucleotide between about 678 to about nucleotide 699; from about 427 to about nucleotide 678 of SEQ ID NO:3; from about nucleotide 37 to about nucleotide 159 of SEQ ID NO:5; from about nucleotide $x_3$ to about nucleotide $x_4$ of SEQ ID NO:5, wherein $x_3$ is a nucleotide between about 232 to about nucleotide 463 and $x_4$ is a nucleotide between about 717 to about nucleotide 732; from about nucleotide 463 to about nucleotide 717 of SEQ ID NO:5; from about nucleotide 49 to about nucleotide 171 of SEQ ID NO:7 or 11; from about nucleotide 244 to about nucleotide 456 of SEQ ID NO:7; from about nucleotide 526 to about nucleotide 576 of SEQ ID NO:7; from about nucleotide 101 to about nucleotide 223 of SEQ ID NO:9; from about nucleotide $x_3$ to about nucleotide 841 of SEQ ID NO:9, wherein $x_3$ is a nucleotide between about 296 to about nucleotide 524; from about nucleotide 524 to about nucleotide 841 of SEQ ID NO:9; from about nucleotide $x_3$ to about nucleotide 876 of SEQ ID NO:1, wherein $x_3$ is a nucleotide between about 244 to about nucleotide 475; from about nucleotide 475 to about nucleotide 876 of SEQ ID NO:11; from about nucleotide 478 to about nucleotide 534 of SEQ ID NO:13; from about nucleotide 164 to about nucleotide 286 of SEQ ID NO:15; from about nucleotide 359 to about nucleotide 571 of SEQ ID NO:15; and from about nucleotide 641 to about nucleotide 690 of SEQ ID NO:15; a polynucleotide that hybridizes under moderately stringent conditions to a polynucleotide comprising the sequence above; a nucleotide sequence complementary to the nucleic acid sequence of above; and any of nucleotide sequences of above wherein T can also be U.

The invention further provides an expression vector comprising a polynucleotide of the invention as well as recombinant host cells genetically engineered to contain a polynucleotide or expression vector of the invention.

The invention provides a method for producing a polypeptide of the invention, comprising culturing the host cell containing a polynucleotide of the invention under conditions promoting expression of the polypeptide and purifying the polypeptide.

Antibodies that bind to a polypeptide of the invention are also provided. In one embodiment, the antibody specification binds to a polypeptide having a sequence as set forth in SEQ ID NO:2, 4, 6, 8, 10, 12, 14, and/or 16. The antibody can be monoclonal, polyclonal, human, humanized, and the like. In one embodiment the antibody inhibits the activity of a polypeptide of the invention.

The invention further provides a method for identifying an agent that modulates an activity of a polypeptide of the invention. The method includes contacting an agent and a polypeptide of the invention under conditions such that the agent and polypeptide interact; and determining the activity of the polypeptide in the presence of the agent compared to a control, wherein a change in activity is indicative of an agent that modulates the polypeptide's activity. The agent can be an antibody, a small molecule, a peptide, and/or a peptidomimetic.

Also provided by the invention is a method of inhibiting the formation of atherosclerotic plaques in a mammal in need of such treatment, comprising administering to the mammal an inhibition-effective amount of a solCtLL polypeptide of the invention.

A method for inhibiting infection in a subject is also provided by the invention. The method includes contacting the subject with a solCtLL polypeptide of the invention.

The invention also provides a method for modulating endothelial cell migration, comprising contacting an endothelial cell with a polypeptide of the invention. The contacting can be in vitro, ex vivo, or in vivo.

The invention further provides a method of modulating immune cell activity comprising contacting a cell or mammal that expresses a polypeptide of the invention with an effective amount of solCtLL polypeptide. In one embodiment, the mammal is afflicted with a condition selected from the group consisting of ocular disorders; malignant and metastatic conditions; inflammatory diseases; osteoporosis, accelerated bone resorption disorders; restenosis; inappropriate platelet activation, recruitment, or aggregation; thrombosis; atherosclerosis; and a condition requiring tissue repair or wound healing. In another embodiment, the solCtLL polypeptide is in the form of a multimer.

Also provided by the invention is a method of stimulating an immune response in a subject. The method includes administering an agent to the subject wherein the agent blocks the interaction of a CtLL polypeptide with its ligand. In one embodiment, the agent is an antibody.

The invention also provides a method of inhibiting an immune response in a subject in need of such treatment comprising administering an agent to the subject wherein the agent simulates CtLL activity.

BRIEF DESCRIPTION OF THE FIGURES

FIG. 1 shows an alignment of the CtLL polypeptides of the invention, SEQ ID NO: 8, 2, 16, 14, 10, 6, and 4 (top to bottom) and indicates the polypeptides' putative domains.

FIG. 2 A-C shows a Pile-Up of molecules having homology to a CtLL polypeptide SEQ ID NO:12 of the invention.

DETAILED DESCRIPTION OF THE INVENTION

C-type lectins are a family of glycoproteins that exhibit amino acid sequence similarities in their carbohydrate recognition domains (CRD) and that bind to selected carbohydrates in a $Ca^{2+}$-dependent manner. C-type lectins have been subdivided into four categories (Vasta et al., Ann NY Acad Sci., 712:55-73, 1994; Spiess, Biochemistry, 29:10009-10018, 1990). The first group comprises type II membrane-integrated proteins, such as asialoglycoprotein receptors, macrophage galactose and N-acetyl glucosamine (GlcNac)-specific lectin, and CD23 (FcγRII). Many members in this group exhibit specificity for galactose/fucose, galactosamine/GalNac or GlcNac residues. The second group includes cartilage and fibroblast proteoglycan core proteins. The third group includes the so-called "collectins" such as serum mannose-binding proteins, pulmonary surfactant protein SP-A, and conglutinin. The fourth group includes certain adhesion molecules, which are known as LEC-CAMs (e.g., MeI-14, GMP-140, and ELAM-1).

C-type lectins are known to function as agglutinins, opsonins, complement activators, and cell-associated recognition molecules (Vasta et al., Ann NY Acad Sci., 712:55-73, 1994; Spiess, Biochemistry, 29:10009-10018, 1990; Kery, Int J Biochem., 23(7-8):631-40, 1991). For instance, macrophage mannose receptors serve a scavenger function (Shepherd et al., Am J Respir Cell Mol Biol., 2(4):335-40, 1990), as well as mediating the uptake of pathogenic organisms, including *Pneumocystis carinii* (Ezekowitz et al., Nature, 351(6322): 155-8, 1991) and *Candida albicans* (Ezekowitz et al., J Exp Med., 172(6):1785-94, 1990). Serum mannose-binding protein mimics Clq in its capacity to activate complement through the classical pathway. Importantly, genetic mutations in this lectin predispose for severe recurrent infections, diarrhea, and failure to thrive (Reid et al., Springer Semin Immunopathol., 15(4):307-26, 1994). Thus, C-type lectins exhibit diverse functions with biological significance.

Many diseases have been identified that relate to abnormalities of macrophage function, especially adherence, chemotaxis, and microbicidal activity. Some of these abnormalities may be due to defects in the recognition of foreign particles, diseased tissues or host tissues via lectin receptor molecules expressed by, for example, macrophages. For example, macrophage cell-surface lectins may be linked to the chronic rejection of cardiac allografts in arteriosclerosis, by serving as a possible mediator of macrophage infiltration (Russel et al., J Clin Invest 94: 722-730, 1994). Pathogenic mycobacteria, including *M. tuberculosis*, colonize activated macrophages. The attachment of such pathogens to macrophages is the preliminary step in pathogenesis. The colonization has been shown to occur via mannose-specific lectin receptors expressed on the macrophages (Goswami et al., FEBS Lett 355:183-186, 1994).

Based upon its homology to the C-type lectin protein family, the CtLL polynucleotides and polypeptides disclosed herein may be useful in the treatment or prevention of disorders such as graft rejection, autoimmune disease, bacterial and parasitic infections, cell proliferative disorders (e.g., cancer), and cardiac and vascular diseases and disorders (e.g., myocardial infarctions and stroke associated with atherosclerosis) to name a few. Other diseases and disorders are provided herein and are known to those of skill in the art.

The CtLL polypeptides of the invention lack residues important for binding to carbohydrate ligands. The CtLL polypeptides have greater sequence homology to a related member of the C-type lectin family, OLR1 and OLR1-related C-type lectin molecules (OLR1 was previously called LOX-1). OLR1 is an endothelial receptor for oxidized low-density lipoprotein that plays essential roles in atherogenesis and has a gene structure that resembles that of the natural killer cell receptors. The CtLL polynucleotide sequence lies closes in the genome to CLEC2 (a family member expressed in liver) and between CLEC2 and CLEC1 (a family member expressed in dendritic cells and endothelial cells) in a sub-cluster of molecules expressed in macrophages, DCs and endothelial cells including ORL1 which is expressed in macrophages and induced in endothelial cells and vascular smooth muscle cells (see also U.S. Pat. No. 6,277,959, the disclosure of which is incorporated herein by reference). The CtLL polynucleotide lies approximately 12 kB from CLEC2 and about 150 kB from CLEC1 (although there is evidence there is an intervening gene in this area). The CtLL polypeptides of the present invention have not been detected on DC, however, they have been detected on monocytes.

Based upon CtLL homology to the C-type lectins and OLR1, the CtLL polypeptides of the invention are predicted to have activities associated with oxidized low-density lipoprotein (oxLDL) binding and/or carbohydrate binding. Oxidized lipids, in particular oxLDL, have been shown to play a crucial role in atherosclerotic plaque formation and are a major immunogenic target believed to be a factor in "hot" or destabilized plaques that are a risk factor for thrombolytic events including lethal myocardial infarction and stroke. The progression of this vascular disease could therefore be modulated by antibodies or small molecules that bind CtLL polypeptides or that bind to a CtLL binding partner and trigger or inhibit its activity. In addition, soluble forms of a CtLL polypeptide of the invention would modulate disease progression by blocking a cellular inhibitory activity of CtLL (as discussed more fully below).

Since many C-type lectins, including OLR1, CLEC1, and CLEC2, are expressed on macrophages or dendritic cells, the CtLL polypeptides of the invention likely play a role in binding to the membrane of apoptotic cells or cell fragments. There is increasing evidence that antigen presenting cells recognize the exposed phosphatidylserine and phosphatidylcholine lipids on such apoptotic cells and cell fragments and take up the fragments for processing and antigen presentation. Current evidence suggests this is a particularly potent way to boost immune responses to cells dying through this process. Accordingly, a CtLL polypeptide or fragment thereof of the invention would therefore be expected to modulate the response of antigen presenting cells (APCs) to such fragments. A strong immune response would be especially beneficial in the treatment of tumors and cells carrying a pathogen (e.g., virally-infected cells). Blocking an inhibitory activity of a CtLL polypeptide using antibodies or soluble fragments of CtLL polypeptides would be one method of promoting such a response. In contrast, strong responses to normal cellular components including the oxLDLs themselves would be expected to play a pathological role in organ specific autoimmune diseases involving cell apoptosis such as diabetes and vascular diseases. Such anti-lipid responses are associated with thrombolytic complications in the PLS (anti-phospholipid syndrome) including that associated with SLE. In some instances promoting a negative signal by activating the ITIM domain of a CtLL polypeptide may prove beneficial. Antibodies can be developed which stimulate the activity of a CtLL polypeptide (i.e., stimulate the inhibitory activity of a CtLL polypeptide), such antibodies would be useful in promoting a negative response.

The novel CtLL polypeptides of the present invention have not been detected in dendritic cells but are detected on monocytes (see Example 8 below). In a separate analysis, CtLL polypeptides have been found to be down-regulated 3-4 fold in a murine asthma model during the onset and increased severity of the disease (as shown in Example 7 below). This may indicate that during inflammation, macrophage processing of apoptotic cells is downregulated, possibly to protect against excessive autoantigen presentation. This is consistant with lower CtLL expression levels when macrophages are activated in vitro.

In accordance with the invention, any polynucleotide sequence, which encodes a CtLL polypeptide sequence, can be used to generate recombinant molecules that can be used to express a CtLL.

A polypeptide includes any chain of amino acids, regardless of length or post-translational modification (e.g., glycosylation or phosphorylation), and include natural proteins, synthetic or recombinant polypeptides and peptides as well as a recombinant molecule consisting of a hybrid with one portion, for example, comprising all or part of a CtLL amino acid sequence, or CtLL amino acid sequence and a second portion being encoded by all or part of a different nucleotide sequence. A polypeptide may comprise L or D amino acids or a combination thereof. D-amino acids have been shown to increase the stability of polypeptide in biological systems by reducing the degradation by proteases. Typically a protein or polypeptide is substantially pure of other components from which it is normally present in nature. The term "substantially pure" or "purified" when referring to a polypeptide, means a polypeptide that is at least 30% free from the proteins and naturally-occurring organic molecules with which it is naturally associated. Preferably the substantially pure polypeptide of the invention is at least 35-50%; preferably 60-70%; more preferably at least 75%-90%; and most preferably at least 99% by weight purified from other naturally occurring molecules. A substantially pure polypeptide of the invention can be obtained, for example, by extraction from a natural source, by expression of a recombinant polynucleotide encoding the polypeptide, or by chemically synthesizing the polypeptide. Purity can be measured by any appropriate method, e.g., chromatography, PAGE, or HPLC analysis.

As used herein a "CtLL polypeptide" means (1) a polypeptide that contains or comprises an amino acid sequence as set forth in SEQ ID NO:2, 4, 6, 8, 10, 12, 14, or 16; (2) polypeptides having substantial homology or substantial identity to the sequences set forth in SEQ ID NO:2, 4, 6, 8, 10, 12, 14, or 16; (3) fragments of the foregoing sequences, including soluble fragments as discussed more fully below; and (4) conservative variants of the foregoing. Examples of preferred fragments of the invention include soluble fragments.

The CtLL polypeptides provided herein have a high degree of homology to members of the C-type lectin family and thus have a predicted function or activity of a C-type lectin polypeptide. Accordingly, the invention provides a CtLL polypeptide comprising a sequence as set forth in SEQ ID NO:2, 4, 6, 8, 10, 12, 14, or 16. A CtLL polypeptide can have an activity characteristic of C-type lectin family members, including activities characteristic of OLR1, CLEC1, and/or CLEC2. In one embodiment, a CtLL polypeptide has carbohydrate-binding or oxidized low-density lipoprotein (ox-LDL) binding activity. In yet another embodiment, a CtLL polypeptide or fragment thereof has agglutination activity (e.g., activating or inhibiting agglutination) or immune modulatory activity. Methods of determining whether a polypeptide of the invention has a desired activity can be accomplished by assaying the polypeptide by any of the methods described herein below.

A polypeptide of the invention also encompasses an amino acid sequence that has a substantial degree of identity or similarity to a sequence set forth in SEQ ID NO:2, 4, 6, 8, 10, 12, 14, or 16. Substantially identical sequences can be identified by those of skill in the art as having structural domains and/or having biological activity in common with a CtLL polypeptide. Methods of determining similarity or identity may employ computer algorithms such as, e.g., BLAST, FASTA, and the like.

The phrase "substantially identical," in the context of two nucleic acid molecules or polypeptides, refers to sequences or subsequences that have at least 50%, 60%, preferably 80% or 85%, more preferably 90-95%, and most preferably 96%, 97%, 98%, or 99% nucleotide or amino acid residue identity when aligned for maximum correspondence over a comparison window as measured by, for example, a sequence comparison algorithm or by manual alignment and visual inspection. This definition also refers to the complement of a test sequence, which has substantial sequence or subsequence complementarity when the test sequence has substantial identity to a reference sequence. A "comparison window," as used herein, includes reference to a segment of any one of the number of contiguous positions selected from the group consisting of from 20 to 1800, usually about 50 to 200, more usually about 70 to 150 in which a sequence may be compared to a reference sequence of the same number of contiguous positions after the two sequences are optimally aligned.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is PILEUP. PILEUP creates a multiple sequence alignment from a group of related sequences using progressive, pairwise alignments to show relationship and percent sequence identity. PILEUP uses a simplification of the progressive alignment method of Feng & Doolittle, J. Mol. Evol. 35:351 (1987), and is similar to the method described by Higgins & Sharp, CABIOS 5:151 (1989). The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, as described in Altschul et al., J. Mol. Biol. 215:403 (1990). Software for performing BLAST analyses is publicly available through the National Center for Biotechnology Information (www-ncbi.nlm.nih.gov/). This algorithm involves first identifying high scoring sequence pairs (HSPs) by identifying short words of length W in the query sequence, which either match or satisfy a positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST program uses as defaults a wordlength (W) of 11, the BLOSUM62 scoring matrix (see, Henikoff & Henikoff, Proc. Natl. Acad. Sci. USA 89:10915, 1989) alignments (B) of 50, expectation (E) of 10, M=5, N=4, and a comparison of both strands. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Alternatively, the percent identity of two amino acid or two nucleic acid sequences can be determined by comparing sequence information using the GAP computer program, version 6.0 described by Devereux et al. (Nucl. Acids Res. 12:387, 1984) and available from the University of Wisconsin Genetics Computer Group. The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Polypeptide Sequence and Structure, National Biomedical Research Foundation, pp. 353-358, 1979; (2) a penalty of 3.0 for each gap and an additional 0.10 penalty for each symbol in each gap; and (3) no penalty for end gaps.

One of skill will recognize that individual substitutions, deletions or additions to a nucleic acid sequence, peptide, or polypeptide sequence that alters, adds or deletes a single amino acid or a small percentage of amino acids in the encoded sequence is a "conservatively modified variant" where the alteration results in a molecule having substantially the same biological activity (e.g., oxLDL binding, carbohydrate binding activity, immune modulatory activity, and/or agglutination activity). For example, an alteration that results in the substitution of an amino acid with a chemically similar amino acid is a conservatively modified variant. Conservative substitution tables providing functionally similar amino acids are known in the art. The following six groups each contain amino acids that are conservative substitutions for one another 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, Proteins (1984)).

One indication that two polynucleotides or polypeptides are substantially identical is that the polypeptide encoded by a first polynucleotide is immunologically cross reactive with the antibodies raised against the polypeptide encoded by a second polynucleotide. Another indication that two polynucleotides are substantially identical is that the two molecules or their complements hybridize to each other under stringent conditions.

Polypeptides derived from the CtLL polypeptides of the invention by any type of alteration (e.g., insertions, deletions, or substitutions of amino acids; changes in the state of glycosylation of the polypeptide; refolding or isomerization to change its three-dimensional structure or self-association state; and changes to its association with other polypeptides or molecules) are also encompassed by the invention. Therefore, the polypeptides provided by the invention include polypeptides characterized by amino acid sequences similar to those as set forth in SEQ ID NO:2, 4, 6, 8, 10, 12, 14, or 16, but into which modifications are naturally provided or deliberately engineered. A polypeptide that shares biological activities in common with a polypeptide comprising a sequence as set forth in SEQ ID NO:2, 4, 6, 8, 10, 12, 14, or 16, having C-type lectin activity (e.g., oxLDL binding, carbohydrate binding activity, immune modulatory activity, and/or agglutination activity) are encompassed by the invention.

Of particular interest are soluble domains of the CtLL polypeptides of the invention. The polypeptides of the invention have a number of distinct domains. Table 1 below shows a number of domains associated with each of the CtLL polypeptides of the invention comprising SEQ ID NO:2, 4, 6, 8, 10, 12, 14 and 16.

TABLE 1

| SEQ ID NO: | Transmembrane Domain(s) (From about residue # to about #) | Soluble Domain(s) (From about residue # to about #) | C-Lectin Like Domain(s) (From about residue # to about #) |
|---|---|---|---|
| 2 | 42 to 65<br>137 to 159<br>164 to 182 | 1 to 41<br>66 to 136<br>160 to 163 | |
| 4 | 42 to 65 | 1 to 41<br>66 to 233 | 143 to 226 |
| 6 | 42 to 65 | 1 to 41<br>66 to 232 | 143 to 227 |
| 8 | 42 to 65<br>137 to 159 | 1 to 41<br>66 to 136<br>160 to 176 | |
| 10 | 42 to 65 | 1 to 41<br>66 to 247 | 142 to 247 |
| 12 | 42 to 65 | 1 to 41<br>66 to 276 | 142 to 276 |
| 14 | 42 to 65<br>137 to 159 | 1 to 41<br>66 to 136<br>160 to 178 | |
| 16 | 42 to 65<br>137 to 159 | 1 to 41<br>66 to 136<br>160 to 176 | |

The domains identified above were predicted using computer algorithms and/or comparison to known C-type lectin polypeptides. Accordingly, the N- and C-terminal domains may vary by a few amino acids depending upon such factors as the type of cell the molecule is expressed in and/or the types of proteases present in the expression or purification system. The identity of the terminal amino acid can be determined following expression by routine peptide sequencing procedures.

The CtLL polypeptides of the invention also have and at least one immunoreceptor tyrosine-based inhibitory motif (ITIM). Many receptors that mediate positive signaling have cytoplasmic tails containing sites of tyrosine phosphatase phosphorylation known as immunoreceptor tyrosine-based activation motifs (ITAM). A common mechanistic pathway for positive signaling involves the activation of tyrosine kinases that phosphorylate sites on the cytoplasmic domains of the receptors and on other signaling molecules. Once the receptors are phosphorylated, binding sites for signal transduction molecules are created which initiate the signaling pathways and activate the cell. The inhibitory pathways involve receptors having immunoreceptor tyrosine based inhibitory motifs (ITIM) which, like the ITAMs, are phosphorylated by tyrosine kinases. Receptors having ITIM motifs are involved in inhibitory signaling, which block signaling by removing tyrosine from activated receptors or signal transduction molecules (Renard et al., *Immun Rev* 155: 205-221, 1997). ITIMs have the consensus sequence I/VxYxxLN (SEQ ID NO:17), and are found in the cytoplasmic portions of diverse signal transduction proteins of the immune system, many of which belong to the Ig superfamily or to the family of type II dimeric C-lectins. Proteins that contain ITIMs include the "killer cell Ig-like receptors," or "KIRs," and some members of the leukocyte Ig-like receptor or "LIR" family of proteins (Cosman et al., *Immunity* 7:273-82, 1997; Borges et al., *J Immunol* 159:5192-96, 1997). Signal transduction by an ITIM is believed to downregulate targeted cellular activities, such as expression of cell surface proteins. It is thought that the regulation of complex cellular functions is fine-tuned by the interplay of ITIM-mediated inhibitory signal transduction and activation of the same functions by the 16-18 amino acid ITAM activator motif. CD22 and FcγRIIb1 also have ITIMs in their cytoplasmic domain and function to send inhibitory signals that down regulate or inhibit cell function. It has been shown that these receptors associate with SHP-1 phosphatase via binding to the ITIM motifs. Recruitment of the SHP-1 phosphatase by the receptor appears to be required for intracellular signaling pathways that regulate the inhibitory function of the receptors. Significantly, C-type lectins that are type II membrane proteins having a single intracellular ITIM motif have also been reported. For example, genes localized on human chromosome 12p12-p13 in a region designated as the NK gene complex includes products of the NKG2 complex and CD94, which are involved in recognition of MHC class I molecules and in regulation of NK cell activity. Inhibition of cellular functions by NKG2A/B-CD94 heterodimers is linked to the presence of ITIMs in the NKG2A/B intracellular domain (Lazetic, S. C., et al., *J. Immunol.* 157:4741, 1996; Houchins, J. P., et al., *J. Immunol.* 158:3603, 1997).

Thus, by analogy with other C-type lectin family members having ITIM motifs, the polypeptides presented in SEQ ID NO:2, 4, 6, 8, 10, 12, 14, or 16 having ITIM motifs, deliver an inhibitory signal via the interaction of its ITIM with one or more phosphatases, such as tyrosine phosphatases (including SHP-1 tyrosine phosphatase), when the CtLL polypeptides are bound with an appropriate receptor or natural ligand. Also by analogy with immunoregulatory receptors possessing ITIMs, CtLL family members have a regulatory influence on humoral and cell-mediated immunity, recognition of MHC class I molecules and in regulation of immune cell activity, as well as modulating inflammatory and allergic responses. Clearly, the immune system activatory and inhibitory signals mediated by opposing kinases and phosphatases are very important for maintaining balance in the immune system. Systems with a predominance of activatory signals will lead to autoimmunity and inflammation. Immune systems with a predominance of inhibitory signals are less able to challenge infected cells or cancer cells. Thus, CtLL family members play a role in maintaining balance in the immune system.

The progression of this vascular disease can be modulated by antibodies or small molecules that bind CtLL polypeptides and trigger or inhibit its activity. In addition, soluble forms of a CtLL polypeptide of the invention can modulate disease progression by blocking the cellular inhibitory activity of CtLL.

Since many C-type lectins, including OLR1, CLEC1, and CLEC2, are expressed on macrophages and dendritic cells, the CtLL polypeptides of the invention likely play a role in binding to the membrane of apoptotic cells or cell fragments. Although the CtLL polypeptides of the present invention have not been detected on dendritic cells, they have been detected on monocytes. There is increasing evidence that antigen presenting cells including macrophages recognize the exposed phosphatidylserine and phosphatidylcholine lipids on such cells and take up the fragments for processing and antigen presentation. Current evidence suggests this is a particularly potent way to boost immune responses to cells dying through this process. Accordingly, the CtLL polypeptides would therefore be expected to modulate the response of antigen presenting cells (APCs) to such fragments. Such a strong immune response would be beneficial for treating tumors and pathogen-infected cells (e.g., virally-infected cells). Blocking the inhibitory activity of the CtLL polypeptides using antibodies or soluble fragments of CtLL polypeptides would be one method of promoting such a response. In contrast, strong responses to normal cellular components including the oxLDLs themselves would be expected to play a pathological role in organ specific autoimmune diseases involving cell apoptosis such as diabetes and vascular diseases. Such anti-lipid responses are associated with thrombolytic complications in PLS (anti-phospholipid syndrome) including that associated with SLE. In such instances promoting a negative signal by activating the ITIM domain of a CtLL polypeptide may prove beneficial.

Strong responses to normal cellular components including the oxLDLs themselves would be expected to play a pathological role in organ specific autoimmune diseases involving cell apoptosis such as diabetes and vascular diseases. Such anti-lipid responses are associated with thrombolytic complications in PLS (anti-phospholipid syndrome) including that associated with SLE. In such instances promoting a negative signal by activating the ITIM domain of a CtLL polypeptide may prove beneficial.

The protein ligands for the ITIM-containing members of the genomic cluster include MHC molecules for example, HLA-E binding to the heterodimer CD94-NKG2A/B. These molecules down-regulate innate immune responses in NK cells and block NK killing of self via their ligand recognition. Loss of expression of their ligand allows NK cells to lyse tumor cells or pathogen infected cells. One feature of these molecules is that they transit to the cell surface and exert their activities as hetero- or homodimers. Thus, a CtLL polypeptide can bind a protein ligand and block or lower immune responses via HLA-like or MHC-like molecules potentially as a complex with another molecule in a multimeric form. Most likely this response will be mediated through leukocytes other than, or in addition to, NK cells. Thus, a CtLL polypeptide (including soluble fragments thereof) are important in clinical settings including infection and cancer by altering immune system and the recognition of cells as self and non-self. Blocking CtLL function using, for example, a soluble CtLL polypeptide or antibody would boost tumor responses and responses to pathogen infected cells.

The present invention encompasses the use of various forms of CtLL polypeptides or domains that have at least one activity selected from the group consisting of carbohydrate binding activity, lipoprotein binding activity (e.g., oxLDL binding activity), agglutination inhibition activity, cell-cell adhesion activity, capable of binding or interacting with a proteinaceous ligands, binding or interacting with apoptotic cells, and modulate the activation of tyrosine phosphatases. A CtLL soluble domain is intended to encompass polypeptides comprising all or part of a CtLL polypeptide of the invention but lacking a transmembrane domain. Of particular interest are CtLL soluble domains characterized as having (1) identity to and/or biological activity of a lectin domain, (2) having carbohydrate-binding activity, and/or (3) having lipoprotein binding activity. In a one embodiment, a soluble domain contains all or part of a CtLL extracellular or cytoplasmic domain, with or without other domains (e.g., the transmembrane domain), as well as related forms including, but not limited to: (a) fragments, (b) variants, (c) derivatives, (d) fusion polypeptides, and (e) multimeric forms (multimers). The ability of these related forms to inhibit or modulate carbohydrate binding, lipoprotein binding (e.g., oxidized lipid binding), agglutination, immune system activation, or inflammatory cell activation may be determined in vitro or in vivo by using methods such as those exemplified below or by using other assays known in the art.

A soluble domain (e.g., a fragment of a CtLL polypeptide comprising an extracellular domain) of the invention can provide a dominant-negative activity. A soluble domain of the invention ("solCtLL") includes polypeptides comprising a sequence shown in columns 3 and/or 4 of Table 1 and fragments thereof that bind or interact with proteinaceous ligands, bind or interact with oxidized lipids, bind or interact with apoptotic cells, or inhibit the activation of tyrosine phosphatases (typically activated by binding of the native CtLL molecule to its ligand), or inhibits a biological activity exhibited by members of the C-type lectin family of polypeptides. As mentioned above, the CtLL polypeptides of the invention contain an intracellular ITIM motif and so binding of a CTLL polypeptide comprising an ITIM motif to its ligand(s) is predicted to down-regulate, through the activation of tyrosine phosphatases, activating signals received by the cell in the context of the CtLL ligand(s). Accordingly, soluble forms of the ligand-binding domain of a CtLL polypeptide would therefore be predicted to increase cellular activation. Preferably the solCtLL comprises an amino acid sequence as set forth in SEQ ID NO:4, 6, 10, or 12 (e.g., a polypeptide comprising a sequence from about 143 to 226 of SEQ ID NO:4; from about 143 to 227 of SEQ ID NO:6; from about 142 to 247 of SEQ ID NO:10; and/or from about 142 to 276 of SEQ ID NO:12).

One of skill in the art can assay for activity using the methods described herein. Such methods measure, for example, carbohydrate binding activity, agglutination inhibition activity, cell-cell adhesion activity, binding or interaction with proteinaceous ligands, binding or interaction with oxidized lipids, binding or interaction with apoptotic cells, inhibition of the activation of tyrosine phosphatases, or inhibition of a biological activity exhibited by members of the C-type lectin family of polypeptides. For example, anti-CtLL antibodies, which neutralize CtLL activity (e.g., binding or interaction with proteinaceous ligands, binding or interaction with oxidized lipids, binding or interaction with apoptotic cells, activation of tyrosine phosphatases, cell-cell adhesion activity, and the like) can be used to assay for similar polypeptides by contacting an anti-CtLL antibody with a polypeptide of interest and determining if the activity associated with the polypeptide of interest is neutralized. Similarly, the activity of solCtLL polypeptide may be determined by contacting a cell, tissue, or subject that expresses a native CtLL polypeptide with the solCtLL polypeptide and measuring a change in, for example, binding or interaction with proteinaceous ligands, binding or interaction with oxidized lipids, binding or interaction with apoptotic cells, inhibition of the activation of tyrosine phosphatases, and/or cell-cell adhesion activity.

The invention provides both full-length and mature forms of CtLL polypeptides. Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule (e.g., SEQ ID NO:1, 3, 5, 7, 9, 11, 13, or 15).

Several full-length polypeptides may be encoded by a single genetic locus if multiple mRNA forms are produced from that locus by alternative splicing or by the use of multiple translation initiation sites. The "mature form" of a polypeptide refers to a polypeptide that has undergone post-translational processing steps, if any, such as, for example, cleavage of the signal sequence or proteolytic cleavage to remove a pro-domain. Multiple mature forms of a particular full-length polypeptide may be produced, for example, by imprecise cleavage of the signal sequence, or by differential regulation of proteases that cleave the polypeptide. The mature form(s) of such polypeptide may be obtained by expression, in a suitable mammalian cell or other host cell, of a polynucleotide that encodes the full-length polypeptide. The sequence of the mature form of the polypeptide may also be determinable from the amino acid sequence of the full-length form, through identification of signal sequences or protease cleavage sites.

The CtLL polypeptides of the invention also include polypeptides that result from post-transcriptional or post-translational processing events such as alternate mRNA processing which can yield a truncated but biologically active polypeptide, for example, a naturally occurring soluble form of the polypeptide. Also encompassed within the invention are variations attributable to proteolysis such as differences in the N- or C-termini upon expression in different types of host cells, due to proteolytic removal of one or more terminal amino acids from the polypeptide (generally from 1-5 terminal amino acids).

A polypeptide of the invention may be prepared by culturing transformed or recombinant host cells under culture conditions suitable to express a polypeptide of the invention. The resulting expressed polypeptide may then be purified from such culture using known purification processes, such as gel filtration and ion exchange chromatography. The purification of the polypeptide may also include an affinity column containing agents which will bind to the polypeptide; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, a polypeptide of the invention may also be expressed in a form that will facilitate purification. For example, it may be expressed as a fusion polypeptide, joined to, for example, maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.), and InVitrogen, respectively. The polypeptide can also be tagged with an epitope and subsequently purified by using a specific antibody directed to such epitope. One such epitope ("Flag") is commercially available from Kodak (New Haven, Conn.). Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous recombinant polypeptide. The polypeptide thus purified is substantially free of other mammalian polypeptides and is defined in accordance with the invention as a "substantially purified" polypeptide; such purified polypeptides include antibodies that specifically bind to a CtLL polypeptide, fragment, variant, and the like. A polypeptide of the invention may also be expressed as a product of transgenic animals, e.g., as a component of the milk of transgenic cows, goats, pigs, or sheep which are characterized by somatic or germ cells containing a polynucleotide encoding a polypeptide of the invention.

It is also possible to utilize an affinity column such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention. In this aspect of the invention, proteins that bind a polypeptide of the invention (e.g., an anti-CtLL antibody of the invention) can be bound to a solid phase support or a similar substrate suitable for identifying, separating, or purifying cells that express polypeptides of the invention on their surface. Adherence of, for example, an anti-CtLL antibody of the invention to a solid phase surface can be accomplished by any means known in the art. For example, magnetic microspheres can be coated with these polypeptide-binding proteins and held in the incubation vessel through a magnetic field. Suspensions of cell mixtures are contacted with the solid phase that has such polypeptide-binding proteins thereon. Anti-CtLL antibodies bind cells having polypeptides of the invention on their surface (e.g., an extracellular domain of CtLL). Unbound cells (e.g., cell lacking and CtLL polypeptide) are washed away from the bound cells. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. Alternatively, mixtures of cells suspected of containing polypeptide-expressing cells of the invention are first incubated with a biotinylated binding polypeptide of the invention. Incubation periods are typically at least one hour in duration to ensure sufficient binding to polypeptides of the invention. The resulting mixture then is passed through a column packed with avidin-coated beads, whereby the high affinity of biotin for avidin provides the binding of the cells to the beads. Use of avidin-coated beads is known in the art (see, Berenson, et al. *J. Cell. Biochem.*, 10D:239, 1986). Wash of unbound material and the release of the bound cells is performed using conventional methods. Carbohydrate molecules can also be used to purify cells comprising the polypeptides of the invention. Carbohydrate molecules that specifically interact with the lectin domain of the polypeptides of the invention can be used to purify the polypeptides. The polypeptides of the invention will bind to the carbohydrate via the lectin domain and the cell and/or polypeptide can subsequently be purified by using techniques known in the art.

A polypeptide of the invention may also be produced by known conventional chemical synthesis. Methods for constructing the polypeptides of the invention by synthetic means are known to those skilled in the art. The synthetically-constructed polypeptide sequences, by virtue of sharing primary, secondary or tertiary structural and/or conformational characteristics with a native polypeptides may possess biological properties in common therewith, including biological activity. Thus, the synthesized polypeptides may be employed as biologically active or immunological substitutes for natural, purified polypeptides in screening of therapeutic compounds, and in immunological processes for the development of antibodies.

The desired degree of purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Most preferably, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Species homologues of CtLL polypeptides and polynucleotides encoding the polypeptides are also provided by the invention. As used herein, a "species homologue" is a polypeptide or a polynucleotide with a different species of origin from that of a given polypeptide or polynucleotide, but with significant sequence similarity to the given polypeptide or polynucleotide. Species homologues may be isolated and identified by making suitable probes or primers from polynucleotides encoding the polypeptides provided herein and screening a suitable nucleic acid source from the desired species. One such variant is the murine CtLL, described in the Examples below. Alternatively, homologues may be identified by screening a genome database containing sequences from one or more species utilizing a sequence (e.g., nucleic acid or amino acid sequence) of a CtLL molecule of the invention. Such genome databases are readily available for a number of species (e.g., on the world wide web (www) at tigr.org/tdb; genetics.wisc.edu; stanford.edu/~ball; hiv-web.lan1.gov; ncbi.nlm.nig.gov; ebi.ac.uk; and pasteur.fr/other/biology). The invention also encompasses allelic variants of CtLL polypeptides and nucleic acids encoding them that are naturally-occurring alternative forms of such polypeptides and polynucleotides in which differences in amino acid or nucleotide sequence are attributable to genetic polymorphism.

Intermediate Sequence Search (ISS) can be used to identify closely related as well as distant homologues by connecting two proteins through one or more intermediate sequences. ISS repetitively uses the results of the previous query as new search seeds. Saturated BLAST is a package that performs ISS. Starting with a protein sequence, Saturated BLAST runs a BLAST search and identifies representative sequences for the next generation of searches. The procedure is run until convergence or until some predefined criteria are met. Saturated BLAST is available on the world wide web (www) at: bioinformatics.burnham-inst.org/xblast (see also, Li et al. Bioinformatics 16(12): 1105, 2000).

Fragments of the CtLL polypeptides of the invention are encompassed by the invention and may be in linear form or cyclized using known methods (see, e.g., Saragovi, et al., Bio/Technology 10, 773 (1992); and McDowell, et al., J. Amer. Chem. Soc. 114:9245 (1992), both of which are incorporated by reference herein). Peptide fragments of CtLL polypeptides of the invention, and polynucleotides encoding such fragments include amino acid or nucleotide sequence lengths that are at least 25% (more preferably at least 50%, 60%, or 70%, and most preferably at least 80%) of the length of a CtLL polypeptide or polynucleotide. Preferably such sequences will have at least 60% sequence identity (more preferably at least 70%-75%, 80%-85%, 90%-95%, at least 97%-97.5%, or at least 99%, and most preferably at least 99.5%) with a CtLL polypeptide or polynucleotide when aligned so as to maximize overlap and identity while minimizing sequence gaps. Also included in the invention are polypeptides, peptide fragments, and polynucleotides encoding such fragments, that contain or encode a segment preferably comprising at least 8 to 10, or more preferably at least 20, or still more preferably at least 30, or most preferably at least 40 contiguous amino acids. Such polypeptides and fragments may also contain a segment that shares at least 70% (at least 75%, 80%-85%, 90%-95%, at least 97%-97.5%, or at least 99%, and most preferably at least 99.5%) with any such segment of, for example, any of the C-type lectin family polypeptides, when aligned so as to maximize overlap and identity while minimizing sequence gaps. Visual inspection, mathematical calculation, or computer algorithms can determine the percent identity.

The invention also provides soluble forms of CtLL polypeptides (solCtLL) comprising certain fragments or domains of the CtLL polypeptides of SEQ ID Nos:2, 4, 6, 8, 10, 12, 14, and 16. Soluble fragments capable of binding or interacting with proteinaceous ligands, binding or interacting with oxidized lipids, binding or interacting with apoptotic cells, inhibiting the activation of tyosine phosphatases (typically activated by binding of the native CtLL molecule to its ligand), or inhibition of a biological activity exhibited by members of the C-type lectin family of polypeptides, are of particular interest and include, for example, an amino acid sequence as set forth in Table 1, columns 3 and 4. For example, soluble CtLL polypeptides ("solCtLL") of the present invention comprise amino acids: from about residue 1 to about 41 of SEQ ID NO:2, 4, 6, 8, 10, 12, 14, or 16; from about residue 66 to about 136 of SEQ ID NO:2, 8, 14, and 16; from about residue $x_1$ to about $x_2$ of SEQ ID NO:4, wherein $x_1$ is a residue between and including residues 66 and 143 and $x_2$ is a residue between and including residue 226 and 233 (e.g., 226, 227, 228, 229, etc.); from about residue $x_1$ to about $x_2$ of SEQ ID NO:6, wherein $x_1$ is a residue between and including residues 66 and 143 and $x_2$ is a residue between and including residue 227 and 232 (e.g., 227, 228, 229, 230, etc.); from about residue $x_1$ to about 247 of SEQ ID NO:10, wherein $x_1$ is a residue between and including about residues 66 and 142; and/or from about residue $x_1$ to about 276 of SEQ ID NO:12, wherein $x_1$ is a residue between and including residues 66 and 142. Such a solCtLL can be secreted from the cell in which it is expressed. A used herein, the term "between about" or "at about" will be understood to include sequences between any such referenced residues of a sequence. For example, "a residue between and including about residue 66 and 143" means residue 66, 67, 68, 69, 70, . . . , 140, 141, 142, or 143".

Transmembrane regions can be identified using publicly available computer algorithms. The intracellular and transmembrane domains of polypeptides of the invention can be identified in accordance with known techniques for determination of such domains from sequence information. For example, alignment of the polypeptide sequences of the invention with other members of the C-type lectin family of polypeptides having known domains will provide information regarding the domains of the polypeptides of the invention. Accordingly, an alignment and computer algorithm analysis of SEQ ID Nos:2, 4, 6, 8, 10, 12, 14, and 16 indicates a transmembrane domain includes about amino acids 42 to 65 of SEQ ID Nos:2, 4, 6, 8, 10, 12, 14, and 16; includes about amino acids 137 to 159 of SEQ ID Nos:2, 8, 14, and 16; and includes about amino acids 164 to 182 of SEQ ID NO:2. One of skill in the art will recognize that slight modifications in the range of sequences of a particular domain can be made without affecting the molecule's biological activity. Accordingly, changes in the identified sequences and domains of the invention by 1, 2, 3, 4, or 5 to 10 amino acids in either direction of the particular domain are encompassed by the present invention.

In another aspect of the invention, a polypeptide may comprise various combinations of C-type lectin polypeptide domains, such one or more lectin domains linked to a lectin domain of the present invention (e.g., from about residue $x_1$ to about $x_2$ of SEQ ID NO:4, wherein $x_1$ is a residue between and including residues 66 and 143 and $x_2$ is a residue between and including residue 226 and 233). Accordingly, polypeptides of the invention and polynucleotides include those comprising or encoding two or more copies of a domain such as the lectin domain of the present invention, a lectin domain of the present invention and C-type lectin domain of another C-type lectin polypeptide, or one or more solCtLL polypeptides, these domains may be presented in any order within such polypeptides. For example, the invention provides a polypeptide comprising $Z_1$-X-$Z_2$, wherein $Z_1$ and $Z_2$ are each individually a solCtLL polypeptide (as described above), and X is a peptide linker. Accordingly, the invention includes recombinant polypeptides and the polynucleotides encoding the polypeptides wherein the recombinant polypeptides are "chimeric polypeptides" or "fusion polypeptides" and comprise a solCtLL sequence as set forth above operatively linked to a second polypeptide. The second polypeptide can be any polypeptide of interest having an activity or function independent of, or related to, the function of a CtLL polypeptide. For example, the second polypeptide can be a domain of a related but distinct member of the C-type lectin family of polypeptides such as, for example, an extracellular, cytoplasmic, or transmembrane domain of a C-type lectin polypeptide. The term "operatively linked" is intended to indicate that the CtLL sequence and the second polypeptide sequence are fused in-frame to each other. The second polypeptide can be fused to the N-terminus or C-terminus of a CtLL or solCtLL sequence as set forth in FIG. 1 or as set forth above. For example, in one embodiment the fusion polypeptide is a GST-CtLL or GST-solCtLL fusion polypeptide in which a CtLL or solCtLL polypeptide is fused to the C-terminus of a GST sequence. Such fusion polypeptides can facilitate the purification of recombinant CtLL and solCtLL polypeptides and fragments. In another embodiment, the fusion polypeptide comprises a CtLL or solCtLL sequence having a heterologous signal sequence at its N-terminus. In certain host cells (e.g., mammalian host cells), expression and/or secretion of a CtLL or solCtLL polypeptide can be increased through use of a heterologous signal sequence. As another example, a CtLL polypeptide, solCtLL, or fragments thereof may be fused to a hexa-histidine tag to facilitate purification of bacterially expressed protein, or to a hemagglutinin tag to facilitate purification of protein expressed in eukaryotic cells. Further, fusion polypeptides can comprise, for example, poly-His or the antigenic identification peptides described in U.S. Pat. No. 5,011,912 and in Hopp et al., *Bio/Technology* 6:1204, 1988. One such peptide is the FLAG® peptide, which is highly antigenic and provides an epitope reversibly bound by a specific monoclonal antibody, enabling rapid assay and facile purification of an expressed recombinant polypeptide. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the ATCC under accession no. HB9259. Monoclonal antibodies that bind the FLAG® peptide are available from Eastman Kodak Co., Scientific Imaging Systems Division, New Haven, Conn.

Encompassed by the invention are oligomers that comprise a CtLL polypeptide or solCtLL polypeptide. Oligomers that can be in the form of covalently linked or non-covalently-linked multimers, including dimers, trimers, or higher oligomers. In one aspect of the invention, the oligomers maintain the binding ability or biological activity of the polypeptide components and provide therefor, bivalent, trivalent, and the like, binding or catalytic sites. In another embodiment, the invention is directed to oligomers comprising multiple polypeptides joined via covalent or non-covalent interactions linked to or between peptide moieties fused to the polypeptides. Such peptides can be peptide linkers (spacers), or peptides that have the property of promoting oligomerization. Leucine zippers and certain polypeptides derived from antibodies are among the peptides that can promote oligomerization of the polypeptides attached thereto, as described in more detail below.

Peptide linkers can be used between two or more CtLL or solCtLL polypeptides. Typically a peptide linker moiety is chosen to optimize the biological activity of the polypeptide comprising a CtLL or solCtLL sequence and can be determined empirically without undue experimentation. The linker moiety should be long enough and flexible enough to allow a CtLL or solCtLL polypeptide to freely interact with a substrate or ligand. The preferred linker moiety is a peptide between about one and 30 amino acid residues in length, preferably between about two and 15 amino acid residues. Preferred linker moieties are --Gly-Gly--, GGGGS (SEQ ID NO:18), (GGGGS)$_n$ (SEQ ID NO:18), GKSSGSGSESKS (SEQ ID NO:19), GSTSGSGKSSEGKG (SEQ ID NO:20), GSTSGSGKSSEGSGSTKG (SEQ ID NO:21), GSTSGS-GKPGSGEGSTKG (SEQ ID NO:22), or EGKSSGSG-SESKEF (SEQ ID NO:23). Linking moieties are described, for example, in Huston, J. S., et al., PNAS 85:5879 (1988), Whitlow, M., et al., Protein Engineering 6:989 (1993), and Newton, D. L., et al., Biochemistry 35:545 (1996). Other suitable peptide linkers are those described in U.S. Pat. Nos. 4,751,180 and 4,935,233, which are hereby incorporated by reference. A DNA sequence encoding a desired peptide linker can be inserted between, and in the same reading frame as, a DNA sequences encoding a CtLL polypeptide or fragment thereof (e.g., a solCtLL), using any suitable conventional technique. For example, a chemically synthesized oligonucleotide encoding the linker can be ligated between the sequences. In particular embodiments, a fusion polypeptide comprises from two to four solCtLL polypeptides, separated by peptide linkers.

In embodiments where variants of a CtLL polypeptide are constructed to include a membrane-spanning domain, they will form a Type II membrane polypeptide. In such embodiments, it is preferable to link the fusion partner to the C-terminus of the CtLL or solCtLL polypeptide. Alternatively, the membrane-spanning polypeptides can be fused with known extracellular receptor domain polypeptides, for which the ligand is also known. Such fusion polypeptides can then be manipulated to control an intracellular signaling pathways triggered by the bound CtLL polypeptide. Polypeptides that span the cell membrane can also be fused with agonists or antagonists of cell-surface receptors, or cellular adhesion molecules to further modulate CtLL intracellular effects. In another aspect of the invention, interleukins can be situated between the CtLL polypeptide fragment and other fusion polypeptide domains.

The CtLL polypeptides and solCtLL polypeptides of the invention can also include a localization sequence to direct the polypeptide to particular cellular sites by fusion to appropriate organellar targeting signals or localized host proteins. A polynucleotide encoding a localization sequence (signal sequence), can be ligated or fused at the 5' terminus of a polynucleotide encoding a CtLL or solCtLL polypeptide such that the localization peptide comprising the localization sequence is located at the amino terminal (5') end of the resulting fusion polypeptide (polynucleotide). In eukaryotes, the localization peptide functions to transport a polypeptide across the endoplasmic reticulum. The secretory polypeptide is then transported through the Golgi apparatus, into secretory vesicles and into the extracellular space or the external environment. Localization (signal) peptides include pre-pro peptides that contain a proteolytic enzyme recognition site.

The localization peptide can be a nuclear-, an endoplasmic reticulum-, a peroxisome-, or a mitochondrial-localization sequence, or a localized protein. Localization peptide can comprise targeting sequences that are described, for example, in "Protein Targeting", chapter 35 of Stryer, L., Biochemistry (4th ed.). W. H. Freeman, 1995. Some important localization sequences include those targeting the nucleus (e.g., KKKRK (SEQ ID NO:24)), mitochondria (MLRTSSLFTR-RVQPSLFRNI LRLQST (SEQ ID NO:25)), endoplasmic reticulum (KDEL (SEQ ID NO:26)), peroxisome (SKF), plasma membrane (CAAX (SEQ ID NO:27), CC, CXC, or CCXX (SEQ ID NO:28)), cytoplasmic side of plasma membrane (fusion to SNAP-25), or the Golgi apparatus (fusion to furin).

In another embodiment, a polypeptide of the invention or fragments thereof may be fused to carrier molecules such as immunoglobulins for a variety of purposes including increasing the valency of polypeptide binding sites. As an example, a fragment (e.g., solCtLL) of a polypeptide of the invention may be fused through a peptide linker to the Fc portion of an immunoglobulin. For a bivalent form of the polypeptide, such a fusion could be to the Fc portion of an IgG molecule. Other immunoglobulin isotypes may also be used to generate such fusions. For example, a polypeptide-IgM fusion would generate a decavalent form of the polypeptide of the invention. In one embodiment, the invention provides a fusion polypeptide having an Fc polypeptide domain and a CtLL or solCtLL polypeptide sequence.

The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody. As one alternative, an oligomer is prepared using polypeptides derived from immunoglobulins. Preparation of fusion polypeptides comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Polypeptides", in *Current Protocols in Immunology*, Suppl. 4, pages 10.19.1-10.19.11, 1992). Methods for preparation and use of immunoglobulin-based oligomers are known in the art. One embodiment of the invention is directed to a dimer comprising two fusion polypeptides created by fusing a polypeptide of the invention to an Fc polypeptide derived from an antibody. A gene fusion encoding the polypeptide/Fc fusion polypeptide is inserted into an appropriate expression vector. Polypeptide/Fc fusion polypeptides are expressed in host cells transformed or transfected with the recombinant expression vector or recombinant polynucleotide encoding the fusion polypeptide, and allowed to assemble much like antibody molecules, whereupon interchain disulfide bonds form between the Fc moieties to yield divalent molecules. One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (EMBO J. 13:3992, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. The above-described fusion polypeptides comprising Fc moieties (and oligomers formed therefrom) offer the advantage of facile purification by affinity chromatography over Polypeptide A or Polypeptide G columns. In other embodiments, the polypeptides of the invention can be substituted for the variable portion of an antibody heavy or light chain. If fusion polypeptides are made with both heavy and light chains of an antibody, it is possible to form an oligomer with as many as four CtLL or solCtLL polypeptides or fragments thereof.

Another method for preparing the oligomers of the invention involves use of a leucine zipper. Leucine zipper domains are peptides that promote oligomerization (dimers and trimers) of the polypeptides in which they are found. Leucine zippers were originally identified in several DNA-binding polypeptides (Landschulz et al., Science 240:1759, 1988), and have since been found in a variety of different polypeptides. The zipper domain comprises a repetitive heptad repeat, often with four or five leucine residues interspersed with other amino acids.

A chimeric or fusion polypeptide of the invention can be produced by standard recombinant DNA techniques. In one embodiment, polynucleotide fragments coding for the different polypeptide sequences are ligated together in-frame in accordance with conventional techniques, for example, by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide).

The invention further includes polypeptides with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the invention in bacterial expression systems, such as E. coli, provides non-glycosylated molecules. Further, a given preparation can include multiple differentially glycosylated species of the polypeptide. Glycosyl groups can be removed through conventional methods, in particular those utilizing glycopeptidase.

In another embodiment, modifications in the polypeptide or polynucleotide can be made using known techniques. Modifications of interest in the polypeptide sequences may include the alteration, substitution, replacement, insertion, or deletion of a selected amino acid residue in the coding sequence. For example, one or more of the cysteine residues may be deleted or replaced with another amino acid to alter the conformation of the molecule, an alteration which may involve preventing formation of incorrect intramolecular disulfide bridges upon folding or renaturation. Techniques for such alteration, substitution, replacement, insertion, or deletion are known to those skilled in the art (see, e.g., U.S. Pat. No. 4,518,584). As another example, N-glycosylation sites in a polypeptide's extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro, and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can by replaced with another amino acid, such as Ala. Known procedures for inactivating N-glycosylation sites in polypeptides include those described in U.S. Pat. No. 5,071,972 and EP 276,846, hereby incorporated by reference. N91 and N101 of SEQ ID Nos: 2, 4, 6, 8, 10, 12, 14, and 16 are putative glycosylation sites. One of skill in the art can identify the triplet residues corresponding to the glycosylation site.

Additional variants within the scope of the invention include polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (detectable) or therapeutic agents attached thereto are contemplated herein. Preferably, such alteration, substitution, replacement, insertion or deletion retains the desired activity of the polypeptide.

The invention also provides polynucleotides encoding CtLL and solCtLL polypeptides. The term "polynucleotide" refers to a polymeric form of nucleotides of at least 10 bases in length. The nucleotides can be ribonucleotides, deoxyribonucleotides, or modified forms of either type of nucleotide. The term includes single and double stranded forms of DNA or RNA. DNA includes, for example, cDNA, genomic DNA, chemically synthesized DNA, DNA amplified by PCR, and combinations thereof. The polynucleotides of the invention include full-length genes and cDNA molecules as well as a combination of fragments thereof. The polynucleotides of the invention are preferentially derived from human sources, but the invention includes those derived from non-human species (e.g., mus musculus), as well.

By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant polynucleotide molecule, which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

A CtLL polynucleotide of the invention (1) encodes a polypeptide comprising a sequence as set forth in SEQ ID NO:2, 4, 6, 8, 10, 12, 14, or 16; (2) has a sequence as set forth in SEQ ID NO:1, 3, 5, 7, 9, 11, 13, or 15; (3) has sequences complementary to a sequence as set forth in SEQ ID NO: 1, 3, 5, 7, 9, 11, 13, or 15; (4) includes fragments of SEQ ID NO: 1, 3, 5, 7, 9, 11, 13, or 15 or a complement that specifically hybridizes to the polynucleotide of (2) or (3) under moderate to highly stringent conditions; and (5) includes polynucleotides of (1), (2), (3), or (4) wherein T can also be U (e.g., RNA sequences). Examples of CtLL polynucleotide fragments of the invention include the nucleotide sequence corresponding to a solCtLL polypeptide. A solCtLL polynucleotide encoding a solCtLL polypeptide comprise a sequence selected from the group consisting of: from about nucleotide 1 to about nucleotide 123 of SEQ ID NO:1, 3, or 13; from about nucleotide 196 to about nucleotide 408 of SEQ ID NO:1 or 13; from about nucleotide 478 to 489 of SEQ ID NO:1; from about nucleotide $x_3$ to about nucleotide $x_4$ of SEQ ID NO:3, wherein $x_3$ is a nucleotide from (and including) about 196 to 427 and $x_4$ is a nucleotide from (and including) about 678 to 699, preferably from about 427 to 678 of SEQ ID NO:3; from about nucleotide 37 to about nucleotide 159 of SEQ ID NO:5; from about nucleotide $x_3$ to about nucleotide $x_4$ of SEQ ID NO:5, wherein $x_3$ is a nucleotide from (and including) about 232 to 463 and $x_4$ is a nucleotide from (and including) about 717 to 732, preferably from about 463 to 717 of SEQ ID NO:5; from about nucleotide 49 to about nucleotide 171 of SEQ ID NO:7 or 11; from about nucleotide 244 to about nucleotide 456 of SEQ ID NO:7; from about nucleotide 526 to about nucleotide 576 of SEQ ID NO:7; from about nucleotide 101 to about nucleotide 223 of SEQ ID NO:9; from about nucleotide $x_3$ to about nucleotide 841 of SEQ ID NO:9, wherein $x_3$ is a nucleotide from (and including) about 296 to 524, preferably from about 524 to 841 of SEQ ID NO:9; from about nucleotide $x_3$ to about nucleotide 876 of SEQ ID NO:11, wherein $x_3$ is a nucleotide from (and including) about 244 to 475, preferably from about 475 to 876 of SEQ ID NO:11; from about nucleotide 478 to about nucleotide 534 of SEQ ID NO:13; from about nucleotide 164 to about nucleotide 286 of SEQ ID NO:15; from about nucleotide 359 to about nucleotide 571 of SEQ ID NO:15; and from about nucleotide 641 to about nucleotide 690 of SEQ ID NO:15. Also encompassed by the invention are homologues of a CtLL polynucleotide of the invention. These polynucleotides can be identified in several ways, including isolation of genomic or cDNA molecules from a suitable source, or computer searches of available sequence databases. Oligonucleotides or polynucleotides corresponding to the amino acid sequences described herein can be used as probes or primers for the isolation of polynucleotide homologues or as query sequences for database searches. Degenerate oligonucleotide sequences can be obtained by "back-translation" from an amino acid sequence of the invention. The polymerase chain reaction (PCR) procedure can be employed to isolate and amplify a DNA sequence encoding a CtLL polypeptide or a desired combination of CtLL polypeptide fragments. Oligonucleotides that define the desired termini of a target DNA molecule are employed as 5' and 3' primers. Accordingly, fragments of the polynucleotides of the invention are useful as probes and primers to identify or amplify related sequence or obtain full-length sequences of a CtLL of the invention.

The oligonucleotides can additionally contain recognition sites for restriction endonucleases, to facilitate insertion of the amplified combination of DNA fragments into an expression vector. PCR techniques are known in the art (see, e.g., *PCR Protocols: A Guide to Methods and Applications*, Innis et. al., eds., Academic Press, Inc. (1990)).

The invention also includes polynucleotides and oligonucleotides that hybridize under reduced stringency conditions, more preferably moderately stringent conditions, and most preferably highly stringent conditions, to CtLL polynucleotides described herein. The basic parameters affecting the choice of hybridization conditions and guidance for devising suitable conditions are set forth by Sambrook, J., E. F. Fritsch, and T. Maniatis (1989, *Molecular Cloning: A Laboratory Manual*, Cold Spring Harbor Laboratory Press, Cold Spring Harbor, N.Y., chapters 9 and 11; and *Current Protocols in Molecular Biology*, 1995, Ausubel et al., eds., John Wiley & Sons, Inc., sections 2.10 and 6.3-6.4, incorporated herein by reference), and can be readily determined by those having ordinary skill in the art based on, for example, the length and/or base composition of the polynucleotide. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target polynucleotide of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids above 18 base pairs in length, $T_m$ (° C.)=81.5+16.6 (log$_{10}$[Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 25% (more preferably at least 50%, 60%, or 70%, and most preferably at least 80%) of the length of a polynucleotide of the invention to which it hybridizes, and has at least 60% sequence identity (more preferably at least 70%, 75%, 80%, 85%, 90%, 95%, 97.5%, or at least 99%, and most preferably at least 99.5%) with a polynucleotide of the invention to which it hybridizes.

"Conservatively modified variants" applies to both polypeptide and polynucleotide. With respect to particular polynucleotide, conservatively modified variants refer to codons in the polynucleotide which encode identical or essentially identical amino acids. Because of the degeneracy of the genetic code, a large number of functionally identical polynucleotides encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such variations are "silent variations," which are one species of conservatively modified variations. Every polynucleotide sequence herein that encodes a polypeptide also describes every possible silent variation of the nucleic acid. One of skill will recognize that each codon in a polynucleotide (except AUG, which is ordinarily the only codon for methionine) can be modified to yield a functionally identical molecule. Accordingly, each silent variation of a nucleic acid that encodes a polypeptide is implicit in each described sequence.

The invention also provides methodology for analysis of polynucleotides of the invention, or fragments thereof, on "DNA chips" as described in Hacia et al., Nature Genetics, 14:441-447 (1996). For example, high-density arrays of oligonucleotides comprising a sequence as set forth in SEQ ID NO:1, or a variant or mutant thereof, are applied and immobilized to the chip and can be used to detect sequence variations in a population. Polynucleotides in a test sample are hybridized to the immobilized oligonucleotides. The hybridization profile of the target polynucleotide to the immobilized probe is quantitated and compared to a reference profile. The resulting genetic information can be used in molecular diagnosis. The density of oligonucleotides on DNA chips can be modified as needed.

The invention also provides genes corresponding to the polynucleotides disclosed herein. "Corresponding gene regions" are the regions of the genome that are transcribed to produce the mRNAs from which cDNA molecules are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Expression, isolation, and purification of the polypeptides and fragments of the invention can be accomplished by any suitable technique, including but not limited to the following methods.

The isolated polynucleotides of the invention may be operably linked to an expression control sequence such as the pMT2 or pED expression vectors disclosed in Kaufman et al., Nucleic Acids Res. 19:4485 (1991); and Pouwels et al. *Cloning Vectors: A Laboratory Manual*, Elsevier, New York, (1985, and Supplements), in order to produce a polypeptide of the invention recombinantly. Many suitable expression control sequences are known in the art. General methods of expressing recombinant polypeptides are also known and are exemplified in R. Kaufman, Methods in Enzymology 185: 537 (1990). As defined herein "operably linked" means that an isolated polynucleotide of the invention and an expression control sequence are situated within a vector or cell in such a way that the polypeptide encoded by the polynucleotide is expressed by a host cell which has been transformed (transfected) with the vector or polynucleotide operably linked to the control sequence.

In addition, a sequence encoding an appropriate localization (signal) peptide (native or heterologous) can be incorporated into expression vectors. The choice of signal peptide or leader can depend on factors such as the type of host cells in which the recombinant polypeptide is to be produced. Examples of heterologous localization (signal) peptides that are functional in mammalian host cells include the signal sequence for interleukin (IL)-7 (see, U.S. Pat. No. 4,965, 195); the signal sequence for IL-2 receptor (see, Cosman et al., Nature 312:768, 1984); the IL4 receptor signal peptide (see, EP 367,566); the type I IL-1 receptor signal peptide (see, U.S. Pat. No. 4,968,607); and the type II IL-1 receptor signal peptide (see, EP 460,846). A signal peptide that is functional in the intended host cells promotes extracellular secretion of the polypeptide. The signal peptide is cleaved from the polypeptide upon secretion of a polypeptide from the cell. A polypeptide preparation can include a mixture of polypeptide molecules having different N-terminal amino acids, resulting from cleavage of the signal peptide at more than one site.

Established methods for introducing DNA into mammalian cells have been described (Kaufman, R. J., *Large Scale Mammalian Cell Culture*, 1990, pp. 15-69). Additional protocols using commercially available reagents, such as Lipofectamine or Lipofectamine-Plus lipid reagent (Gibco/BRL), can be used to transfect cells (Felgner et al., *Proc. Natl. Acad. Sci. USA* 84:7413, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487, 1990, describes several selection schemes, such as dihydrofolate reductase (DHFR) resistance. A suitable strain for DHFR selection can be CHO strain DX-B11, which is deficient in DHFR (Urlaub et al., *Proc. Natl. Acad. Sci. USA* 77:4216, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector are selected on the basis of resistance to these compounds.

Alternatively, gene products can be obtained via homologous recombination, or "gene targeting" techniques. Such techniques employ the introduction of exogenous transcription control elements (such as the CMV promoter or the like) in a particular predetermined site on the genome, to induce expression of an endogenous CtLL of the invention. The location of integration into a host chromosome or genome can be easily determined by one of skill in the art, given the known location and sequence of the gene. In another embodiment, the invention also contemplates the introduction of exogenous transcriptional control elements in conjunction with an amplifiable gene, to produce increased amounts of the gene product. The practice of homologous recombination or gene targeting is explained by Schimke, et al. "*Amplification of Genes in Somatic Mammalian cells*," Methods in Enzymology 151:85 (1987), and by Capecchi, et al., "*The New Mouse Genetics: Altering the Genome by Gene Targeting*," TIG 5:70 (1989).

Suitable host cells for expression of the polypeptide include eukaryotic and prokaryotic cells. Mammalian host cells include, for example, the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) (see, McMahan et al. *EMBO J.* 10: 2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it may be possible to produce the polypeptide in lower eukaryotes such as yeast or in prokaryotes such as bacteria. Potentially suitable yeast strains include *Saccharomyces cerevisiae, Schizosaccharomyces pombe, Kluyveromyces strains, Candida*, or any yeast strain capable of expressing heterologous polypeptides. Potentially suitable bacterial strains include, for example, *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptide may also be produced by operably linking a polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), as well as methods described in Summers and Smith, Texas Agricultural Experiment Station Bulletin No. 1555 (1987), and Luckow and Summers, *Bio/Technology* 6:47 (1988), incorporated herein by reference. Cell-free translation systems could also be employed to produce polypeptides using RNAs derived from nucleic acid constructs disclosed herein. A host cell that comprises an isolated polynucleotide of the invention, preferably operably linked to at least one expression control sequence, is a "recombinant host cell".

In some instances it may be advantageous to suppress CtLL expression or to inhibit the interaction of CtLL with a target cell or ligand. For instance, suppression of a CtLL polynucleotide sequence may alleviate damage associated with over expression or excess CtLL activity in the immune system and would be beneficial in the activation of the immune system for the treatment of tumors and cells carrying a pathogen (e.g., virally-infected cells). Blocking an inhibitory activity of a CtLL polypeptide using antisense or ribozyme technology to reduce expression of a CtLL polypeptides would be one method of promoting such a response. Other diseases and disorders where modulation of CtLL polypeptide expression or activity include chronic rejection of transplanted tissues and organs, or in atherosclerosis and inflammatory responses mediated with plaque formation in vascular tissue. CtLL expression can be suppressed by administration of CtLL antisense oligonucleotides.

In contrast, strong responses to normal cellular components including the oxidized lipids themselves would be expected to play a pathological role. Accordingly, an activator of CtLL activity or expression can play a role in the prevention of autoimmune diseases involving cell apoptosis such as diabetes and vascular diseases. For example, activating the expression or activity of CtLL would increase the inhibitory activity thereby reducing the immune systems response to such non-self or diseased cells.

Due to the identity that the CtLL polypeptide have to other C-type lectins the CtLL polypeptides may also play a role in pathogenesis due to infection. For example, pathogenic *Mycobacteria*, including *M. tuberculosis*, colonize in activated macrophages. The attachment of such pathogens to the activated macrophages is a preliminary step in pathogenesis. Preventing this interaction may provide an important approach for blocking the colonization of host macrophages by pathogenic bacteria or parasites. In another embodiment, plaque formation associated with athersclerosis may be prevented by preventing the interaction of CtLL with its cognate by using antibodies to CtLL or by the administration of a solCtLL that binds the cognate and prevents interaction of the cognate with the naturally occurring CtLL.

In a one embodiment, a soluble fragment of CtLL consisting primarily of the extracellular region binding domain may be used as an inhibitor of native CtLL or in the prevention of interaction of CtLL with a cognate (e.g., an oxidized lipid). The structural integrity of the isolated extracellular domain would be maintained by the intrachain disulfide bonds. When administered, the soluble binding domain can block CtLL-target cell interactions by competing with native CtLL for ligands on the surface of the target cell.

CtLL may be exploited for the purposes of targeted drug delivery. Anti-pathogen and anti-parasite therapies are hampered by the sequestering of the pathogenic bacteria or parasites within infected cell types (e.g., macrophages), restricting the bioavailability of potentially useful drugs. A drug may be targeted to the infected cell by means of an anti-CtLL antibody covalently attached to a drug, which would bind to CtLL expressed on the surface of the cell (e.g., macrophage). The CtLL-bound antibody conjugate would subsequently be internalized into the infected macrophage, enhancing the bioavailability and efficacy of the drug. Alternatively, a pathogen that binds to a CtLL can be targeted by linking a drug to a soluble form of the CtLL such that the soluble form interacts with the cognate on the pathogen that typically interacts with a native CtLL, thus bringing the drug linked to the soluble form in contact with the pathogen.

Macrophages or other immune cells expressing CtLL could alternatively serve as conduits for the directed delivery of therapeutic agents to diseased cells. The therapeutic agent, or the gene encoding the therapeutic agent, may be introduced into such immune cells expressing CtLL. The immune cells would interact specifically with diseased cells displaying surface molecules recognized by CtLL, delivering the drug when endocytosis of the diseased target cell occurred. CtLL may also be incorporated into lipid vesicles containing a therapeutic agent. The vesicles would interact with diseased cells or cells bearing a CtLL ligand, delivering the drug to the desired target.

Tumor cells may be treated with agents to alter the structures of target cell-surface carbohydrates or lipids to enhance the specificity of target cell/macrophage recognition via CtLL. This is particularly advantageous if CtLL recognizes "unusual" sugars or recognizes oxidized lipids which are not normally present in the host, but can be produced in tumor cells by the administration of drugs that alter the synthesis of surface carbohydrates or oxidize the lipids on the cells surface in the rapidly-growing tumor cells.

CtLL-specific antibodies are useful for the diagnosis of conditions and diseases associated with expression of CtLL. The CtLL polypeptides, fragments, variants, fusion polypeptides, and the like, as set forth above, can be employed as "immunogens" in producing antibodies immunoreactive therewith. Such antibodies specifically bind to the polypeptides via the antigen-binding sites of the antibody. Specifically binding antibodies are those that will specifically recognize and bind with C-type lectin family polypeptides, homologues, and variants, but not with other molecules. In one embodiment, the antibodies are specific for polypeptides having a CtLL amino acid sequence of the invention and do not cross-react with other polypeptides including other C-type lectin.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides of the invention can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides of the invention can be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kosbor et al., Immunology Today 4:72, 1983; Cole et al., Proc. Natl. Acad. Sci. USA 80:2026, 1983); and the EBV-hybridoma technique (Cole et al., 1985, Monoclonal Antibodies And Cancer Therapy, Alan R. Liss, Inc., pp. 77-96). Hybridoma cell lines that produce monoclonal antibodies specific for the polypeptides of the invention are also contemplated herein. Such hybridomas can be produced and identified by conventional techniques. For the production of antibodies, various host animals may be immunized by injection with a CtLL polypeptide, fragment, variant, or mutants thereof. Such host animals may include, but are not limited to, rabbits, mice, and rats, to name a few. Various adjutants may be used to increase the immunological response. Depending on the host species, such adjutants include, but are not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjutants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

In addition, techniques developed for the production of "chimeric antibodies" (Takeda et al., Nature, 314:452, 1985) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the invention also include humanized versions of murine monoclonal antibodies. Such humanized antibodies can be prepared by known techniques and offer the advantage of reduced immunogenicity when the antibodies are administered to humans. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, Can, 1993). Procedures to generate antibodies transgenically can be found in GB 2,272,440, U.S. Pat. Nos. 5,569,825 and 5,545,806 and related patents claiming priority therefrom, all of which are incorporated by reference herein. When antibodies are used in humans the antibodies are human or humanized; techniques for creating such human antibodies are also known. Transgenic animals for making human antibodies are available from, for example, Medarex Inc. (Princeton, N.J.) and Abgenix Inc. (Fremont, Calif.).

Antibody fragments, which recognize specific epitopes, may be generated by known techniques. For example, such fragments include but are not limited to: the $F(ab')_2$ fragments which can be produced by pepsin digestion of the antibody molecule and the Fab fragments which can be generated by reducing the disulfide bridges of the $(ab')_2$ fragments. Alternatively, Fab expression libraries may be constructed (Huse et al., Science, 246:1275, 1989) to allow rapid and easy identification of monoclonal Fab fragments with the desired specificity. Techniques described for the production of single chain antibodies (U.S. Pat. No. 4,946,778; Bird, Science 242:423, 1988; Huston et al., Proc. Natl. Acad. Sci. USA 85:5879, 1988; and Ward et al., Nature 334:544, 1989) can also be adapted to produce single chain antibodies against polypeptides containing CtLL amino acid sequences. In addition, antibodies to a CtLL polypeptide can, in turn, be utilized to generate anti-idiotype antibodies that "mimic" a CtLL polypeptide and that may bind to a CtLL polypeptide using techniques known to those skilled in the art. (See, e.g., Greenspan & Bona, FASEB J 7(5):437, 1993; and Nissinoff, J. Immunol. 147(8):2429, 1991).

Screening procedures to identify such antibodies are known, and can involve immunoaffinity chromatography, for example. Antibodies can be screened for agonistic (i.e., ligand-mimicking) properties. Such antibodies, upon binding to a CtLL polypeptide on the cell surface, can induce biological effects (e.g., transduction of biological signals resulting in activation of a phosphatase) similar to the biological effects induced when the naturally occurring CtLL binding partner binds to the polypeptide on the cell surface. Agonistic antibodies can be used to induce CtLL mediated co-stimulatory pathways or intercellular communication.

In addition, antibodies that block binding of a polypeptide having a CtLL sequence of the invention to its binding partner can be used to inhibit CtLL mediated intercellular communication or co-stimulation that results from such binding and/or to identify carbohydrate or lipid cognates of CtLL. Such blocking antibodies can be identified using any suitable assay procedure, such as by testing antibodies for the ability to inhibit binding of a CtLL polypeptide to certain cells expressing a binding partner (e.g., an oxidized lipid and/or a carbohydrate containing protein) to the polypeptide or by measuring agglutination in the presence and absence of the antibody, wherein reduction or inhibition of agglutination is indicative of an antibody that blocks interaction of CtLL with its binding partner. Alternatively, blocking antibodies can be identified in assays for the ability to inhibit a biological effect that results from binding of a CtLL polypeptide to target cells.

Disorders caused or exacerbated (directly or indirectly) by the interaction of CtLL with a cell surface-binding partner or a binding partner on a pathogen can thus be treated. A therapeutic method involves in vivo administration of a blocking antibody to a subject in an amount effective to inhibit CtLL binding-mediated biological activity. As used herein, a "subject" can be any animal, preferably a mammal (e.g., canine, feline, bovine, porcine, equine, primates, and the like), and most preferably a human. Monoclonal antibodies are generally preferred for use in such therapeutic methods. In one embodiment, an antigen-binding antibody fragment is employed. Compositions comprising an antibody against a CtLL polypeptide, and a physiologically acceptable diluent, excipient, or carrier, are provided herein.

Also provided herein are conjugates comprising a detectable (e.g., diagnostic) or therapeutic agent attached to the antibody. The conjugates find use in in vitro or in vivo procedures. The antibodies of the invention can also be used in assays to detect the presence of the polypeptides or fragments of the invention, either in vitro or in vivo. The antibodies also can be employed in purifying polypeptides or fragments of the invention by immunoaffinity chromatography.

In another embodiment, rational drug design is used to produce structural analogs of biologically active polypeptides of interest or of small molecules with which they interact, e.g., substrates, binding agents, inhibitors, agonists, antagonists, and the like. The methods provided herein can be used to fashion or identify agents which are more active or stable forms of the polypeptide or which enhance or interfere with the function of a polypeptide in vivo (Hodgson J, Biotechnology 9:19, 1991, incorporated herein by reference). In one approach, the three-dimensional structure of a polypeptide of the invention, a ligand or binding partner, or of a polypeptide-binding partner complex, is determined by x-ray crystallography, by nuclear magnetic resonance, or by computer homology modeling or, most typically, by a combination of these approaches. Relevant structural information is used to design analogous molecules, to identify efficient inhibitors, or to identify small molecules that may bind to a polypeptide of the invention. The use of C-type lectin, OLR1, CLEC1, and/or, CLEC2 polypeptide structural information, preferably CtLL structural information, in molecular modeling software systems provides for the design of inhibitors or binding agents useful in modulating CtLL activity. A particular method of the invention comprises analyzing the three dimensional structure of CtLL polypeptides for likely binding sites of substrates or ligands, synthesizing a new molecule that incorporates a predictive reactive site, and assaying the new molecule as described further herein. Examples of algorithms, software, and methods for modeling substrates or binding agents based upon the three-dimensional structure of a protein are described in PCT publication WO107579A2, the disclosure of which is incorporated herein.

It is also possible to isolate a target-specific antibody, selected by a functional assay, as described further herein, and then to solve its crystal structure thus yielding a pharmacore upon which subsequent drug design can be based. It is possible to bypass polypeptide crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

CtLL antibodies are useful for the diagnosis of conditions or diseases characterized by expression of CtLL or in assays to monitor patients being treated with CtLL agonists or inhibitors. Diagnostic assays for CtLL include methods utilizing the antibody and a label to detect CtLL in biological samples (e.g., body fluids, cells, or tissues). The polypeptides and antibodies of the present invention may be used with or without modification. Frequently, the polypeptides and antibodies will be labeled by joining them, either covalently or noncovalently, with a reporter molecule. A wide variety of reporter molecules are known including enzymatic labels, fluorescent labels, radioactive labels, and the like. A variety of protocols for measuring CtLL, using either polyclonal or monoclonal antibodies are known in the art. Examples include enzyme-linked immunosorbent assay (ELISA), radioimmunoassay (RIA) and fluorescent activated cell sorting (FACS). Diagnosis or prognosis is performed by quantitating the amount of CtLL in a sample compared to a control or normal sample. A difference in an amount of CtLL in the test sample compared to a control is indicative of a difference in expression of CtLL and is indicative of a disease state.

The invention provides methods for identifying agents that modulate CtLL activity or expression. Such methods included contacting a sample containing a CtLL polypeptide or polynucleotide with a test agent under conditions that allow for the test agent and the polynucleotide or polypeptide to interact, and then measuring the expression or activity, respectively, of a CtLL polypeptide in the presence or absence of the test agent.

In one embodiment, a cell containing a CtLL polynucleotide is contacted with a test agent under conditions such that the cell and test agent are allowed to interact. Such conditions typically include normal cell culture conditions consistent with the particular cell type being utilized and which are known in the art. It may be desirable to allow the test agent and cell to interact under conditions associated with increased temperature or in the presence of regents that facilitate the uptake of the test agent by the cell. A control is treated similarly but in the absence of the test agent. Alternatively, the CtLL activity or expression may be measured prior to contact with the test agent (e.g., the standard or control measurement) and then again following contact with the test agent. The treated cell is then compared to the control and a difference in the expression or activity of CtLL compared to the control is indicative of an agent that modulates CtLL activity or expression.

When CtLL expression is being measured, detecting the amount of mRNA encoding a CtLL polypeptide in the cell can be quantified by, for example, PCR or Northern blot. Where a change in the amount of CtLL polypeptide in the sample is being measured, detecting CtLL by use of anti-CtLL antibodies can be used to quantify the amount of CtLL polypeptide in the cell using known techniques.

A test agent can be any molecule typically used in the modulation of protein activity or expression and includes, for example, small molecules, chemicals, peptidomimetics, antibodies, peptides, polynucleotides (e.g., antisense or ribozyme molecules), and the like. Accordingly, agents developed by computer based drug design can be tested in the laboratory using the assay and methods described herein to determine the activity of the agent on the modulation of CtLL activity or expression. Modulation of CtLL includes an increase or decrease in activity or expression.

A CtLL polypeptide of the invention (including fragments, variants, oligomers, and other forms) are useful in a variety of assays. For example, a CtLL of the invention can be used to identify binding partners of members of the C-type lectin family of polypeptides, which can also be used to modulate intercellular communication, co-stimulation, macrophage activity, or pathogen infectivity.

CtLL polypeptides and fragments thereof can be used to identify binding partners. For example, they can be tested for the ability to bind a candidate-binding partner in any suitable assay, such as a conventional binding assay. To illustrate, a CtLL polypeptide or fragment thereof (preferably a soluble portion corresponding to an extracellular of soluble domain of CtLL) can be labeled with a detectable molecule (e.g., a radionuclide, a chromophore, or an enzyme that catalyzes a colorimetric or fluorometric reaction, and the like). The labeled polypeptide is contacted with cells expressing the candidate-binding partner. The cells then are washed to remove unbound-labeled polypeptide, and the presence of cell-bound label is determined by a suitable technique, chosen according to the nature of the label.

In one embodiment, a binding partner is identified by the use of antibodies to the binding partner. The ability of anti-binding partner antibody to inhibit the binding of CtLL polypeptides reveal the binding partner and, indirectly, which binding activities are antagonize. CtLL polypeptides or fragments thereof that bind to select binding partners are further tested for the ability to disrupt interactions with, for example, a pathogen, and to modulate other biological activities in vitro and in vivo.

In another example of a binding assay, a recombinant expression vector containing the candidate binding partner cDNA is transfected into CV1-EBNA-1 cells. The cells are incubated for 1 hour at 37° C. with various concentrations of, for example, a soluble CtLL polypeptide/Fc fusion polypeptide. Cells are washed and incubated with a constant saturating concentration of a $^{125}$I-mouse anti-human IgG. After washing, cells are released via trypsinization. The mouse anti-human IgG employed above is directed against the Fc region of human IgG and can be obtained from Jackson Immunoresearch Laboratories, Inc., West Grove, Pa. The antibody will bind to the Fc portion of any Fc polypeptide that has bound to the cells. Cell-bound $^{125}$I-antibody is quantified on a Packard Autogamma counter.

Where a CtLL polypeptide binds or potentially binds to another polypeptide (e.g., in a receptor-ligand interaction), the CtLL polynucleotide can also be used in interaction trap assays (see, e.g., Gyuris et al., Cell 75:791, 1993) to identify polynucleotides encoding the other polypeptide with which binding occurs or to identify inhibitors of the binding interaction. Polypeptides involved in these binding interactions can also be used to screen for peptide or small molecule inhibitors or agonists of the binding interaction.

Another type of suitable binding assay is a competitive binding assay. To illustrate, biological activity of a variant can be determined by assaying for the variant's ability to compete with the native polypeptide for binding to the candidate-binding partner. Competitive binding assays can be performed by conventional methodology. Reagents that can be employed in competitive binding assays include a radiolabeled CtLL fragment or variant and intact cells expressing CtLL (endogenous or recombinant) on the cell surface. Instead of intact cells, one could substitute a soluble binding partner/Fc fusion polypeptide bound to a solid phase through the interaction of Polypeptide A or G (on the solid phase) with the Fc moiety. Chromatography columns that contain Polypeptide A and G include those available from Pharmacia Biotech, Inc., Piscataway, N.J.

The influence of CtLL polypeptides, CtLL fragments (e.g., solCtLL) and antibodies on intercellular communication, co-stimulation, pathogen infection/progression, or immune cell activity can be assayed by contacting a cell or a group of cells with a polynucleotide, polypeptide, agonist or antagonist, to induce, enhance, suppress, or arrest intercellular communication, co-stimulation, pathogen infection/progression, or immune cell activity in the target cells. Identification of CtLL polypeptides, agonists or antagonists can be carried out via a variety of assays known to those skilled in the art. Included in such assays are those that evaluate the ability of a CtLL polypeptide or solCtLL to influence intercellular communication, co-stimulation, pathogen infection/progression, or immune cell activity. Such an assay would involve, for example, the analysis of cell-cell interactions, pathogen-cell interactions in the presence of a CtLL polypeptide or soluble fragment thereof. In one assay, the modulation of a phosphatase activated by the ITIM moiety can be determined as a measure of activity. In another assay, one would determine a rate of cell-cell interaction or cell-pathogen interaction in the presence of a polypeptide having a CtLL sequence and then determine if such binding or interaction is altered in the presence of, e.g., a soluble CtLL sequence.

In one aspect, the invention provides a method of detecting the ability of a test agent to affect, for example, phosphatase activity in a cell or culture. In this aspect, the method comprises: (1) contacting a group of target cells with a test agent including a polypeptide comprising a CtLL sequence (e.g., SEQ ID NO: 2, 4, 6, 8, 10, 12, 14 or 16 or a solCtLL), a ligand or receptor for a CtLL polypeptide, or fragment thereof, under conditions appropriate to the particular assay being used; (2) measuring the net rate of, for example, phosphatase activity using methods standard in the art; and (3) observing the phosphatase activity among a group of control cells containing a CtLL polypeptide ligand or fragments thereof, in the absence of a test agent, under otherwise identical conditions as the first group of cells. The test agent can function as an effector by either activating or up-regulating, or by inhibiting or down-regulating phosphatase activity. To test the capacity of a solCtLL polypeptide to phosphatase activity, such soluble polypeptides will be added to a coculture systems containing immune cells (e.g., macrophages, DCs, T-cells and the like). Agents that inhibit immune cell activation, as assessed by measuring phosphatase activity, proliferation, or cytokine secretion, can be considered CtLL agonist.

In another aspect, the invention provides a method of detecting the ability of a test agent to affect, for example, the cell-cell interaction or cell-pathogen activity of the test agent on a cell or culture. In this aspect, the method comprises: (1) contacting a group of target cells with a test agent including a polypeptide comprising a CtLL sequence (e.g., SEQ ID NO: 2, 4, 6, 8, 10, 12, 14 or 16 or a solCtLL binding moiety, as described above), a ligand or receptor for a CtLL polypeptide, or fragment thereof, under conditions appropriate to the particular assay being used; (2) measuring the net rate of, for example, cell-cell interaction or cell-pathogen interactions; and (3) observing the net rate of cell-cell interaction or cell-pathogen interactions among a group of control cells containing a CtLL polypeptide ligand or fragments thereof, in the absence of a test agent, under otherwise identical conditions as the first group of cells. The comparison will provide a difference in the net rate of, for example, cell-cell or cell-pathogen interaction indicative of an agent that modulates CtLL activity. The test agent can function as an effector by either activating or up-regulating, or by inhibiting or down-regulating cell-cell interaction or cell-pathogen interaction. To test the capacity of a solCtLL polypeptide to inhibit cell-cell interaction, such soluble polypeptides will be added to a coculture systems that contain the cells to be tested (and antigen, if required). Samples that inhibit T or B cell activation, for example, as assessed by proliferation or cytokine secretion by T or B cells, will be considered to have the capacity to block the cell interaction.

A polypeptide of the invention may exhibit cytokine production or inhibition activity, cell proliferation (either inducing or inhibiting) activity, or cell differentiation (either inducing or inhibiting) activity. Many polypeptide factors discovered to date, including most cytokines, have exhibited activity in one or more cell proliferation assays, and hence the assays serve as a convenient confirmation of cytokine activity. The activity of a CtLL or solCtLL polypeptide of the invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CtLL2, TF-1, Mo7e and CMK. The activity of a CtLL or a solCtLL polypeptide of the invention may be measured by the following methods:

Assays for T-cell or thymocyte proliferation include, without limitation, those described in: Current Protocols in Immunology, Ed. by Coligan et al., Pub. Greene Publishing Associates and Wiley-Interscience (Chapter 3, In vitro assays for Mouse Lymphocyte Function 3.1-3.19; Chapter 7, Immunologic studies in Humans); Takai et al., J. Immunol. 137:3494, 1986; Bertagnolli et al., J. Immunol. 145:1706, 1990; Bertagnolli et al., Cell. Immunol. 133:327, 1991; Bertagnolli, et al., J. Immunol. 149:3778, 1992; Bowman et al., J. Immunol. 152: 1756, 1994.

Assays for cytokine production and/or proliferation of spleen cells, lymph node cells or thymocytes include, without limitation, those described in: Polyclonal T cell stimulation, Kruisbeek and Shevach, Vol 1 pp. 3.12.1-3.12.14, and Measurement of mouse and human Interferon γ, Schreiber, Vol 1 pp. 6.8.1-6.8.8. In Current Protocols in Immunology. Coligan eds. John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly et al., In Current Protocols in Immunology. Coligan eds. Vol 1 pp. 6.3.1-6.3.12, John Wiley and Sons, Toronto. 1991; deVries et al., J. Exp. Med. 173:1205, 1991; Moreau et al., Nature 336:690, 1988; Greenberger et al., Proc. Natl. Acad. Sci. U.S.A. 80:2931, 1983; Measurement of mouse and human interleukin 6, Nordan, In Current Protocols in Immunology. Coligan eds. Vol 1 pp. 6.6.1-6.6.5, John Wiley and Sons, Toronto. 1991; Smith et al., Proc. Natl. Acad. Sci. U.S.A. 83:1857, 1986; Measurement of human Interleukin 11, Bennett et al., In Current Protocols in Immunology. Coligan eds. Vol 1 pp. 6.15.1 John Wiley and Sons, Toronto. 1991; Measurement of mouse and human Interleukin 9, Ciarletta et al., In Current Protocols in Immunology. Coligan eds. Vol 1 pp. 6.13.1, John Wiley and Sons, Toronto. 1991.

Assays for T-cell clone responses to antigens (which will identify, among others, polypeptides that affect APC-T cell interactions as well as direct T-cell effects by measuring proliferation and cytokine production) include, without limitation, those described in: Current Protocols in Immunology, Coligan eds., Pub. Greene Publishing Associates and Wiley-Interscience (Chapter 3, Chapter 6, Chapter 7); Weinberger et al., Proc. Natl. Acad. Sci. USA 77:6091, 1980; Weinberger et al., Eur. J. Immun. 11:405, 1981; Takai et al., J. Immunol. 137:3494, 1986; Takai et al., J. Immunol. 140:508, 1988.

Assays for thymocyte or splenocyte cytotoxicity include, without limitation, Current Protocols in Immunology, Coligan eds., Pub. Greene Publishing Associates and Wiley-Interscience (pp. 3.1-3.19; Chapter 7); Herrmann et al., Proc. Natl. Acad. Sci. USA 78:2488, 1981; Herrmann et al., J. Immunol. 128:1968, 1982; Handa et al., J. Immunol. 135:1564, 1985; Takai et al., J. Immunol. 137:3494, 1986; Takai et al., J. Immunol. 140:508, 1988; Bowman et al., J. Virol. 61:1992; Bertagnolli et al., Cell. Imm. 133:327, 1991; Brown et al., J. Immunol. 153:3079, 1994.

Assays for T-cell-dependent IgG responses and isotype switching (which will identify, among others, polypeptides that modulate T-cell dependent antibody responses and that affect Th1/Th2 profiles) include, without limitation, those described in: Maliszewski, J. Immunol. 144:3028, 1990; and Assays for B cell function: In vitro antibody production, Mond and Brunswick, In Current Protocols in Immunology. Coligan eds. Vol 1 pp. 3.8.1-3.8.16, Wiley and Sons, Toronto. 1994.

Mixed lymphocyte reaction (MLR) assays (which will identify, among others, polypeptides that generate predominantly Th1 and CTL responses) include, without limitation, those described in: Current Protocols in Immunology, Coligan eds., Pub. Greene Publishing Associates and Wiley-Interscience (In vitro assays for Mouse Lymphocyte Function pp 3.1-3.19; Chapter 7, Immunologic studies in Humans); Takai et al., 1986, supra; Takai et al., 1988, supra; Bertagnolli et al., J. Immunol. 149:3778, 1992.

Dendritic cell-dependent assays (which will identify, among others, polypeptides expressed by dendritic cells that activate naive T-cells) include, without limitation, those described in: Guery et al., J. Immunol. 134:536, 1995; Inaba et al., J. of Exp. Med. 173:549, 1991; Macatonia et al., J. Immunol. 154:5071, 1995; Porgador et al., J. of Exp. Med. 182:255, 1995; Nair et al., J. Virol. 67:4062, 1993; Huang et al., Science 264:961, 1994; Macatonia et al., J. of Exp. Med. 169:1255, 1989; Bhardwaj et al., J. Clin. Invest. 94:797, 1994; and Inaba et al., J. of Exp. Med. 172:631, 1990.

Assays for lymphocyte survival/apoptosis (which will identify, among others, polypeptides that prevent apoptosis after superantigen induction and polypeptides that regulate lymphocyte homeostasis) include, without limitation, those described in: Darzynkiewicz et al., Cytometry 13:795, 1992; Gorczyca et al., Leukemia 7:659, 1993; Gorczyca et al., Cancer Research 53:1945, 1993; Itoh et al., Cell 66:233, 1991; Zacharchuk, J. Immunol. 145:4037, 1990; Zamai et al., Cytometry 14:891, 1993; Gorczyca et al., Int. J. of Oncology 1:639, 1992.

Assays for polypeptides that influence early steps of T-cell commitment and development include, without limitation, those described in: Antica et al., Blood 84:111, 1994; Fine et al., Cell. Immunol. 155:111, 1994; Galy et al., Blood 85:2770, 1995; Toki et al., Proc. Nat. Acad Sci. USA 88:7548, 1991.

Assays for embryonic stem cell differentiation (which will identify, among others, polypeptides that influence embryonic differentiation hematopoiesis) include, without limitation, those described in: Johansson et al. Cell. Biol. 15:141, 1995; Keller et al., Mol. and Cell. Biol. 13:473, 1993; McClanahan et al., Blood 81:2903, 1993.

Assays for stem cell survival and differentiation (which will identify, among others, polypeptides that regulate lympho-hematopoiesis) include, without limitation, those described in: Methylcellulose colony forming assays, Freshney, M. G. In Culture of Hematopoietic Cells. R. I. Freshney, et al. eds. Vol pp. 265-268, Wiley-Liss, Inc., New York, N.Y. 1994; Hirayama et al., Proc. Natl. Acad. Sci. USA 89:5907-5911, 1992; Primitive hematopoietic colony forming cells with high proliferative potential, McNiece and Briddell, In Culture of Hematopoietic Cells. R. I. Freshney, et al. eds. Vol pp. 23-39, Wiley-Liss, Inc., New York, N.Y. 1994; Neben et al., Exp. Hematol. 22:353, 1994; Cobblestone area forming cell assay, Ploemacher, In Culture of Hematopoietic Cells. Freshney, et al. eds. Vol pp. 1-21, Wiley-Liss, Inc., New York, N.Y. 1994; Long term bone marrow cultures in the presence of stromal cells, Spooncer et al. In Culture of Hematopoietic Cells. Freshney, et al. eds. Vol pp. 163-179, Wiley-Liss, Inc., New York, N.Y. 1994; Long term culture initiating cell assay, Sutherland, In Culture of Hematopoietic Cells. Freshney, et al. eds. Vol pp. 139-162, Wiley-Liss, Inc., New York, N.Y. 1994.

Assays for tissue generation activity include, without limitation, those described in: Patent Publication No. WO95/16035 (bone, cartilage, tendon); Patent Publication No. WO95/05846 (nerve, neuronal); Patent Publication No. WO91/07491 (skin, endothelium). Assays for wound healing activity include, without limitation, those described in: Winter, Epidermal Wound Healing, pps. 71-112 (Maibach, and Rovee, eds.), Year Book Medical Publishers, Inc., Chicago, as modified by Eaglstein and Mertz, J. Invest. Dermatol 71:382-84 (1978).

Assays for activin/inhibin activity include, without limitation, those described in: Vale et al., Endocrinol. 91:562, 1972; Ling et al., Nature 321:779, 1986; Vale et al., Nature 321:776, 1986; Mason et al., Nature 318:659, 1985; Forage et al., Proc. Natl. Acad. Sci. USA 83:3091, 1986.

Assays for cell movement and adhesion include, without limitation, those described in: Current Protocols in Immunology, Coligan eds., Pub. Greene Publishing Associates and Wiley-Interscience (Chapter 6, 6.12.1-6.12.28); Taub et al. J. Clin. Invest. 95:1370, 1995; Lind et al. APMIS 103:140, 1995; Muller et al. Eur. J. Immunol. 25: 1744; Gruber et al. J. Immunol. 152:5860, 1994; Johnston et al. J. Immunol. 153: 1762, 1994.

Assay for hemostatic and thrombolytic activity include, without limitation, those described in: Linet et al., J. Clin. Pharmacol. 26:131, 1986; Burdick et al., Thrombosis Res. 45:413, 1987; Humphrey et al., Fibrinolysis 5:71, 1991; Schaub, Prostaglandins 35:467, 1988.

Assays for receptor-ligand activity include, without limitation, those described in: Current Protocols in Immunology, Coligan eds., Pub. Greene Publishing Associates and Wiley-Interscience (Chapter 7.28.1-7.28.22), Takai et al., Proc. Natl. Acad. Sci. USA 84:6864, 1987; Bierer et al., J. Exp. Med. 168:1145, 1988; Rosenstein et al., J. Exp. Med. 169:149, 1989; Stoltenborg et al., J. Immunol. Methods 175:59, 1994; Stitt et al., Cell 80:661, 1995.

Assays for cadherin adhesive and invasive suppressor activity include, without limitation, those described in: Hortsch et al. J. Biol. Chem. 270(32):18809, 1995; Miyaki et al. Oncogene 11: 2547, 1995; Ozawa et al. Cell 63:1033, 1990.

A polynucleotide encoding a polypeptide comprising a CtLL sequence provided by the invention can be used for numerous diagnostic or other useful purposes. A polynucleotide of the invention (e.g., SEQ ID NO:1, 3, 5, 7, 9, 11, 13, or 15) can be used as markers for tissues in which the corresponding polypeptide is preferentially expressed, as molecular weight markers on Southern gels, as chromosome markers or tags to identify chromosomes or to map related gene positions, to compare with endogenous DNA sequences in subjects to identify potential genetic disorders, as probes to hybridize and thus discover novel related polynucleotides, as a source of information to derive PCR primers for genetic fingerprinting, as a probe to "subtract-out" known polynucleotides in the process of discovering other novel nucleic acids, as an antigen to raise anti-DNA antibodies or elicit another immune response, and for gene therapy.

Probes and Primers. Among the uses of the disclosed CtLL polynucleotides, and combinations of fragments thereof, is the use of fragments as probes or primers. Such fragments generally comprise at least about 17 contiguous nucleotides of a DNA sequence. In other embodiments, a DNA fragment comprises at least 30, or at least 60 contiguous nucleotides of a DNA sequence. The basic parameters affecting the choice of hybridization conditions and guidance for devising suitable conditions are set forth by Sambrook et al., 1989 and are described in detail above. Using knowledge of the genetic code in combination with the amino acid sequences set forth above, sets of degenerate oligonucleotides can be prepared. Such oligonucleotides are useful as primers, e.g., in polymerase chain reactions (PCR), whereby DNA fragments are isolated and amplified. In certain embodiments, degenerate primers can be used as probes for non-human genetic libraries. Such libraries would include but are not limited to cDNA libraries, genomic libraries, and even electronic EST (express sequence tag) or DNA libraries. Homologous sequences identified by this method would then be used as probes to identify non-human homologues of the CtLL sequence identified herein.

Chromosome Mapping. The polynucleotides encoding CtLL polypeptides, and the disclosed fragments and combinations of these polynucleotides, can be used by those skilled in the art using known techniques to identify the human chromosome to which these sequences map. Useful techniques include, but are not limited to, using the sequence or portions, including oligonucleotides, as a probe in various known techniques such as radiation hybrid mapping (high resolution), in situ hybridization to chromosome spreads (moderate resolution), and Southern blot hybridization to hybrid cell lines containing individual human chromosomes (low resolution). Information about radiation hybrid mapping can be found on the worldwideweb(www) at: genome.wi.m-it.edu/ftp/distribution/human_STS_releases/july97/07-97.INTRO.html.

A polynucleotide encoding a polypeptide comprising a CtLL sequence of the invention, and the disclosed fragments and combinations of these polynucleotides can be used to analyze abnormalities associated with the genes corresponding to CtLL polypeptides. This enables one to distinguish conditions in which this marker is rearranged or deleted. In addition, polynucleotides of the invention or a fragment thereof can be used as a positional marker to map other genes of unknown location. The polynucleotide can be used in developing treatments for any disorder mediated (directly or indirectly) by defective, or insufficient amounts of, genes corresponding to the polynucleotides of the invention. The polynucleotides and associated sequences disclosed herein permit the detection of defective genes, and the replacement thereof with normal genes. Defective genes can be detected in in vitro diagnostic assays, and by comparison of the polynucleotide sequences disclosed herein with that of a gene derived from a subject suspected of harboring a defect in this gene or having a CtLL-associated disorder.

Uses of CtLL polypeptides and peptide fragments thereof include, but are not limited to, the following: delivery agents; therapeutic and research reagents; molecular weight and isoelectric focusing markers; controls for peptide fragmentation; identification of unknown polypeptides; and preparation of antibodies.

The CtLL polypeptides (e.g., SEQ ID NO:2, 4, 6, 8, 10, 12, 14, and 16, and fragments, including solCtLL polypeptides thereof) of the invention can be used as purification reagents. For example, CtLL or solCtLL polypeptides can be attached to a solid support material and used to purify its binding partners by affinity chromatography. In particular embodiments, a polypeptide is attached to a solid support by conventional procedures. As one example, chromatography columns containing functional groups that will react with amino acid side chains of polypeptides are available (Pharmacia Biotech, Inc., Piscataway, N.J.). In an alternative embodiment, a solCtLL-Fc polypeptide is attached to Polypeptide A- or G-containing chromatography columns through interaction with the Fc moiety. The polypeptide also finds use in purifying or identifying cells that express a binding partner on the cell surface. Polypeptides are bound to a solid phase such as a column chromatography matrix or a similar suitable substrate. For example, magnetic microspheres can be coated with the polypeptides and held in an incubation vessel through a magnetic field. Suspensions of cell mixtures containing the binding partner expressing cells are contacted with the solid phase having the polypeptides thereon. Cells expressing the binding partner on the cell surface bind to the polypeptides on the solid phase, and unbound cells then are washed away. Alternatively, the polypeptides can be conjugated to a detectable moiety, then incubated with cells to be tested for binding partner expression. After incubation, unbound-labeled matter is removed and the presence or absence of the detectable moiety on the cells is determined.

Carriers and Delivery Agents. The polypeptides also find use as carriers for delivering agents attached thereto to cells or pathogens bearing identified binding partners. Thus, solCtLL polypeptides can be used to deliver diagnostic or therapeutic agents to such cells or pathogens in in vitro or in vivo procedures. Detectable (diagnostic) and therapeutic agents that can be attached to a CtLL or solCtLL polypeptide include, but are not limited to, toxins, cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating polypeptides, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu. Such agents can be attached to the polypeptide by any suitable conventional procedure. A CtLL or solCtLL polypeptide comprises functional groups on amino acid side chains that can be reacted with functional groups on a desired agent to form covalent bonds, for example. Alternatively, the polypeptide or agent can be derivatized to generate or attach a desired reactive functional group. The derivatization can involve attachment of one of the bifunctional coupling reagents available for attaching various molecules to polypeptides (Pierce Chemical Company, Rockford, Ill.). Of particular interest are soluble CtLL domains that can be used to target cells expressing a binding partner for a CtLL polypeptide. Such soluble CtLL polypeptides can be used to target reagents to cells or pathogens expressing, for example, a cognate to a CtLL polypeptide. Similarly, and as discussed more fully below, antibodies specific for a CtLL polypeptide can be labeled with a diagnostic or therapeutic agent and used to target the diagnostic or therapeutic to cells expressing a CtLL polypeptide.

CtLL polypeptides and fragments (e.g., solCtLL and fragments) can be employed in modulating a biological activity of a C-type lectin polypeptide, particularly CtLL polypeptide, in in vitro or in vivo procedures. Encompassed within the invention are domains of CtLL polypeptides that act as modulators of native CtLL polypeptide function when expressed as fragments or as components of fusion polypeptides. For example, a substantially purified polypeptide domain of the invention can be used to inhibit binding of a CtLL polypeptide to endogenous binding partners. Such use effectively would block CtLL interactions and inhibit CtLL activities. In still another aspect of the invention, a soluble form of a CtLL binding partner is used to bind to, and competitively inhibit activation of the endogenous CtLL polypeptide.

Antibodies that bind to CtLL polypeptides can inhibit CtLL polypeptide activity and may act as antagonists. For example, antibodies that specifically bind to one or more epitopes of a CtLL polypeptide, or epitope of conserved variants of CtLL polypeptides, or fragments can be used to inhibit CtLL activity. By "specifically bind" means that an antibody to a CtLL polypeptide or fragment thereof will not cross-react with unrelated polypeptides. Preferably such an antibody will not cross-react with other members of the C-type lectin family of proteins.

In an alternative aspect, the invention further encompasses the use of agonists of CtLL activity to treat or ameliorate the symptoms of a disease for which increased C-type lectin activity is beneficial. In a preferred aspect, the invention entails administering compositions comprising a CtLL polynucleotide (e.g., comprising SEQ ID NO:1, 3, 5, 7, 9, 11, 13, and/or 15) or fragment thereof or a polypeptide comprising a CtLL amino acid sequence (e.g., SEQ ID NO:2, 4, 6, 8, 10, 12, 14, and/or 16) or fragment thereof. The administering may be to cells in vitro, to cells ex vivo, to cells in vivo, and/or to a multicellular organism. One therapeutic form includes soluble forms of a CtLL polypeptide. Such a soluble CtLL polypeptide will bind to its binding partner (e.g., an oxidized lipid and/or a carbohydrate-containing moiety) and stimulate a biological activity associated with the binding partner.

In still another aspect of the invention, the compositions comprise administering a polynucleotide encoding a CtLL or a solCtLL polypeptide for expression in a host organism for treatment of disease. Particularly preferred in this regard is expression in a human subject for treatment of a dysfunction associated with aberrant (e.g., decreased or increased) endogenous activity of a CtLL polypeptide. Furthermore, the invention encompasses the administration of compounds found to increase the endogenous activity of polypeptides comprising a CtLL amino acid sequence to cells and/or organisms. One example of compounds that increase CtLL polypeptide activity are antibodies, preferably monoclonal antibodies, that bind to CtLL polypeptides and increase or stimulate CtLL polypeptide activity by causing constitutive intracellular signaling (or "ligand mimicking"), or by preventing the binding of a native inhibitor of CtLL polypeptide activity.

Due to the multiplicity and interconnectedness of biological pathways and interactions, a CtLL polypeptide, solCtLL polypeptide, fragments of the foregoing, variant, antagonist, agonist, antibody, and binding partner of the invention can be useful for treating medical conditions and diseases associated with cell-cell, cell-pathogen interactions, atherosclerosis, coronary diseases and disorders, cell proliferative diseases and disorders, and inflammatory disease and disorder as described further herein. The therapeutic molecule or molecules to be used will depend on the etiology of the condition to be treated and the biological pathways involved, and will consider that different variants, antagonists, and binding partners of CtLL polypeptides may have similar or different effects. Accordingly, a CtLL agonist or antagonist may modulate immune cell activity and inflammation, such as release of growth factors, adhesion proteins, and inflammatory factors.

The disclosed CtLL polypeptides, solCtLL polypeptides, fragments thereof, antibodies, compositions and combination therapies described herein are useful in medicines for treating bacterial, viral or protozoal infections, and complications resulting therefrom. Cardiovascular disorders are treatable with the disclosed CtLL polypeptides, solCtLL polypeptides, fragments thereof, antibodies, compositions and combination therapies, including aortic aneurysms; arteritis; vascular occlusion; complications of coronary by-pass surgery; ischemia/reperfusion injury; heart disease; heart failure; and myocardial infarction. In addition, the CtLL polypeptides, solCtLL polypeptides, fragments thereof, antibodies, compositions and combination therapies of the invention can be used to treat chronic pain conditions, to treat various disorders of the endocrine system, conditions of the gastrointestinal system, disorders of the genitourinary system, and anemias and hematological disorders.

In addition, the polypeptides, fragments thereof, antibodies, compositions, and combination therapies of the invention have application to cell proliferative disorders, including cancer and cancer cell metastasis. Also provided herein are methods for using CtLL polypeptides, solCtLL polypeptides, fragments thereof, antibodies, compositions and combination therapies to treat various hematologic and oncologic disorders. For example, soluble CtLL domains can be used to treat various forms of cancer, including acute myelogenous leukemia, Epstein-Barr virus-positive nasopharyngeal carcinoma, glioma, colon, stomach, prostate, renal cell, cervical and ovarian cancers, lung cancer (SCLC and NSCLC), including cancer-associated cachexia, fatigue, asthenia, paraneoplastic syndrome of cachexia, and hypercalcemia by modulating lectin-associated interactions.

Additional diseases treatable with the polypeptides, fragments, antibodies, compositions or combination therapies of the invention are solid tumors, including sarcoma, osteosarcoma, and carcinoma, such as adenocarcinoma (e.g., breast cancer) and squamous cell carcinoma. Administration of a solCtLL domain can modulate cell-cell and cell-matrix interactions of such tumor cells and/or modulate the angiogenesis and blood supply to such tumors.

In addition, the CtLL polypeptides, solCtLL polypeptides, fragments thereof, antibodies, compositions and combination therapies are useful for treating leukemia, including acute myelogenous leukemia, chronic or acute lymphoblastic leukemia and hairy cell leukemia. Other malignancies with invasive metastatic potential that can be treated with the CtLL polypeptides, solCtLL polypeptides, fragments thereof, antibodies, compositions and combination therapies, include multiple myeloma, various lymphoproliferative disorders such as autoimmune lymphoproliferative syndrome (ALPS), chronic lymphoblastic leukemia, hairy cell leukemia, chronic lymphatic leukemia, peripheral T-cell lymphoma, small lymphocytic lymphoma, mantle cell lymphoma, follicular lymphoma, Burkitt's lymphoma, Epstein-Barr virus-positive T cell lymphoma, histiocytic lymphoma, Hodgkin's disease, diffuse aggressive lymphoma, acute lymphatic leukemias, T gamma lymphoproliferative disease, cutaneous B cell lymphoma, cutaneous T cell lymphoma (i.e., mycosis fungoides), and Sezary syndrome.

A combination of at least one CtLL polypeptide, solCtLL polypeptides, fragment thereof, or antibody, and one or more anti-angiogenesis factors or other therapeutic agent(s) may be administered to the subject. The additional therapeutic agent(s) may be administered prior to, concurrently with, or following the administration of the CtLL polypeptide, solCtLL polypeptides, fragment thereof, or antibody. The use of more than one therapeutic agent is particularly advantageous when the subject that is being treated has a solid tumor. In some embodiments of the invention, the treatment further comprises treating the mammal with radiation. Radiation, including brachytherapy and teletherapy, may be administered prior to, concurrently with, or following the administration of the CtLL polypeptide, solCtLL polypeptides, fragment, antibody, or CtLL binding partner and/or additional therapeutic agent(s).

In some embodiments the method includes the administration of, in addition to CtLL polypeptide, solCtLL polypeptides, fragment thereof, or antibody, one or more therapeutics selected from the group consisting of alkylating agents, antimetabolites, vinca alkaloids and other plant-derived chemotherapeutics, antitumor antibiotics, antitumor enzymes, topoisomerase inhibitors, platinum analogs, adrenocortical suppressants, hormones and antihormones, antibodies, immunotherapeutics, radiotherapeutics, and biological response modifiers.

In some embodiments the method includes administration of, in addition to a CtLL polypeptide, solCtLL polypeptides, fragment thereof, or antibody, one or more therapeutics selected from the group consisting of cisplatin, cyclophosphamide, mechloretamine, melphalan, bleomycin, carboplatin, fluorouracil, 5-fluorodeoxyuridine, methotrexate, taxol, asparaginase, vincristine, and vinblastine, lymphokines and cytokines such as interleukins, interferons ($\alpha$, $\beta$ or $\delta$) and TNF, chlorambucil, busulfan, carmustine, lomustine, semustine, streptozocin, dacarbazine, cytarabine, mercaptopurine, thioguanine, vindesine, etoposide, teniposide, dactinomycin, daunorubicin, doxorubicin, bleomycin, plicamycin, mitomycin, L-asparaginase, hydroxyurea, methylhydrazine, mitotane, tamoxifen, fluoxymesterone, IL-8 inhibitors, angiostatin, endostatin, kringle 5, angiopoietin-2 or other antagonists of angiopoietin-1, antagonists of platelet-activating factor, antagonists of basic fibroblast growth factor, and COX-2 inhibitors.

In some embodiments the method includes administration of, in addition to a CtLL polypeptide, solCtLL polypeptides, fragment thereof, or antibody, one or more therapeutic polypeptides, including soluble forms thereof, selected from the group consisting of Flt3 ligand (see, U.S. Pat. No. 5,554,512), CD40 ligand (see, U.S. Pat. No. 5,716,805), IL-2, IL-12, 4-1BB ligand (see, U.S. Pat. No. 5,674,704), anti-4-1BB antibodies, TRAIL, TNF antagonists and TNF receptor antagonists including TNFR/Fc, Tek antagonists, TWEAK antagonists and TWEAK-R (see, U.S. Ser. Nos. 60/172,878 and 60/203,347 and Feng et al., Am. J. Pathol. 156(4):1253) antagonists including TWEAK-R/Fc, VEGF antagonists including anti-VEGF antibodies, VEGF receptor (including VEGF-R1 and VEGF-R2, also known as Flt1 and Flk1 or KDR) antagonists, CD148 (also referred to as DEP-1, ECRTP, and PTPRJ, see Takahashi et al., J. Am. Soc. Nephrol. 10:2135-45, 1999; and PCT Publication No. WO 00/15258, 23 Mar. 2000) binding proteins, and nectin-3 (see, Satoh-Horikawa et al., J. Biol. Chem. 275(14):10291, 2000; GenBank accession numbers of human nectin-3 nucleic acid and polypeptide sequences are AF282874 and AAF97597, respectively) antagonists.

In some preferred embodiments a CtLL polypeptide, solCtLL polypeptides, fragment thereof, or antibody of the invention is used as a component of, or in combination with, "metronomic therapy," such as that described by Browder et al. and Klement et al. (Cancer Research 60:1878, 2000; J. Clin. Invest. 105(8):R15, 2000; see also Baringa, Science 288:245, 2000).

This invention provides compounds, compositions, and methods for treating a subject, preferably a mammalian subject, and most preferably a human subject, who is suffering from a CtLL-associated disorder. Such CtLL-associated disorders include conditions caused (directly or indirectly) or exacerbated by binding between a polypeptide having an CtLL sequence (e.g., SEQ ID NO:2, 4, 6, 8, 10, 12, 14, or 16)

and its binding partner (e.g., an oxidized lipid and/or a carbohydrate moiety). For purposes of this disclosure, the terms "illness," "disease," "disorder," "medical condition," "abnormal condition" and the like are used interchangeably with the term "medical disorder." The terms "treat", "treating", and "treatment" used herein include curative, preventative (e.g., prophylactic) and palliative or ameliorative treatment. For such therapeutic uses, CtLL polypeptides and fragments (including solCtLL and fragments thereof), CtLL polynucleotides encoding a CtLL polypeptide or fragment, and/or agonists or antagonists of the CtLL polypeptide such as antibodies or solCtLL can be administered to the subject in need through known means. Compositions of the invention can contain a polypeptide in any form described herein, such as native polypeptides, variants, derivatives, oligomers, and biologically active fragments. In particular embodiments, the composition comprises a soluble polypeptide or an oligomer comprising soluble CtLL (solCtLL) polypeptides.

In practicing the method of treatment or use of the invention, a therapeutically effective amount of a therapeutic agent of the invention is administered to a subject having a condition to be treated, preferably to treat or ameliorate diseases associated with the activity of a CtLL polypeptide. "Therapeutic agent" includes without limitation any CtLL polypeptide, solCtLL polypeptides, fragment, and variant; polynucleotide encoding a CtLL polypeptide, solCtLL polypeptide, fragment, and variant; agonists or antagonists of the a CtLL polypeptide such as antibodies; a CtLL polypeptide binding partner; complexes formed from a CtLL polypeptide, solCtLL polypeptide, fragment, variant, and binding partner, and the like. As used herein, the term "therapeutically effective amount" means the total amount of each therapeutic agent or other active component of the pharmaceutical composition or method that is sufficient to show a meaningful subject benefit, e.g., treatment, healing, prevention or amelioration of the relevant medical condition, or an increase in rate of treatment, healing, prevention or amelioration of such conditions. When applied to an individual therapeutic agent or active ingredient, administered alone, the term refers to that ingredient alone. When applied to a combination, the term refers to combined amounts of the ingredients that result in the therapeutic effect, whether administered in combination, serially or simultaneously. As used herein, the phrase "administering a therapeutically effective amount" of a therapeutic agent means that the subject is treated with said therapeutic agent in an amount and for a time sufficient to induce an improvement, and preferably a sustained improvement, in at least one indicator that reflects the severity of the disorder. An improvement is considered "sustained" if the subject exhibits the improvement on at least two occasions separated by one or more weeks. The degree of improvement is determined based on signs or symptoms, and determinations may also employ questionnaires that are administered to the subject, such as quality-of-life questionnaires. Various indicators that reflect the extent of the subject's illness may be assessed for determining whether the amount and time of the treatment is sufficient. The baseline value for the chosen indicator or indicators is established by examination of the subject prior to administration of the first dose of the therapeutic agent. Preferably, the baseline examination is done within about 60 days of administering the first dose. If the therapeutic agent is being administered to treat acute symptoms, the first dose is administered as soon as practically possible after the injury has occurred. Improvement is induced by administering therapeutic agents such as a CtLL polypeptide, solCtLL polypeptide, fragment, antibody, or CtLL binding partner until the subject manifests an improvement over baseline for the chosen indicator or indicators. In treating chronic conditions, this degree of improvement is obtained by repeatedly administering this medicament over a period of at least a month or more, e.g., for one, two, or three months or longer, or indefinitely. A period of one to six weeks, or even a single dose, often is sufficient for treating acute conditions. Although the extent of the subject's illness after treatment may appear improved according to one or more indicators, treatment may be continued indefinitely at the same level or at a reduced dose or frequency. Once treatment has been reduced or discontinued, it later may be resumed at the original level if symptoms should reappear.

One skilled in the art will recognize that suitable dosages will vary, depending upon such factors as the nature and severity of the disorder to be treated, the subject's body weight, age, general condition, and prior illnesses and/or treatments, and the route of administration. Preliminary doses can be determined according to animal tests, and the scaling of dosages for human administration is performed according to art-accepted practices such as standard dosing trials. For example, the therapeutically effective dose can be estimated initially from cell culture assays. The dosage will depend on the specific activity of the compound and can be readily determined by routine experimentation. A dose may be formulated in animal models to achieve a circulating plasma concentration range that includes the $IC_{50}$ (i.e., the concentration of the test compound which achieves a half-maximal inhibition of symptoms) as determined in cell culture, while minimizing tonicities. Such information can be used to more accurately determine useful doses in humans. Ultimately, the attending physician will decide the amount of polypeptide of the invention with which to treat each individual subject. Initially, the attending physician will administer low doses of polypeptide of the invention and observe the subject's response. Larger doses of polypeptide of the invention may be administered until the optimal therapeutic effect is obtained for the subject, and at that point the dosage is not increased further. It is contemplated that the various pharmaceutical compositions used to practice the method of the invention should contain about 0.01 ng to about 100 mg (preferably about 0.1 ng to about 10 mg, more preferably about 0.1 microgram to about 1 mg) of a polypeptide of the invention per kg body weight. In one embodiment of the invention, a CtLL polypeptide, solCtLL polypeptide, fragment, antibody, or CtLL binding partner is administered one time per week to treat the various medical disorders disclosed herein. In another embodiment polypeptide, fragment, antibody, or CtLL binding partner is administered at least two times per week and in another embodiment at least three times per week. If injected, the effective amount of a CtLL polypeptide, solCtLL polypeptide, fragment, antibody, or CtLL binding partner per adult dose ranges from 1-20 $mg/m^2$, and preferably is about 5-12 $mg/m^2$. Alternatively, a flat dose may be administered whose amount may range from 5-100 mg/dose. Exemplary dose ranges for a flat dose to be administered by subcutaneous injection are 5-25 mg/dose, 25-50 mg/dose and 50-100 mg/dose. In one embodiment of the invention, the various indications described herein are treated by administering a preparation acceptable for injection containing a CtLL polypeptide, solCtLL polypeptide, fragment, antibody, or CtLL binding partner at 25 mg/dose, or alternatively, containing 50 mg per dose. The 25 mg or 50 mg dose may be administered repeatedly, particularly for chronic conditions. If a route of administration other than injection is used, the dose is appropriately adjusted in accord with standard medical practices.

In many instances, an improvement in a subject's condition will be obtained by injecting a dose of about 25 mg of a CtLL polypeptide, solCtLL polypeptide, fragment, antibody, or CtLL binding partner one to three times per week over a period of at least three weeks, or a dose of 50 mg of a CtLL polypeptide, fragment, antibody, or CtLL binding partner one or two times per week for at least three weeks (a treatment for longer periods may be necessary to induce the desired degree of improvement). For incurable chronic conditions, the regimen may be continued indefinitely, with adjustments being made to dose and frequency if such are deemed necessary by the subject's physician. The foregoing doses are examples for an adult subject who is a person who is 18 years of age or older. For pediatric subjects (age 4-17), a suitable regimen involves the subcutaneous injection of 0.4 mg/kg, up to a maximum dose of 25 mg of a CtLL polypeptide, solCtLL polypeptide, fragment, antibody, or CtLL binding partner, administered by subcutaneous injection one or more times per week. If an antibody against a CtLL polypeptide is used as a CtLL polypeptide antagonist, a preferred dose range is 0.1 to 20 mg/kg, and more preferably is 1-10 mg/kg. Another preferred dose range for an anti-CtLL polypeptide antibody is 0.75 to 7.5 mg/kg of body weight. Humanized antibodies are preferred. Such antibodies may be injected or administered intravenously.

Compositions comprising an effective amount of a CtLL polypeptides, solCtLL polypeptides, fragments thereof, and antibodies of the invention (from whatever source derived, including without limitation from recombinant and non-recombinant sources), in combination with other components such as a physiologically acceptable diluent, carrier, or excipient, are provided herein. The term "pharmaceutically acceptable" means a non-toxic material that does not interfere with the effectiveness of the biological activity of the active ingredient(s). Formulations suitable for administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa. In some embodiments the polypeptide may undergo pegylation to assist in adsorption or uptake. For example, such compositions can be complexed with polyethylene glycol (PEG), metal ions, or incorporated into polymeric compounds such as polyacetic acid, polyglycolic acid, hydrogels, dextran, and the like, or incorporated into liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference. Such compositions will influence the physical state, solubility, stability, rate of in vivo release, and rate of in vivo clearance, and are thus chosen according to the intended application, so that the characteristics of the carrier will depend on the selected route of administration. In one preferred embodiment of the invention, sustained-release forms of a CtLL polypeptides, solCtLL polypeptides, fragments thereof, and/or antibodies are used. Examples of sustained-release forms suitable for use in the disclosed methods include, but are not limited to, a CtLL polypeptide that is encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

A CtLL polypeptide or solCtLL polypeptide of the invention may be active in multimers (e.g., heterodimers or homodimers) or complexes with itself or other polypeptides. As a result, pharmaceutical compositions of the invention may comprise a polypeptide of the invention in such multimeric or complexed form. The pharmaceutical composition of the invention may be in the form of a complex of the polypeptide(s) of invention. The invention further includes the administration of a CtLL polypeptide, solCtLL polypeptide, fragment, antibody, or CtLL binding partner concurrently with one or more other drugs that are administered to the same subject in combination, each drug being administered according to a regimen suitable for that medicament. "Concurrent administration" encompasses simultaneous or sequential treatment with the components of the combination, as well as regimens in which the drugs are alternated, or wherein one component is administered long-term and the other(s) are administered intermittently. Components may be administered in the same or in separate compositions, and by the same or different routes of administration. Examples of components that may be included in the pharmaceutical composition of the invention are cytokines, lymphokines, or other hematopoietic factors such as: M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, IL-17, IL-18, IFN, TNF0, TNF1, TNF2, G-CSF, Meg-CSF, thrombopoietin, stem cell factor, and erythropoietin. The pharmaceutical composition may further contain other agents that either enhance the activity of the polypeptide or compliment its activity or use in treatment. Such additional factors and/or agents may be included in the pharmaceutical composition to produce a synergistic effect with a polypeptide of the invention, or to minimize side effects. Conversely, a CtLL polypeptide, a solCtLL polypeptide, fragment, antibody, or CtLL binding partner of the invention may be included in formulations with a particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. Additional examples of drugs to be administered concurrently include but are not limited to antivirals, antibiotics, analgesics, corticosteroids, antagonists of inflammatory cytokines, non-steroidal anti-inflammatories, pentoxifylline, thalidomide, and disease-modifying anti-rheumatic drugs (DMARDs) such as azathioprine, cyclophosphamide, cyclosporine, hydroxychloroquine sulfate, methotrexate, leflunomide, minocycline, penicillamine, sulfasalazine and gold compounds such as oral gold, gold sodium thiomalate, and aurothioglucose. Additionally, a CtLL polypeptide, a solCtLL polypeptide, fragment, antibody, or CtLL binding partner may be combined with a second CtLL polypeptide, solCtLL polypeptide, antibody against a CtLL polypeptide, or a CtLL polypeptide-derived peptide that acts as a competitive inhibitor of a native a CtLL polypeptide.

Any efficacious route of administration may be used to therapeutically administer a CtLL polypeptide, a solCtLL polypeptide, fragment, antibody, or CtLL binding partner thereof, including those compositions comprising CtLL polynucleotides. Parenteral administration includes injection, for example, via intra-articular, intravenous, intramuscular, intralesional, intraperitoneal or subcutaneous routes by bolus injection or by continuous infusion. Other routes include localized administration, e.g., at a site of disease or injury. Other suitable means of administration include sustained release from implants; aerosol inhalation and/or insufflation; eyedrops; vaginal or rectal suppositories; buccal preparations; oral preparations, including pills, syrups, lozenges or chewing gum; and topical preparations such as lotions, gels, sprays, ointments or other suitable techniques. Alternatively, a CtLL polypeptide, a solCtLL polypeptide, fragment, antibody, or CtLL binding partner may be delivered by implanting cells that express the polypeptide, for example, by implanting cells that express a CtLL polypeptide, a solCtLL polypeptide, fragment, antibody, or CtLL binding partner. Cells may also be cultured ex vivo in the presence of polypeptides of the invention in order to proliferate or to produce a desired effect on or activity in such cells. Treated cells can then be introduced in vivo for therapeutic purposes. In another embodiment, the subject's own cells are induced to produce a CtLL polypeptide, a solCtLL polypeptide, fragment, antibody, or CtLL binding partner by transfection in vivo or ex vivo with a polynucleotide that encodes a CtLL polypeptide, a solCtLL polypeptide, fragment, antibody, or CtLL binding partner. The polynucleotide can be introduced into the subject's cells, for example, by injecting naked DNA or liposome-encapsulated DNA that encodes a CtLL polypeptide, a solCtLL polypeptide, fragments thereof, antibody, or CtLL binding partner, or by other means of transfection. Polynucleotides of the invention may also be administered to subjects by other known methods for introduction of nucleic acids into a cell or organism (including, without limitation, in the form of viral vectors).

When a therapeutically effective amount of a CtLL polypeptide, solCtLL polypeptide, fragments thereof, antibody, or binding partner of the invention is administered orally, the polypeptide will typically be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% a polypeptide of the invention, and preferably from about 25 to 90% a polypeptide of the invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of a polypeptide of the invention, and preferably from about 1 to 50% a polypeptide of the invention.

When a therapeutically effective amount of a CtLL polypeptide, solCtLL polypeptide, fragments thereof, antibody, or binding agent of the invention is administered by intravenous, cutaneous or subcutaneous injection, the polypeptide will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition for intravenous, cutaneous, or subcutaneous injection should contain, in addition to a polypeptide of the invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the invention may also contain stabilizers, preservatives, buffers, antioxidants, or other additives known to those of skill in the art. The duration of intravenous therapy using the pharmaceutical composition of the invention will vary, depending on the severity of the disease being treated and the condition and potential idiosyncratic response of each individual subject. It is contemplated that the duration of each application of a polypeptide of the invention will be in the range of 12 to 24 hours of continuous intravenous administration. Ultimately the attending physician will decide on the appropriate duration of intravenous therapy.

For compositions of the invention which are useful for tissue repair or regeneration, the therapeutic method includes administering a pyrogen-free, physiologically acceptable form of the composition topically, systematically, locally or in association with an implant or device. Further, the composition may desirably be encapsulated or injected in a viscous form for delivery to the site tissue damage. Additional useful agents may also optionally be included in the composition, as described above, or may be administered simultaneously or sequentially with the composition in the methods of the invention. The compositions can include a matrix capable of delivering the polypeptide-containing composition to the site tissue damage, providing a structure for the developing tissue and optimally capable of being resorbed into the body. The choice of matrix material is based on biocompatibility, biodegradability, mechanical properties, cosmetic appearance and interface properties. Potential matrices for the compositions include calcium sulfate, tricalciumphosphate, hydroxyapatite, polylactic acid, polyglycolic acid and polyanhydrides. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. Progress can be monitored by periodic assessment of tissue/bone growth and/or repair, for example, X-rays, histomorphometric determinations and tetracycline labeling.

In addition to human subjects, compositions comprising a CtLL polypeptide, solCtLL polypeptide, fragments thereof, antibody, or CtLL binding partner is useful in the treatment of disease conditions in non-human animals, such as pets (dogs, cats, birds, primates, and the like), domestic farm animals (horses cattle, sheep, pigs, birds, and the like). In such instances, an appropriate dose may be determined according to the animal's body weight. For example, a dose of 0.2-1 mg/kg may be used. Alternatively, the dose is determined according to the animal's surface area, an exemplary dose ranging from 0.1-20 mg/m$^2$, or more preferably, from 5-12 mg/m$^2$. For small animals, such as dogs or cats, a suitable dose is 0.4 mg/kg. In a one embodiment, a CtLL polypeptide, solCtLL polypeptide, fragments thereof, antibody, or CtLL binding partner (preferably constructed from genes derived from the same species as the subject), is administered by injection or other suitable route one or more times per week until the animal's condition is improved, or it may be administered indefinitely.

The invention also relates to the use of a CtLL polypeptide, a solCtLL polypeptide, fragments thereof, and variants; polynucleotide encoding a CtLL polypeptide, a solCtLL polypeptide, fragments thereof, and variants; agonists or antagonists of a CtLL polypeptide such as antibodies or solCtLL polypeptides; a CtLL polypeptide binding partner; complexes formed from a CtLL polypeptide, a solCtLL polypeptide, fragments thereof, variant, and binding partner, and the like, in the manufacture of a medicament for the prevention or therapeutic treatment of a disease or disorder.

Further encompassed by the invention are systems and methods for analyzing CtLL polypeptides comprising identifying and/or characterizing one or more CtLL polypeptides, polynucleotides encoding CtLL polypeptides, and corresponding genes, these systems and methods preferably comprising a data set representing a set of one or more CtLL molecules. Accordingly, the invention provides a computer readable medium having stored thereon a member selected from the group consisting of a polynucleotide comprising a sequence as set forth in SEQ ID NO:1, 3, 5, 7, 9, 11, 13, and/or 15; or a polypeptide comprising a sequence as set forth in SEQ ID NO:2, 4, 6, 8, 10, 12, 14, and/or 16.

One embodiment of the invention comprises a computing environment and a plurality of algorithms selectively executed to analyze a polypeptide or polynucleotide of the invention. Examples of analyses of an CtLL polypeptide include, without limitation, displaying the amino acid sequence of a polypeptide in the set, comparing the amino acid sequence of one polypeptide in the set to the amino acid sequence of another polypeptide in the set, predicting the structure of a polypeptide in the set, determining the nucleotide sequences of nucleic acids encoding a polypeptide in the set, and identifying a gene corresponding to a polypeptide in the set.

Unless otherwise defined, all technical and scientific terms used herein have the same meaning as commonly understood by one of ordinary skill in the art to which this invention belongs. All headings and subheading provided herein are solely for ease of reading and should not be construed to limit the invention. The terms "a", "an" and "the" as used herein are meant to encompass the plural unless the context clearly dictates the singular form. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. The following examples are intended to illustrate particular embodiments and not to limit the scope of the invention.

EXAMPLES

Example 1

Identification of CtLL, a New Member of the C-type Lectin Family of Polypeptides A data set was received from Celera Genomics (Rockville, Md.) containing amino acid sequences predicted to be encoded by the human genome. This data set was threaded through a folding algorithm based upon the work of Adam Godzik and Jeff Skolnick's "GeneFold" (distributed by Tripos) protein to identify helical cytokine family polypeptides. An amino acid sequence as set forth in SEQ ID NO:2 from amino acid 22 to 116 was identified in the search. A subsequent BLAST search using the foregoing sequence revealed a mouse cDNA (GenBank accession no. AK16908, later renamed as XP_132881, which is incorporated herein by reference) predicted to encode a 275 amino acid protein. The BLAST search also identified C-type lectin molecules. Alternative murine splice variants of the minus exon 4 type were also identified which would generate molecules without the C lectin domain but with new transmembrane spanning regions.

By PCR a human C-type lectin molecule and additional splice variants were identified, and these are presented in FIG. 1. The amino acid sequences presented in FIG. 1 are presented in standard 1-letter amino acid code, where "A" represents alanine, "C" represents cysteine, and the like.

Example 2

CtLL Polypeptide and Polynucleotide Analysis

Analysis of the polypeptide sequences of SEQ ID Nos:2, 4, 6, 8, 10, 12, 14, and 16 indicated classic membrane anchor(s) and a type-2 topology. An alignment and computer algorithm analysis of SEQ ID Nos:2, 4, 6, 8, 10, 12, 14, and 16 indicates a transmembrane domain includes about amino acids 42 to 65 of SEQ ID Nos:2, 4, 6, 8, 10, 12, 14, and 16; includes about amino acids 137 to 159 of SEQ ID Nos:2, 8, 14, and 16; and includes about amino acids 164 to 182 of SEQ ID NO:2. In addition, soluble CtLL polypeptides ("solCtLL") of the present invention comprise amino acids: from about residue 1 to about 41 of SEQ ID NO:2, 4, 6, 8, 10, 12, 14, or 16; from about residue 66 to about 136 of SEQ ID NO:2, 8, 14, and 16; from about residue $x_1$ to about $x_2$ of SEQ ID NO:4, wherein $x_1$ is a residue between and including residues 66 and 143 and $x_2$ is a residue between and including residue 226 and 233 (e.g., 226, 227, 228, 229, etc.); from about residue $x_1$ to about $x_2$ of SEQ ID NO:6, wherein $x_1$ is a residue between and including residues 66 and 143 and $x_2$ is a residue between and including residue 227 and 232 (e.g., 227, 228, 229, 230, etc.); from about residue $x_1$ to about 247 of SEQ ID NO:10, wherein $x_1$ is a residue between and including about residues 66 and 142; and/or from about residue $x_1$ to about 276 of SEQ ID NO:12, wherein $x_1$ is a residue between and including residues 66 and 142. A putative lectin domain was identified in the polypeptides of the invention as comprising an amino acid sequence as set forth from about 143 to 226 of SEQ ID NO:4; from about 143 to 227 of SEQ ID NO:6; from about 142 to 247 of SEQ ID NO:10; and from about 142 to 276 of SEQ ID NO:12. Furthermore a number of putative glycosylation sites were identified and include N91 and N101 of SEQ ID Nos:2, 4, 6, 8, 10, 12, 14, and 16.

The polynucleotide sequences encoding the CtLL polypeptides of SEQ ID Nos:2, 4, 6, 8, 10, 12, 14, and 16 are provided. An analysis of the coding sequence of SEQ ID NO:1, 3, 5, 7, 9, 11, 13, or 15, demonstrates that the domain having ligand binding activity correspond, for example, to a sequence from about nucleotide 427 to 678 of SEQ ID NO:3, from about 463 to 717 of SEQ ID NO:5, from about 524 to 841 of SEQ ID NO:9, and from about 475 to 876 of SEQ ID NO:11. Accordingly, a polynucleotide comprising the foregoing sequence above represent a coding sequence for a soluble CtLL polypeptide having oxidized lipid and/or carbohydrate binding activity.

Variants of the CtLL polypeptide sequences can be identified based upon the sequences provided herein. Amino acid substitutions and other alterations (deletions, insertions, and the like) to CtLL amino acid sequences are predicted to be more likely to alter or disrupt CtLL polypeptide activities if they result in changes to the conserved residues of the amino acid sequences as shown in FIG. 1, and particularly if those changes do not substitute an amino acid of similar structure (such as substitution of any one of the aliphatic residues—Ala, Gly, Leu, Ile, or Val—for another aliphatic residue). Conversely, if a change is made to a CtLL amino acid sequence resulting in substitution of the residue at that position in the alignment from one of the other CtLL polypeptide sequences, it is less likely that such an alteration will affect the function of the altered CtLL polypeptide.

Example 3

Monoclonal Antibodies that Bind Polypeptides of the Invention

A substantially purified CtLL polypeptide or solCtLL polypeptide can be used to generate monoclonal antibodies immunoreactive therewith, using conventional techniques such as those described in U.S. Pat. No. 4,411,993. Mice are immunized with a CtLL polypeptide immunogen emulsified in complete Freund's adjuvant, and injected in amounts ranging from 10-100 µg subcutaneously or intraperitoneally. Ten to twelve days later, the immunized animals are boosted with additional CtLL polypeptide emulsified in incomplete Freund's adjuvant. Mice are periodically boosted thereafter on a weekly to bi-weekly immunization schedule. Serum samples are periodically taken by retro-orbital bleeding or tail-tip excision to test for a CtLL polypeptide antibody by dot blot assay, ELISA (Enzyme-Linked Immunosorbent Assay) or inhibition of binding of a CtLL polypeptide to a CtLL polypeptide binding partner.

Following detection of an appropriate antibody titer, positive animals are provided one last intravenous injection of a CtLL polypeptide in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against a substantially pure CtLL polypeptide by adaptations of the techniques disclosed in Engvall et al., (*Immunochem.* 8:871, 1971) and in U.S. Pat. No. 4,703,004. A preferred screening technique is the antibody capture technique described in Beckmann et al., (*J. Immunol.* 144:4212, 1990). Positive hybridoma cells can be injected intraperitoneally into syngeneic BALB/c mice to produce ascites containing high concentrations of anti-CtLL monoclonal antibody. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Polypeptide A or Polypeptide G can also be used, as can chromatography based upon binding to CtLL polypeptide.

Example 4

Chromosome Mapping

The gene corresponding to a CtLL polypeptide is mapped using PCR-based mapping strategies. Initial human chromosomal assignments are made using CtLL-specific PCR primers and a BIOS Somatic Cell Hybrid PCRable DNA kit from BIOS Laboratories (New Haven, Conn.), following the manufacturer's instructions. More detailed mapping is performed using a Genebridge 4 Radiation Hybrid Panel (Research Genetics, Huntsville, Ala. (see, e.g., Walter, M A et al., Nature Genetics 7:22-28, 1994). Data from this analysis is then submitted electronically to the MIT Radiation Hybrid Mapper www-genome.wi.mit.edu/cgi-bin/contig/rhmapper.pl) following the instructions contained therein. This analysis yields specific genetic marker names which, when submitted electronically to NCBI: ncbi.nlm.nih.gov/genemap/map.cgi?CHR=19) yield the specific chromosome interval. The chromosomal location of the CtLL is on chromosome 19. The CtLL sequences lie closest in the genome to CLEC2 (a family member expressed in liver) and between CLEC2 and CLEC1 (a family member expressed in dendritic cells and endothelial cells in a sub-cluster of molecules expressed in macrophages, DCs and endothelial cells including OLR1, which is expressed in macrophages and induced in endothelial cells and vascular smooth muscle cells. The order beginning from the end of the short arm of chromosome 19 and transcription orientation (→←) as well as ITIM presence are as follows:

Macrophage antigen←MacrophageAg-2(AAW40215)(ITIM)CLEC2(ITIM)→←CtLL(ITIM)CLEC1→dectin1(ITAM)→OLR1→

Example 5

Hybridization Probes

Hybridization probes derived from SEQ ID NO:1, 3, 5, 7, 9, 11, 13, or 15 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using OLIGO, labeled by combining 50 pmol of each oligomer and 250 mCi of $\gamma$-$^{32}$P-adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1.×SSC and 0.5% SDS. Radiographic film is exposed to the blots and hybridization patterns are compared visually.

Example 6

Expression of CtLL Ligand Binding Domain

Expression of the solCtLL ligand binding domain is accomplished by subcloning a corresponding polynucleotide coding sequence (e.g., a sequence from about nucleotide 427 to 678 of SEQ ID NO:3, from about 463 to 717 of SEQ ID NO:5, from about 524 to 841 of SEQ ID NO:9, or from about 475 to 876 of SEQ ID NO:11) into appropriate expression vector and transfecting the vectors into suitable host cells.

Lectin activity of CtLL or biologically active fragments thereof may be assayed by first labeling the CtLL protein or polypeptide with $^{125}$I Bolton-Hunter reagent (Bolton and Hunter, Biochem J 133:529, 1973). Candidate ligands (including polysaccharides, glycoproteins or whole cells) previously arrayed in the wells of a 96 well plate are incubated with the labeled CtLL, washed and any wells with labeled CtLL complex are assayed. Data obtained using different concentrations of CtLL are used to calculate values for the number, affinity, and association of CtLL with the candidate ligands.

Example 7

Analysis of Murine CtLL Polypeptide Expression by Real-Time Quantitative PCR Expression of the full length murine analog of full length CtLL (sequence available in Genebank Accession number XP_132881) was analyzed in normal adult mice as well as in an asthma mouse model.

For the following experiments, RNA samples were obtained from a variety of murine tissues, or from cells or tissues treated with a variety of compounds. The RNA samples were DNase treated (product #1906, Ambion, Austin, Tex.), and reverse transcribed into a population of cDNA molecules using TaqMan Reverse Transcription Reagents (product #N808-0234, Applied Biosystems, Foster City, Calif.) according to the manufacturer's instructions using random hexamers. Each population of cDNA molecules was placed into specific wells of a multi-well plate at either 5 ng or 20 ng per well and run in triplicate. Pooling was used when same tissue types and stimulation conditions were applied but collected from different donors. Negative control wells were included in each multi-well plate of samples.

Sets of probes and oligonucleotide primers complementary to mRNAs encoding the murine analog of full length CtLL polypeptide were designed using Primer Express software (Applied Biosystems, Foster City, Calif.) and synthesized, and PCR conditions for these probe/primer sets were optimized to produce a steady and logarithmic increase in PCR product every thermal cycle between approximately cycle 20 and cycle 36. The forward murine CtLL polypeptide primer used was 5' GGG AAT CGG GAT GGA AAT AAC 3' (SEQ ID NO:29); the reverse murine CtLL primer used was 5' GCG CCT CGC CAA AGT G 3' (SEQ ID NO:30); and the labeled probe used for CtLL polypeptide was 5' AAG AAG GAC ACC CAG CTC 3' (SEQ ID NO:31). Oligonucleotide primers complementary to 18S RNA and to mRNAs encoding the 'housekeeper' proteins, in this instance, muHPRT (hypoxanthine phosphoribosyltransferase), were synthesized and PCR conditions were optimized for these primer sets also. Multiplex TaqMan PCR reactions using both CtLL polypeptide and muHPRT probe/primer sets were set up in 25-microliter volumes with TaqMan Universal PCR Master Mix (product #4304437, Applied Biosystems, Foster City, Calif.) on an Applied Biosystems Prism 7700 Sequence Detection System. Threshold cycle values ($C_T$) were determined using Sequence Detector software version 1.7a (Applied Biosystems, Foster City, Calif.), and delta $C_T$ was calculated and transformed to $2e(-dC_T)$, which is 2 to the minus delta $C_T$, for relative expression comparison of CtLL to muHPRT. For example, a ratio of expression of 0.0136 indicates that the expression of CtLL is 1.36% that of the housekeeping gene.

In one set of experiments, expression of murine CtLL polypeptide relative to muHPRT was analyzed in a variety of normal adult mouse tissue samples. RNA was extracted from various tissues of adult C57B1/6 mice (in all cases samples were pools from multiple mice) and expression of CtLL compared with that of muHPRT. This analysis indicated that CtLL messages are detectable and express at less than 10% of housekeeper mRNAs in many adult tissues, including thymus, spleen, bone marrow, brain, spinal chord, kidney, skeletal muscle, heart, uterus, and ovaries. The highest expression levels was found in the lymph nodes at 12% of housekeeper; the lung, at 78% of housekeeper, and in particular, the testis, at 834% of housekeeping.

CtLL polypeptide expression relative to housekeeper gene expression in tissue samples from a mouse asthma model was also analyzed. Experiments using C57B1/6 mice were performed as follows. Naïve mice received no priming and no challenge. Unchallenged and challenged mice were primed with an intranasal exposure to 10 ug ovalbumin at day −21 and −14 prechallenge. Challenged mice were exposed intranasally to ovalbumin at 100 ug/50 ul on a one dose, two dose, or three dose schedule over a period of up to 48 hours; then sacrificed at 96 hr, the lungs removed, and expression of murine CtLL polypeptide analyzed as described above. The results of this analysis are presented in Table 2 below. The CB and DS designation refers to two separate sets of experiments. It was generally found that expression of murine CttLL was highest in naïve and unchallenged mice, and that expression was down-regulated by 34 times in a challenged animal compared with the expression in naïve or unchalleged animals.

TABLE 2

| Sample | muCtLL Avg CT | muHPRT Avg CT | 2e-dCT | Minus Err | Plus Err |
| --- | --- | --- | --- | --- | --- |
| CB1102 48 h dose3 A1 | 33.4633 | 29.4167 | 0.0605107 | 0.0520026 | 0.0704108 |
| CB1102 48 h dose3 A2 | 32.7133 | 29.5267 | 0.1098292 | 0.0971053 | 0.1242202 |
| CB1102 24 h dose3 B1 | 32.35 | 28.73 | 0.0813339 | 0.0761669 | 0.0868514 |
| CB1102 24 h dose3 B2 | 31.76 | 28.39 | 0.0967228 | 0.0789843 | 0.1184451 |
| CB1102 24 h dose1 C1 | 31 | 28.4733 | 0.1735392 | 0.1601695 | 0.1880249 |
| CB1102 24 h dose1 C2 | 31.95 | 28.7533 | 0.1090705 | 0.0969641 | 0.1226885 |
| CB1102 4 h dose1 D1 | 30.5533 | 27.84 | 0.1524773 | 0.1367968 | 0.1699553 |
| CB1102 4 h dose1 D2 | 30.5033 | 28.2633 | 0.2116863 | 0.2044913 | 0.2191345 |
| CB1102 no cha1 E1 | 30.24 | 28.21 | 0.2448551 | 0.2365693 | 0.2534311 |
| CB1102 no cha1 E2 | 30.2533 | 27.75 | 0.1763687 | 0.1582079 | 0.1966142 |
| CB1102 Naive F1 | 30.67 | 28.4 | 0.2073299 | 0.2029856 | 0.2117671 |
| CB1102 Naive F2 | 30.0433 | 27.67 | 0.1929992 | 0.1750592 | 0.2127777 |

TABLE 2-continued

| Sample | muCtLL Avg CT | muHPRT Avg CT | 2e-dCT | Minus Err | Plus Err |
|---|---|---|---|---|---|
| DS0602 48 h dose3 A1 | 32.2067 | 28.8233 | 0.095833 | 0.084875 | 0.1082058 |
| DS0602 48 h dose3 A2 | 30.8933 | 28.21 | 0.1556812 | 0.14785 | 0.1639273 |
| DS0602 24 h dose3 B1 | 31.61 | 28.1767 | 0.0925686 | 0.089209 | 0.0960547 |
| DS0602 24 h dose3 B2 | 30.6467 | 27.1067 | 0.0859714 | 0.0796628 | 0.0927795 |
| DS0602 24 h dose1 C1 | 29.97 | 28.06 | 0.2660926 | 0.2394133 | 0.2957448 |
| DS0602 24 h dose1 C2 | 29.9033 | 27.9333 | 0.255253 | 0.2418856 | 0.2693592 |
| DS0602 4 h dose1 D1 | 30.9533 | 29.5667 | 0.3824474 | 0.3586521 | 0.4078215 |
| DS0602 4 h dose1 D2 | 29.8567 | 27.97 | 0.2704312 | 0.2645359 | 0.2764578 |
| DS0602 no cha1 E1 | 29.77 | 28.1467 | 0.3245847 | 0.2875334 | 0.3664102 |
| DS0602 no cha1 E2 | 30.13 | 28.1367 | 0.2511579 | 0.2409578 | 0.2617899 |
| DS0602 Naive F1 | 29.08 | 27.8333 | 0.4214208 | 0.4090606 | 0.4341545 |
| DS0602 Naive F2 | 29.64 | 28.3433 | 0.4070656 | 0.3827274 | 0.4329516 |
| Negative | 40 | 40 | 0 | 0 | 0 |

These results may suggest that during inflammation, macrophage processing of apoptotic cells is downregulated, perhaps to protect against excessive autoantigen presentation. This would be consistant with the lower level of CtLL expression when macrophages are activated in vitro.

Example 8

Analysis of CtLL Polypeptide Expression in Human Samples by Real-Time Quantitative PCR RNA samples from human tissues were obtained commercially (Ambion, Austin, Tex.). The RNA samples were DNase treated (product #1906, Ambion, Austin, Tex.), and reverse transcribed into a population of cDNA molecules using TAQ-MAN® Reverse Transcription Reagents (product #N808-0234, Applied Biosystems, Foster City, Calif.) according to the manufacturer's instructions using random hexamers as described above. Each population of cDNA molecules was placed into specific wells of a multi-well plate at either 5 ng or 20 ng per well and run in triplicate. Pooling was used when same tissue types and stimulation conditions were applied but collected from different donors. Negative control wells were included in each multi-well plate of samples.

Sets of probes and oligonucleotide primers complementary to mRNAs encoding a CtLL polypeptide (SEQ ID NO: 12) were designed using Primer Express software (Applied Biosystems, Foster City, Calif.) and synthesized, and PCR conditions for these probe/primer sets were optimized to produce a steady and logarithmic increase in PCR product every thermal cycle between approximately cycle 20 and cycle 36. The forward CtLL primer used was 5' AGT GTA CTG AAG AGG CAG GAA CAA 3' (SEQ ID NO:32); the reverse CtLL primer used was 5' GAC ATG GAT TAC ATC TGT GGT CTG A 3' (SEQ ID NO:33); and the labeled probe used for CtLL polypeptide was 5' TGG CCA TCA AAC TGT GCC AAG AGC 3' (SEQ ID NO:34). Oligonucleotide primers complementary to 18S RNA and to mRNAs encoding either HPRT (hypoxanthine phosphoribosyltransferase) or β-actin were synthesized and PCR conditions were optimized for these primer sets also. Multiplex TaqMan PCR reactions using both human CtLL polypeptide and probe/primer sets were set up in 25-microliter volumes with TaqMan Universal PCR Master Mix (product #430-4437, Applied Biosystems, Foster City, Calif.) on an Applied Biosystems Prism 7700 Sequence Detection System. Threshold cycle values ($C_T$) were determined using Sequence Detector software version 1.7a (Applied Biosystems, Foster City, Calif.), and delta $C_T$ was calculated and transformed to 2e($-dC_T$), which is 2 to the minus delta $C_T$, for relative expression comparison of CtLL to HPRT or β-actin.

Analysis of CtLL expression relative to HPRT was performed using normal human tissue samples. The following results were obtained. Expression was found at 28.38% of housekeeper for testis, 2.76% for spleen, 116% of housekeeping for skin, 6.58% for lung, and 1.56% for spinal chord. These results are presented in Table 3.

TABLE 3

| Sample | huCtLL Avg CT | HPRT Avg CT | 2e-dCT | Minus Err | Plus Err |
|---|---|---|---|---|---|
| Sm Intestine | 37.07 | 29.48 | 0 | 0 | 0 |
| Stomach | 40 | 30.28 | 0 | 0 | 0 |
| Testis | 28.17 | 26.353 | 0.2838761 | 0.2626444 | 0.3068242 |
| Colon | 38.6467 | 30.05 | 0 | 0 | 0 |
| Prostate | 40 | 29.803 | 0 | 0 | 0 |
| Adrenal | 40 | 29.617 | 0 | 0 | 0 |
| Ovary | 40 | 29.273 | 0 | 0 | 0 |
| Pancreas | 39.68 | 30.3 | 0 | 0 | 0 |
| Sk Muscle | 40 | 31.703 | 0 | 0 | 0 |
| Spleen | 40 | 31.65 | 0 | 0 | 0 |
| Thymus | 37.3333 | 30.443 | 0 | 0 | 0 |
| F Stomach | 39.0667 | 31.067 | 0 | 0 | 0 |
| F Spleen | 34.8467 | 29.67 | 0.0276483 | 0.0217914 | 0.0350793 |
| F Lung | 39.8567 | 32.62 | 0 | 0 | 0 |
| F Colon | 37.76 | 30.153 | 0 | 0 | 0 |
| Thyroid | 36.6333 | 30.263 | 0 | 0 | 0 |
| Skin | 31.0367 | 31.253 | 1.1620456 | 1.1172113 | 1.2086791 |
| F Kidney | 39.58 | 29.697 | 0 | 0 | 0 |
| F Sk Muscle | 40 | 30.5 | 0 | 0 | 0 |
| Uterus | 37.3767 | 30.29 | 0 | 0 | 0 |
| Brain | 39.7 | 29.873 | 0 | 0 | 0 |
| Liver | 40 | 34.263 | 0 | 0 | 0 |
| Heart | 40 | 34.623 | 0 | 0 | 0 |
| Kidney | 40 | 30.073 | 0 | 0 | 0 |
| Lung | 35.8 | 31.873 | 0.0657591 | 0.0522674 | 0.0827332 |
| Trachea | 38.3333 | 30.59 | 0 | 0 | 0 |
| Cerebellum | 40 | 29.19 | 0 | 0 | 0 |
| F Brain | 40 | 28.593 | 0 | 0 | 0 |
| Spinal Cord | 35.61 | 29.603 | 0.015553 | 0.0137479 | 0.0175951 |
| F Liver | 39.2367 | 29.303 | 0 | 0 | 0 |
| Placenta | 39.7133 | 33.193 | 0 | 0 | 0 |
| NEG | 40 | 40 | 0 | 0 | 0 |

In other expression analyses, no expression was detected in dendritic cells. However, a low but significant CtLL expression (0.001079% of β-Actin) was detected in monocytes. No detectable expression was found in bone tissue or adipose tissue, or in various tissues subjected to treatments using a variety of cytokines and other factors.

Although the foregoing invention has been described in some detail by way of illustration and example for purposes of clarity of understanding, it will be readily apparent to those

What is claimed is:

1. An isolated polynucleotide encoding a polypeptide selected from the group consisting of:
   (a) a polypeptide consisting of SEQ ID NO:12;
   (b) a polypeptide consisting of amino acid residues 66 to 276 of SEQ ID NO:12; and
   (c) a polypeptide consisting of amino acid residues 142 to 276 of SEQ ID NO: 12, wherein the polypeptide has calcium-dependent lectin activity.

2. An isolated polynucleotide encoding a polypeptide consisting of SEQ ID NO: 12, wherein the polypeptide has calcium-dependent lectin activity.

3. An isolated polynucleotide selected from the group consisting of:
   (a) a polynucleotide consisting of SEQ ID NO: 11;
   (b) a polynucleotide selected from the group consisting of: nucleotides 244 to 876 of SEQ ID NO:11; and nucleotides 475 to 876 of SEQ ID NO:11;
   (c) a polynucleotide that is the full complement of the polynucleotide of (a) or (b); and
   (d) the polynucleotide of (a), (b) or (c) wherein nucleotide T is replaced with U.

4. An isolated polynucleotide comprising the nucleotide sequence of SEQ ID NO: 11.

5. An expression vector comprising the polynucleotide of claim 1.

6. A recombinant host cell comprising the expression vector of claim 5 genetically engineered to produce a polypeptide consisting of SEQ ID NO:12.

7. A method for producing the polypeptide of claim 6 comprising culturing the host cell under conditions promoting expression of the polypeptide and purifying the polypeptide.

* * * * *